United States Patent
Huh et al.

(10) Patent No.: US 11,737,354 B2
(45) Date of Patent: Aug. 22, 2023

(54) ORGANIC LIGHT EMITTING DEVICE HAVING A CARBAZOLE-BASED COMPOUND FORMED BETWEEN A CATHODE AND A LIGHT EMITTING LAYER AND A SPIROBIFLUORENE-MONOAMINE-BASED COMPOUND FORMED BETWEEN AN ANODE AND A LIGHT EMITTING LAYER

(71) Applicant: LG CHEM, LTD., Seoul (KR)

(72) Inventors: Jungoh Huh, Daejeon (KR); Dong Hoon Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 408 days.

(21) Appl. No.: 16/888,395

(22) Filed: May 29, 2020

(65) Prior Publication Data

US 2020/0295264 A1 Sep. 17, 2020

Related U.S. Application Data

(63) Continuation of application No. 14/767,552, filed as application No. PCT/KR2014/010323 on Oct. 31, 2014, now Pat. No. 10,714,692.

(30) Foreign Application Priority Data

Oct. 1, 2014 (KR) .................. 10-2014-0132287
Oct. 27, 2014 (KR) .................. 10-2014-0146410

(51) Int. Cl.
*H01L 51/50* (2006.01)
*H10K 85/60* (2023.01)
(Continued)

(52) U.S. Cl.
CPC ......... *H10K 85/633* (2023.02); *C07D 209/82* (2013.01); *C07D 403/10* (2013.01);
(Continued)

(58) Field of Classification Search
CPC .............. H01L 51/006; H01L 51/0067; H01L 51/0072; H10K 85/631; H10K 85/654
See application file for complete search history.

(56) References Cited

U.S. PATENT DOCUMENTS

2013/0200359 A1    8/2013    Stoessel et al.
2013/0207046 A1    8/2013    Pflumm et al.
(Continued)

FOREIGN PATENT DOCUMENTS

CN    103180407    6/2013
CN    104066728    9/2014
(Continued)

OTHER PUBLICATIONS

Tang C. W. and Vanslyke S. A., "Organic electroluminescent diodes," Appl. Phys. Lett. 51(12): 913-915 (1987).
(Continued)

*Primary Examiner* — Anh D Mai
(74) *Attorney, Agent, or Firm* — Dentons US LLP

(57) ABSTRACT

Provided is an organic light emitting device having between the cathode and a light emitting layer an an organic material layer containing a compound of any one of the following Chemical Formulae 1-2 to 1-4:

(Continued)

Chemical Formula 1-2

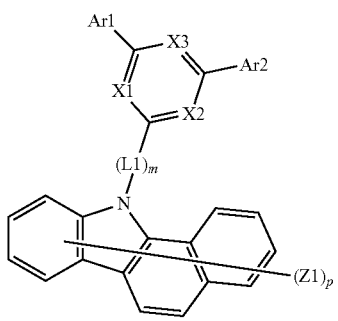

Chemical Formula 1-3

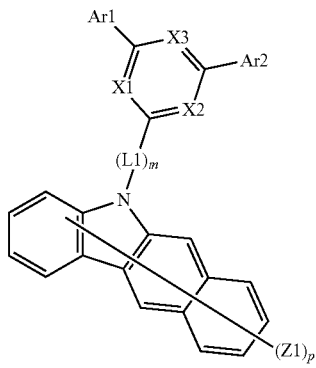

Chemical Formula 1-4

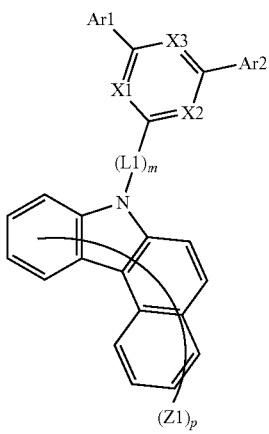

wherein:
X1 to X3 are each independently N or CH, and at least one of X1 to X3 is N;
L1 is a substituted or unsubstituted monocyclic arylene group having 6 to 24 carbon atoms;
Ar1 and Ar2 are the same as or different from each other, and are each independently a substituted or unsubstituted monocyclic or polycyclic aryl group having 6 to 20 carbon atoms; and
Z1 is deuterium;
and an organic material layer provided between the anode and the light emitting layer and including a spirobifluorene-monoamine based compound of Chemical Formula 2:

Chemical Formula 2

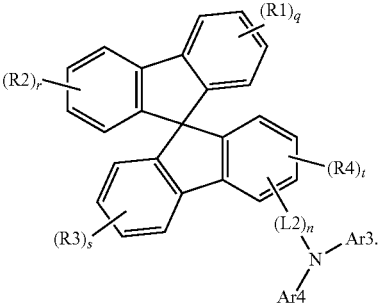

19 Claims, 1 Drawing Sheet

(51) Int. Cl.
C07D 403/10 (2006.01)
C09K 11/06 (2006.01)
C07D 209/82 (2006.01)
H10K 50/00 (2023.01)
H10K 50/16 (2023.01)
H10K 50/18 (2023.01)
H10K 50/17 (2023.01)
H10K 85/30 (2023.01)

(52) U.S. Cl.
CPC .............. *C09K 11/06* (2013.01); *H10K 50/00* (2023.02); *H10K 85/631* (2023.02); *H10K 85/654* (2023.02); *H10K 85/6572* (2023.02); *H10K 50/16* (2023.02); *H10K 50/171* (2023.02); *H10K 50/18* (2023.02); *H10K 85/324* (2023.02); *H10K 85/342* (2023.02)

(56) References Cited

U.S. PATENT DOCUMENTS

| | | |
|---|---|---|
| 2014/0070204 A1 | 3/2014 | Nagao et al. |
| 2014/0197386 A1 | 7/2014 | Kim et al. |
| 2014/0316136 A1 | 10/2014 | Yang et al. |
| 2015/0228899 A1 | 8/2015 | Kato et al. |
| 2015/0318510 A1 | 11/2015 | Ito et al. |

FOREIGN PATENT DOCUMENTS

| | | |
|---|---|---|
| JP | 2009-021336 | 1/2009 |
| KR | 10-20130099098 | 9/2013 |
| KR | 10-20140096203 | 8/2014 |
| WO | 2012108881 | 8/2012 |
| WO | 2012153725 | 11/2012 |
| WO | 2013175747 | 11/2013 |
| WO | 2014034791 | 3/2014 |

OTHER PUBLICATIONS

International Search Report and the Written Opinion of PCT/KR2014/010323, dated Jun. 19, 2015.

[Figure 1]
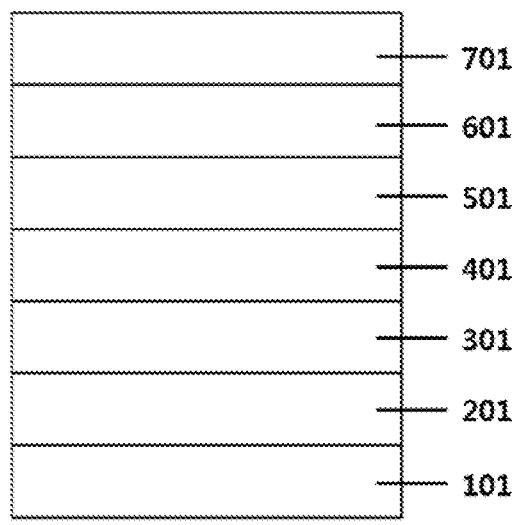
[Figure 2]
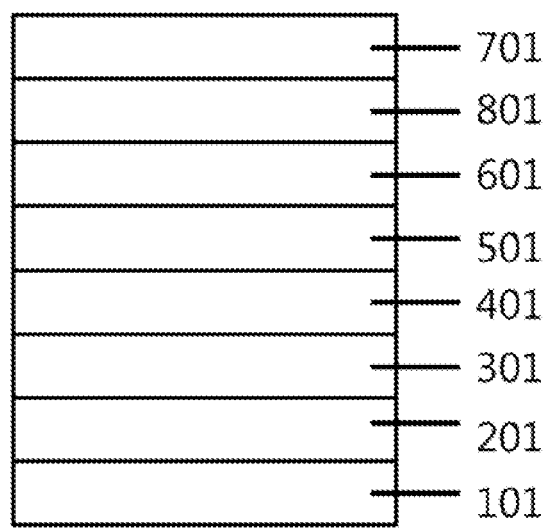

ORGANIC LIGHT EMITTING DEVICE HAVING A CARBAZOLE-BASED COMPOUND FORMED BETWEEN A CATHODE AND A LIGHT EMITTING LAYER AND A SPIROBIFLUORENE-MONOAMINE-BASED COMPOUND FORMED BETWEEN AN ANODE AND A LIGHT EMITTING LAYER

CROSS-REFERENCE TO RELATED APPLICATIONS

This application is a continuation of co-pending allowed U.S. patent application Ser. No. 14/767,552, filed Aug. 12, 2015, which is a National Stage Application of International Application No. PCT/KR2014/010323 filed on Oct. 31, 2014, which claims priority to and the benefit of Korean Patent Application No. 10-2014-0132287 filed in the Korean Intellectual Property Office on Oct. 1, 2014, and Korean Patent Application No. 10-2014-0146410, filed with the Korean Intellectual Property Office on Oct. 27, 2014, the entire contents of which are incorporated herein by reference.

TECHNICAL FIELD

The present specification relates to an organic light emitting diode.

BACKGROUND ART

An organic light emission phenomenon is an example of converting current into visible rays by an internal process of a specific organic molecule. A principle of the organic light emission phenomenon is as follows.

When an organic material layer is positioned between an anode and a cathode, if a voltage is applied between two electrodes, electrons and holes are respectively injected from the cathode and the anode into the organic material layer. The electrons and the holes which are injected into the organic material layer are recombined to form excitons, and light is emitted while the excitons fall down to a bottom state again. In general, an organic light emitting diode using this principle may be constituted by a cathode, an anode, and an organic material layer positioned therebetween, for example, an organic material layer including a hole injection layer, a hole transport layer, a light emitting layer, and an electron transport layer.

A material used for the organic light emitting diode is mostly a pure organic material or a complex compound where an organic material and metal form a complex, and may be classified into a hole injection material, a hole transport material, a light emitting material, an electron transport material, an electron injection material, and the like according to the purpose thereof. Herein, an organic material having a p-type property, that is, an organic material that is easily oxidized and has an electrochemically stable state during oxidation, is mostly used as the hole injection material or the hole transport material. Meanwhile, an organic material having an n-type property, that is, an organic material that is easily reduced and has an electrochemically stable state during reduction, is mostly used as the electron injection material or the electron transport material.

As a light emitting layer material, a material having both p-type and n-type properties, that is, a material having a stable form in both oxidation and reduction states is preferable. Also, a material having high light emitting efficiency for converting the exciton into light when the exciton is formed is preferable.

In the art, there is a demand for developing an organic light emitting diode having high efficiency.

PRIOR ART DOCUMENT

Non-Patent Document

Applied Physics Letters 51, p. 913, 1987

DETAILED DESCRIPTION OF THE INVENTION

Technical Problem

The present specification has been made in an effort to provide an organic light emitting diode having high light emitting efficiency.

Technical Solution

An exemplary embodiment of the present specification provides an organic light emitting diode including: an anode; a cathode; a light emitting layer provided between the anode and the cathode; an organic material layer including a compound represented by the following Chemical Formula 1 and provided between the cathode and the light emitting layer; and an organic material layer including a compound represented by the following Chemical Formula 2 and provided between the anode and the light emitting layer.

Chemical Formula 1

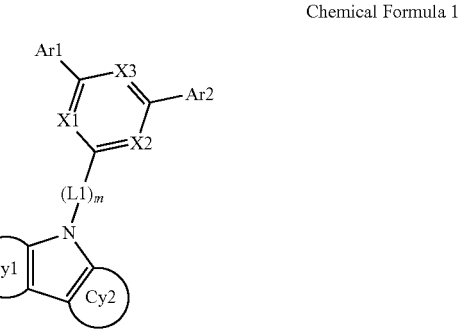

In Chemical Formula 1, $X_1$ to $X_3$ are the same as or different from each other, and are each independently N or CH, at least one of $X_1$ to $X_3$ is N, Cy1 and Cy2 are the same as or different from each other, and are each independently a substituted or unsubstituted monocyclic or polycyclic aromatic cycle having 6 to 30 carbon atoms; or a substituted or unsubstituted monocyclic or polycyclic heterocycle having 2 to 30 carbon atoms, L1 is a substituted or unsubstituted monocyclic or polycyclic arylene group having 6 to 30 carbon atoms, m is an integer of 1 to 4, in the case where m is an integer of 2 or more, two or more L1 s are the same as or different from each other, and Ar1 and Ar2 are the same as or different from each other, and are each independently a substituted or unsubstituted monocyclic or polycyclic aryl group having 6 to 30 carbon atoms; or a substituted or unsubstituted monocyclic or polycyclic heteroaryl group having 2 to 30 carbon atoms,

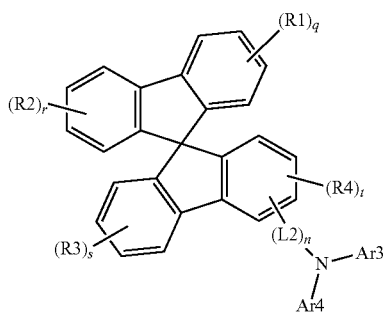

Chemical Formula 2 in Chemical Formula 2,

Ar3 and Ar4 are the same as or different from each other, and are each independently hydrogen; deuterium; a substituted or unsubstituted monocyclic or polycyclic aryl group having 6 to 30 carbon atoms; or a substituted or unsubstituted monocyclic or polycyclic heteroaryl group having 2 to 30 carbon atoms, or are bonded to each other to form a substituted or unsubstituted cycle, L2 is a substituted or unsubstituted monocyclic or polycyclic arylene group having 6 to 30 carbon atoms, n is an integer of 0 to 5, in the case where n is 2 or more, two or more L2s are the same as or different from each other, R1 to R4 are the same as or different from each other, and are each independently hydrogen; deuterium; a substituted or unsubstituted straight-chained or branch-chained alkyl group having 1 to 30 carbon atoms; a substituted or unsubstituted monocyclic or polycyclic aryl group having 6 to 30 carbon atoms; or a substituted or unsubstituted monocyclic or polycyclic heteroaryl group having 2 to 30 carbon atoms, or adjacent groups are bonded to each other to form a substituted or unsubstituted aromatic cycle, q, r, and s are each an integer of 1 to 4, t is an integer of 1 to 3, in the case where q is 2 or more, two or more R1s are the same as or different from each other, in the case where r is 2 or more, two or more R2s are the same as or different from each other, in the case where s is 2 or more, two or more R3s are the same as or different from each other, and in the case where t is 2 or more, two or more R4s are the same as or different from each other.

Advantageous Effects

An organic light emitting diode according to an exemplary embodiment of the present specification provides a low driving voltage and/or high efficiency.

BRIEF DESCRIPTION OF DRAWINGS

FIG. 1 illustrates an example of an organic light emitting diode according to an exemplary embodiment of the present specification.

FIG. 2 illustrates an example of an organic light emitting diode according to an exemplary embodiment of the present specification.

EXPLANATION OF REFERENCE NUMERALS AND SYMBOLS

101: Substrate
201: Anode
301: Hole transport layer
401: Electron blocking layer
501: Light emitting layer
601: Electron transport layer
701: Cathode
801: Electron injection layer

BEST MODE

Hereinafter, the present specification will be described in more detail.

In the present specification, unless explicitly described to the contrary, the word "comprise" and variations such as "comprises" or "comprising", will be understood to imply the inclusion of stated elements but not the exclusion of any other elements.

In the present specification, it will be understood that when an element is referred to as being positioned "on" another element, it can be directly on the other element or intervening elements may also be present between the two elements.

An organic light emitting diode according to an exemplary embodiment of the present specification includes both an organic material layer including a compound represented by Chemical Formula 1 and an organic material layer including a compound represented by Chemical Formula 2.

According to the exemplary embodiment of the present specification, the organic material layer including the compound represented by Chemical Formula 1 is an electron transport layer, an electron injection layer, or a layer simultaneously transporting and injecting electrons.

According to one exemplary embodiment of the present specification, the organic material layer including the compound represented by Chemical Formula 1 is the electron transport layer.

According to another exemplary embodiment of the present specification, an organic material layer including a compound represented by Chemical Formula 1 is an electron injection and electron transport layer. Specifically, in the organic light emitting diode according to the exemplary embodiment of the present specification, in the case where the electron injection layer is not provided, the organic material layer including the compound represented by Chemical Formula 1 may serve as both the electron injection layer and electron transport layer.

Further, according to another exemplary embodiment of the present specification, the organic light emitting diode may include only the organic material layer including the compound represented by Chemical Formula 1 between a cathode and a light emitting layer. In another exemplary embodiment, the organic light emitting diode may further include an additional organic material layer between the cathode and the organic material layer including the compound represented by Chemical Formula 1; or between the light emitting layer and the organic material layer including the compound represented by Chemical Formula 1.

According to the exemplary embodiment of the present specification, the organic material layer including the compound represented by Chemical Formula 2 is an electron blocking layer.

In the related art, an organic material having an n-type property, that is, an organic material that is easily reduced and has an electrochemically stable state during reduction, is mostly used as an electron transport material. However, the organic material is electrochemically unstable during oxidation, a novel electron transport material has been continuously studied.

The compound represented by Chemical Formula 1 according to the exemplary embodiment of the present specification has a bipolar type both having a p-type property (cycle group including Cy1 and Cy2) and an n-type property (cycle group including X1 to X3), and thus has a stable state in both oxidation and reduction states. Accordingly, it is possible to obtain an effect that when an exciton is formed, light emitting efficiency of converting the exciton into light is high.

Like the organic light emitting diode according to the exemplary embodiment of the present specification, in the case where the compound having the bipolar property of the p-type and n-type properties and represented by Chemical Formula 1 is used as the electron transport layer and the organic material layer including the compound represented by Chemical Formula 2 is used as the electron blocking layer, an increase in efficiency may be maximized.

In the case where the organic material layer including the compound represented by Chemical Formula 2 is used as the electron blocking layer, since the generated exciton is confined in the light emitting layer to prevent light emission leakage, the organic light emitting diode having excellent light emitting efficiency may be implemented. In this case, when the electron transport layer adjacent to the light emitting layer is the bipolar type including both the p type and the n type rather than the pure n type, the generated exciton as well as the leaked holes may be effectively confined in the light emitting layer, and a stable form of the exciton, that is, hole-electron pairs against chemical attack may be maintained, a life-span as well as efficiency may be maximized.

According to another exemplary embodiment of the present specification, the organic material layer including the compound represented by Chemical Formula 2 is provided to come into contact with the light emitting layer. In this case, an effect of the organic material layer including the compound represented by Chemical Formula 2 as the electron blocking layer may be maximized.

According to the exemplary embodiment of the present specification, the organic light emitting diode further includes one or two or more layers from the group consisting of the electron injection layer and the electron transport layer between the light emitting layer and the cathode.

According to another exemplary embodiment of the present specification, the organic material layer including the compound represented by Chemical Formula 1 is the electron transport layer, and further includes the electron injection layer provided between the electron transport layer and the cathode.

According to the exemplary embodiment of the present specification, the organic light emitting diode further includes one or two or more from the group consisting of a hole injection layer, a hole transport layer, and an electron blocking layer between the light emitting layer and the anode.

According to another exemplary embodiment of the present specification, the organic material layer including the compound represented by Chemical Formula 2 is the electron blocking layer, and further includes the hole transport layer provided between the electron blocking layer and the anode.

In the present specification, examples of substituent groups will be described below, but are not limited thereto.

The term "substituted" means that a hydrogen atom bonded to a carbon atom of a compound is changed into another substituent group, a substitution position is not limited as long as the substitution position is a position at which the hydrogen atom is substituted, that is, a position at which the substituent group can be substituted, and in the case where two or more atoms are substituted, two or more substituent groups may be the same as or different from each other.

In the present specification, the term "substituted or unsubstituted" means that substitution is performed by one or two or more substituent groups selected from the group consisting of deuterium; a halogen group; a nitrile group; a nitro group; an imide group; an amide group; a hydroxy group; a substituted or unsubstituted alkyl group; a substituted or unsubstituted cycloalkyl group; a substituted or unsubstituted alkoxy group; a substituted or unsubstituted alkenyl group; a substituted or unsubstituted amine group; a substituted or unsubstituted aryl group; and a substituted or unsubstituted heterocyclic group, substitution is performed by a substituent group where two or more substituent groups of the exemplified substituent groups are connected, or there is no substituent group. For example, the "substituent group where two or more substituent groups are connected" may be a biphenyl group. That is, the biphenyl group may be an aryl group, or may be interpreted as a substituent group where two phenyl groups are connected. The term "substituted or unsubstituted" means that substitution is performed by the substituent group where two or more substituent groups of the exemplified substituent groups are connected or there is no substitution. For example, the "substituent group where two or more substituent groups are connected" may be a biphenyl group. That is, the biphenyl group may be an aryl group, or may be interpreted as a substituent group where two phenyl groups are connected.

In the present specification,

means a portion bonded to another substituent group or a bonding portion.

In the present specification, a halogen group may be fluorine, chlorine, bromine or iodine.

In the present specification, the number of carbon atoms of an imide group is not particularly limited but is preferably 1 to 30. Specifically, the imide group may be compounds having the following structures, but is not limited thereto.

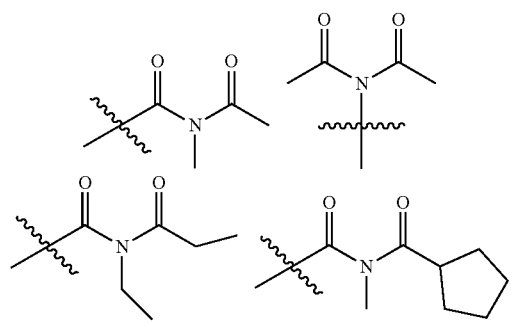

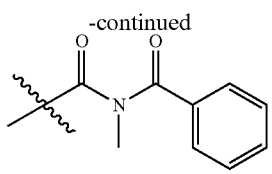

In the present specification, one or two nitrogen atoms of an amide group may be substituted by hydrogen, a straight-chained, branched-chained, or cyclic-chained alkyl group having 1 to 30 carbon atoms, or an aryl group having 6 to 30 carbon atoms. Specifically, the amide group may be compounds having the following Structural Formulas, but is not limited thereto.

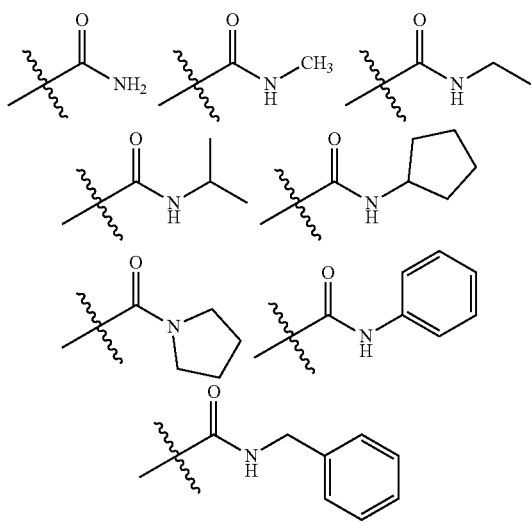

In the present specification, an alkyl group may be a straight or branched chain, and the number of carbon atoms thereof is not particularly limited but is preferably 1 to 30. Specific examples thereof include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethyl-heptyl, 1-ethyl-propyl, 1,1-dimethyl-propyl, isohexyl, 2-methylpentyl, 4-methyl-hexyl, 5-methylhexyl, and the like, but are not limited thereto.

In the present specification, a cycloalkyl group is not particularly limited, but the number of carbon atoms thereof is preferably 3 to 30, and specific examples thereof include cyclopropyl, cyclobutyl, cyclopentyl, 3-methyl-cyclopentyl, 2,3-dimethylcyclopentyl, cyclohexyl, 3-methylcyclohexyl, 4-methyl-cyclohexyl, 2,3-dimethylcyclohexyl, 3,4,5-trimethylcyclohexyl, 4-tert-butyl-cyclohexyl, cycloheptyl, cyclooctyl, and the like, but are not limited thereto.

In the present specification, the alkoxy group may be a straight, branched, or cyclic chain. The number of carbon atoms of the alkoxy group is not particularly limited, but preferably 1 to 30. Specific examples thereof may include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy, and the like, but are not limited thereto.

In the present specification, the alkenyl group may be a straight or branched chain, and the number of carbon atoms thereof is not particularly limited but is preferably 2 to 30. Specific examples thereof include vinyl, 1-prophenyl, isoprophenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, an amine group may be selected from the group consisting of —NH₂; an alkylamine group; an aralkylamine group; an arylamine group; and a heteroarylamine group, and the number of carbon atoms thereof is not particularly limited, but is preferably 1 to 30. Specific examples of the amine group include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, a phenylnaphthylamine group, a ditolylamine group, a phenyltolylamine group, a triphenylamine group, and the like, but are not limited thereto.

In the case where the aryl group is the monocyclic aryl group, the number of carbon atoms thereof is not particularly limited but is preferably 6 to 25. Specific examples of the monocyclic aryl group may include a phenyl group, a biphenyl group, a terphenyl group, and the like, but are not limited thereto.

In the case where the aryl group is the polycyclic aryl group, the number of carbon atoms thereof is not particularly limited but is preferably 10 to 24. Specific examples of the polycyclic aryl group may include a naphthyl group, a triphenylenyl group, an anthracenyl group, a phenanthryl group, a pyrenyl group, a perylenyl group, a chrysenyl group, a fluorenyl group, and the like, but are not limited thereto.

In the present specification, the fluorenyl group may be substituted, and the adjacent substituent groups may be bonded to each other to form a cycle.

In the case where the fluorenyl group is substituted,

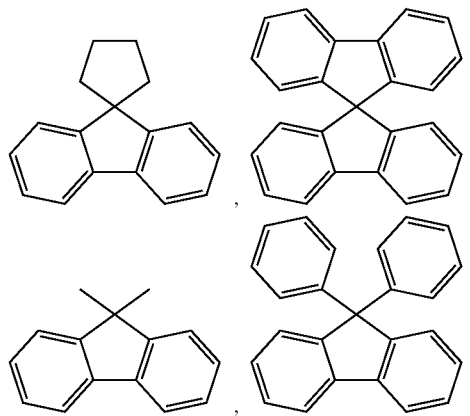

and the like may be formed. However, the fluorenyl group is not limited thereto.

In the present specification, the heterocyclic group includes an atom other than carbon, that is, one or more heteroatoms, and specifically, the heteroatom may include one or more atoms selected from the group consisting of O, N, Se, S, and the like. The number of carbon atoms thereof is not particularly limited, but preferably 2 to 60. Examples of the heterocyclic group include a thiophene group, a furan group, a pyrrole group, an imidazole group, a thiazole group, an oxazol group, an oxadiazol group, a triazol group, a pyridyl group, a bipyridyl group, a pyrimidyl group, a triazine group, a triazole group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazol group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group, and the like, but are not limited thereto.

The heterocyclic group may be a monocycle or a polycycle, and may be aromatics, aliphatics, or a condensation cycle of the aromatics and the aliphatics.

In the present specification, the heteroaryl group may be selected from the aforementioned examples of the heterocyclic group.

In the present specification, the arylene group means a matter where two bonding positions exist at the aryl group, that is, a divalent group. Except that the groups are each the divalent group, the aforementioned description of the aryl group may be applied thereto.

In the present specification, an aromatic cycle may be a monocyclic or a polycycle, and may be selected from the aforementioned examples of the aryl group, except that the aromatic cycle is not monovalent.

In the present specification, the heterocycle may be an aliphatic cycle or an aromatic cycle, means a matter in which at least one carbon atom of the aliphatic or aromatic cycle is substituted by a N, O, or S atom, may be a monocycle or a polycycle, and may be selected from the aforementioned examples of the heteroaryl group, except that the heterocycle is not monovalent.

In the present specification, the "adjacent" group may mean a substituent group substituted in an atom directly connected to an atom where the corresponding substituent group is substituted, a substituent group that is positioned sterically closest to the corresponding substituent group, or another substituent group substituted in an atom where the corresponding substituent group is substituted. For example, two substituent groups substituted at an ortho position in a benzene cycle and two substituent groups substituted at the same carbon in the aliphatic cycle may be interpreted as the groups "adjacent" to each other.

In the present specification, formation of the aromatic cycle by bonding the adjacent groups to each other means formation of a 5-membered to 8-membered monocyclic or polycyclic aromatic cycle by forming a bond between the adjacent substituent groups, and the aromatic cycle may be selected from the aforementioned examples of the aryl group. Specifically, according to the exemplary embodiment of the present specification, the adjacent groups may be bonded to each other to form a dihydroacridine structure. In the present specification, the cycle formed by bonding the adjacent groups to each other may be a monocycle or a polycycle, and may form a hydrocarbon cycle or a heterocycle. The hydrocarbon cycle may be aliphatics, aromatics, or a condensation cycle of the aliphatics and the aromatics, and may be selected from the aforementioned examples of the cycloalkyl group or the aryl group except for a hydrocarbon cycle other than the monovalent group. The heterocycle may be aliphatics, aromatics, or a condensation cycle of the aliphatics and the aromatics, and may be selected from the aforementioned examples of the heterocycle group except for a heterocycle other than the monovalent group.

According to the exemplary embodiment of the present specification, in Chemical Formula 1, at least one of $X_1$ to $X_3$ is N.

In the exemplary embodiment of the present specification, $X_1$ may be N and $X_2$ and $X_3$ may be CH.

In the exemplary embodiment of the present specification, $X_2$ may be N and $X_1$ and $X_3$ may be CH.

In the exemplary embodiment of the present specification, $X_3$ may be N and $X_1$ and $X_2$ may be CH.

According to another exemplary embodiment of the present specification, at least two of $X_1$ to $X_3$ are N.

In the exemplary embodiment of the present specification, $X_1$ and $X_2$ may be N. In this case, $X_3$ is CH.

In the exemplary embodiment of the present specification, $X_1$ and $X_3$ may be N. In this case, $X_2$ is CH.

In the exemplary embodiment of the present specification, $X_2$ and $X_3$ may be N. In this case, $X_1$ is CH.

According to another exemplary embodiment of the present specification, $X_1$ to $X_3$ are N.

According to the exemplary embodiment of the present specification, in Chemical Formula 1, Cy1 and Cy2 are the same as or different from each other, and are each independently a substituted or unsubstituted monocyclic or polycyclic aromatic cycle having 6 to 20 carbon atoms; or a substituted or unsubstituted monocyclic or polycyclic heterocycle having 2 to 20 carbon atoms.

According to another exemplary embodiment of the present specification, Cy1 and Cy2 are the same as or different from each other, and are each independently a substituted or unsubstituted monocyclic or polycyclic aromatic cycle having 6 to 10 carbon atoms; or a substituted or unsubstituted monocyclic or polycyclic heterocycle having 2 to 10 carbon atoms.

According to another exemplary embodiment of the present specification, Cy1 and Cy2 are the same as or different from each other, and are each independently a substituted or unsubstituted benzene cycle; or a substituted or unsubstituted naphthalene cycle.

According to another exemplary embodiment of the present specification, Cy1 and Cy2 are the same as or different from each other, and are each independently a benzene cycle; or a naphthalene cycle.

According to one exemplary embodiment of the present specification, at least one of Cy1 and Cy2 is a substituted or unsubstituted benzene cycle.

According to the exemplary embodiment of the present specification, the compound represented by Chemical Formula 1 is represented by any one of the following Chemical Formulas 1-1 to 1-4.

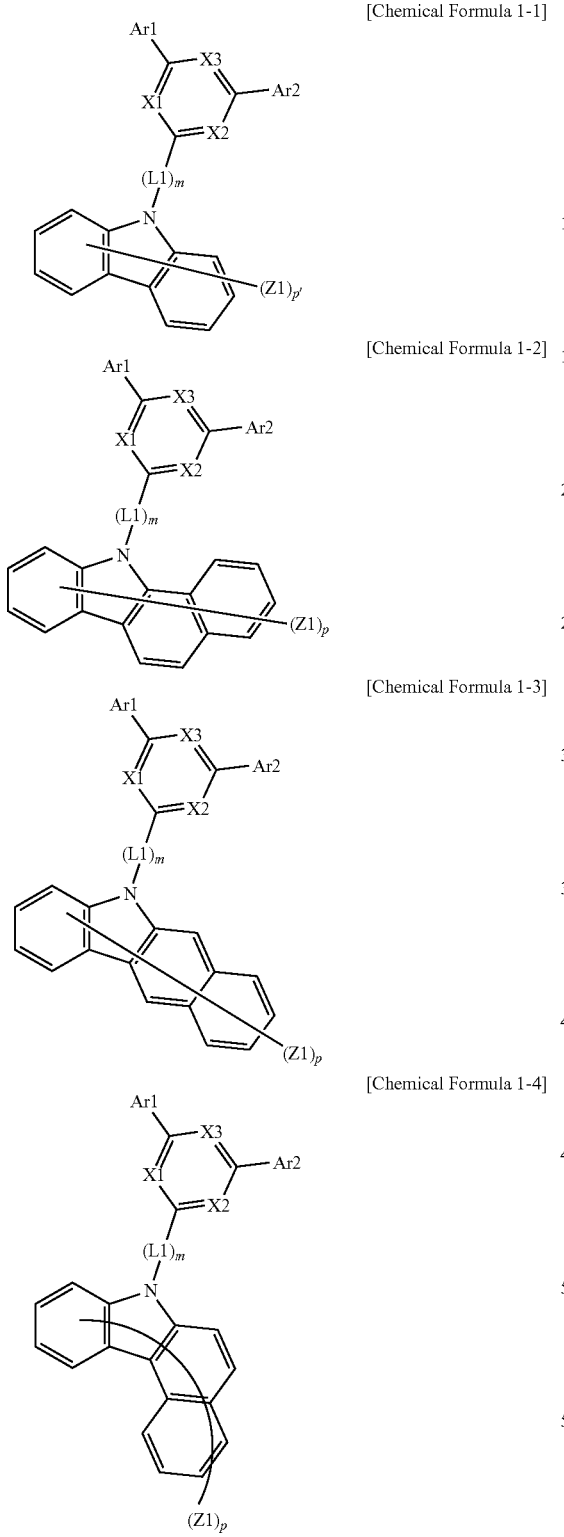

[Chemical Formula 1-1]

[Chemical Formula 1-2]

[Chemical Formula 1-3]

[Chemical Formula 1-4]

In Chemical Formulas 1-1 to 1-4,
X1 to X3, L1, m, Ar1, and Ar2 are the same as those defined in Chemical Formula 1,
Z1 is deuterium,
p' is an integer of 0 to 8, and
p is an integer of 0 to 10.

According to the exemplary embodiment of the present specification, Chemical Formula 1 is represented by the following Chemical Formula 1-5.

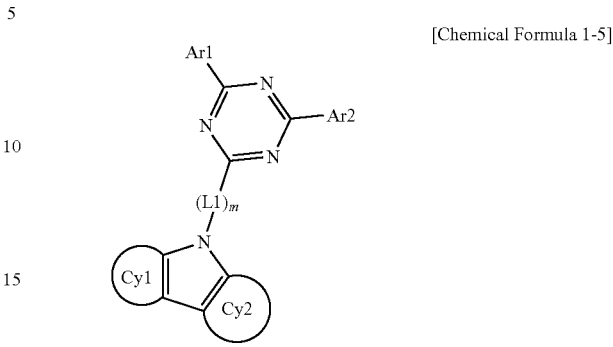

[Chemical Formula 1-5]

In Chemical Formula 1-5, Cy1, Cy2, L1, m, Ar1, and Ar2 are the same as defined in Chemical Formula 1 according to the aforementioned exemplary embodiment.

According to the exemplary embodiment of the present specification, in Chemical Formula 1, L1 is a substituted or unsubstituted monocyclic or polycyclic arylene group having 6 to 30 carbon atoms.

According to the exemplary embodiment of the present specification, in Chemical Formula 1, L1 is a substituted or unsubstituted monocyclic arylene group having 6 to 30 carbon atoms. In this case, L1 may help an interaction between a structure including Cy1 and Cy2 and a structure including X1 to X3 to help the bipolar type to be stably maintained.

According to another exemplary embodiment of the present specification, L1 is a substituted or unsubstituted monocyclic arylene group having 6 to 24 carbon atoms.

According to another exemplary embodiment of the present specification, L1 is a substituted or unsubstituted phenylene group; or a substituted or unsubstituted biphenylene group.

According to another exemplary embodiment of the present specification, L1 is a substituted or unsubstituted phenylene group; a substituted or unsubstituted biphenylene group; a substituted or unsubstituted terphenylene group; or a substituted or unsubstituted quaterphenylene group.

According to one exemplary embodiment of the present specification, m is 1.
According to another exemplary embodiment, m is 2.
According to another exemplary embodiment, m is 3.
According to another exemplary embodiment, m is 4.
According to another exemplary embodiment of the present specification, L1 is a phenylene group; a biphenylene group; a terphenylene group; or a quaterphenylene group.

According to another exemplary embodiment of the present specification, L1 is a phenylene group; or a biphenylene group, and m is 1 or 2, and in the case where m is 2, L1 s are the same as or different from each other.

In one exemplary embodiment of the present specification, $(L1)_m$ is represented by the following Chemical Formula 3.

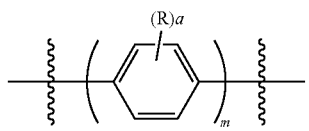

[Chemical Formula 3]

In Chemical Formula 3,

R is a substituent group, a is an integer of 1 to 4, in the case where a is an integer of 2 to 4, 2 to 4 Rs are the same as or different from each other, m is an integer of 1 to 4, and in the case where m is an integer of 2 to 4, 2 to 4 structures in brackets are the same as or different from each other.

The substituent group R may be selected from the aforementioned examples of the substituent group.

According to the exemplary embodiment of the present specification, in the case where $(L1)_m$ is Chemical Formula 3, a cycle including Cy1 and Cy2 and a cycle including X1 to X3 may be connected in a linear form to structurally connect the p type and the n type and thus increase an interaction thereof, thereby stably serving as the bipolar type.

According to the exemplary embodiment of the present specification, the compound represented by Chemical Formula 1 is represented by any one of the following Chemical Formulas 1-6 to 1-9.

[Chemical Formula 1-6]

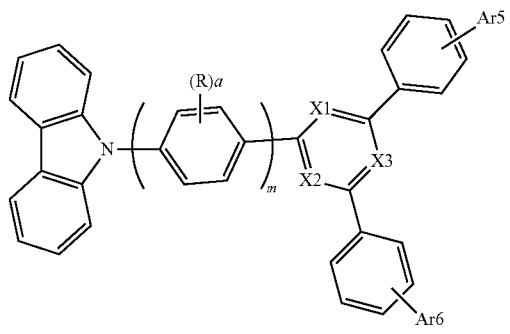

[Chemical Formula 1-7]

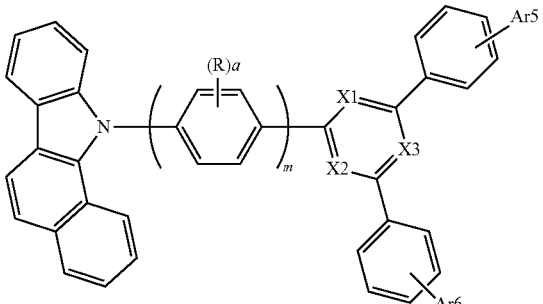

[Chemical Formula 1-8]

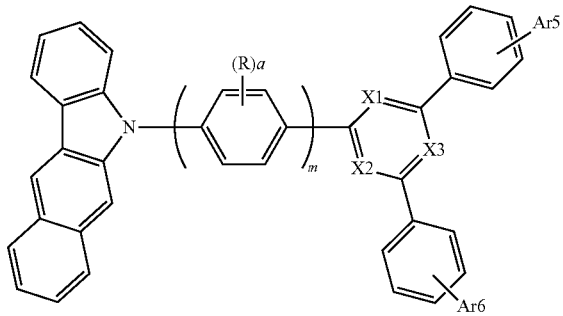

[Chemical Formula 1-9]

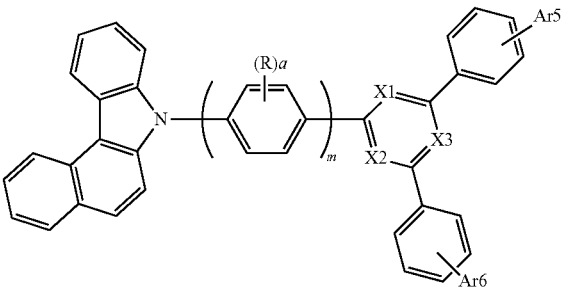

In Chemical Formulas 1-6 to 1-9,

X1 to X3 are the same as or different from each other, and are each independently N or CH, at least one of X1 to X3 is N, Ar5 and Ar6 are the same as or different from each other, and are each independently hydrogen; deuterium; a substituted or unsubstituted alkyl group having 1 to 20 carbon atoms; a substituted or unsubstituted monocyclic or polycyclic aryl group having 6 to 30 carbon atoms; or a substituted or unsubstituted monocyclic or polycyclic heteroaryl group having 2 to 30 carbon atoms, or are bonded to a phenyl group to form a cycle, R is a substituent group, a is an integer of 1 to 4, in the case where a is an integer of 2 to 4, 2 to 4 Rs are the same as or different from each other, m is an integer of 1 to 4, and in the case where m is an integer of 2 to 4, 2 to 4 structures in brackets are the same as or different from each other.

According to another exemplary embodiment of the present specification, Ar5 and Ar6 are the same as or different from each other, and are each independently hydrogen; deuterium; a substituted or unsubstituted alkyl group having 1 to 10 carbon atoms; a substituted or unsubstituted monocyclic or polycyclic aryl group having 6 to 20 carbon atoms; or a substituted or unsubstituted monocyclic or polycyclic heteroaryl group having 2 to 20 carbon atoms, or are bonded to a phenyl group to form a cycle.

According to another exemplary embodiment of the present specification, Ar5 and Ar6 are the same as or different from each other, and are each independently hydrogen; deuterium; a substituted or unsubstituted alkyl group having 1 to 5 carbon atoms; a substituted or unsubstituted monocyclic or polycyclic aryl group having 6 to 10 carbon atoms; or a substituted or unsubstituted monocyclic or polycyclic heteroaryl group having 2 to 10 carbon atoms, or are bonded to a phenyl group to form a cycle.

Formation of the cycle by bonding to the phenyl group means formation of a condensation cycle by bonding the phenyl group and Ar5 or Ar6, and in this case, the structure including X1 to X3 may be substituted by a polycycle. In the present specification, the cycle may be an aliphatic hydrocarbon cycle, an aromatic hydrocarbon cycle, an aliphatic heterocycle, an aromatic heterocycle, or the like.

According to another exemplary embodiment of the present specification, Ar5 and Ar6 are the same as or different from each other, and are each independently hydrogen; a substituted or unsubstituted methyl group; a substituted or unsubstituted phenyl group; a substituted or unsubstituted biphenyl group; or a substituted or unsubstituted naphthyl group, or are bonded to a phenyl group to form a substituted or unsubstituted naphthalene cycle, a substituted or unsubstituted triphenylene cycle, a substituted or unsubstituted fluorene cycle; or a substituted or unsubstituted phenanthrene cycle.

According to another exemplary embodiment of the present specification, Ar5 and Ar6 are the same as or different from each other, and are each independently a methyl group; a triphenylmethyl group; a phenyl group; a naphthyl group; or a biphenyl group, or are bonded to a phenyl group to form a naphthalene cycle; a triphenylene cycle; a fluorene cycle substituted by a phenyl group; or a phenanthrene cycle.

According to the exemplary embodiment of the present specification, in Chemical Formula 1, Ar1 and Ar2 are the same as or different from each other, and are each independently selected from the group consisting of a substituted or unsubstituted monocyclic or polycyclic aryl group having 6 to 20 carbon atoms; and a substituted or unsubstituted monocyclic or polycyclic heteroaryl group having 2 to 20 carbon atoms.

According to another exemplary embodiment of the present specification, Ar1 and Ar2 are the same as or different from each other, and are each independently a substituted or unsubstituted phenyl group; a substituted or unsubstituted biphenyl group; a substituted or unsubstituted terphenyl group; a substituted or unsubstituted naphthyl group; a substituted or unsubstituted triphenylenyl group; a substituted or unsubstituted fluorenyl group; or a substituted or unsubstituted phenanthrenyl group.

According to another exemplary embodiment of the present specification, Ar1 and Ar2 are the same as or different from each other, and are each independently a phenyl group; a biphenyl group; a terphenyl group; a naphthyl group; a triphenylenyl group; a fluorenyl group; or a phenanthrenyl group, and the phenyl group, the biphenyl group, the terphenyl group, the naphthyl group, the triphenylenyl group, the fluorenyl group, and the threnyl group are unsubstituted or substituted by one or two or more substituent groups selected from the group consisting of a substituted or unsubstituted alkyl group and a substituted or unsubstituted aryl group.

According to another exemplary embodiment of the present specification, Ar1 and Ar2 are the same as or different from each other, and are each independently selected from the group consisting of a phenyl group; a phenyl group substituted by a methyl group; a phenyl group substituted by a triphenylmethyl group; a phenyl group substituted by a naphthyl group; a phenyl group substituted by a phenyl group; a phenyl group substituted by a terphenyl group; a biphenyl group; a biphenyl group substituted by a phenyl group; a naphthyl group; a triphenylenyl group; a fluorenyl group substituted by a phenyl group; and a phenanthrenyl group.

According to the exemplary embodiment of the present specification, Ar1 and Ar2 are the same as or different from each other, and are each independently any one of the following substituent groups.

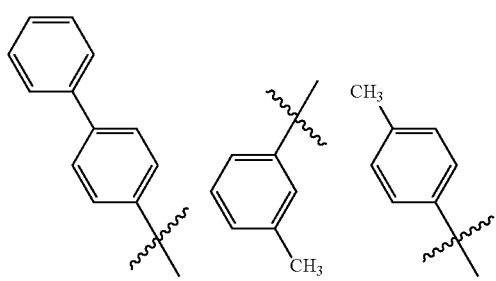

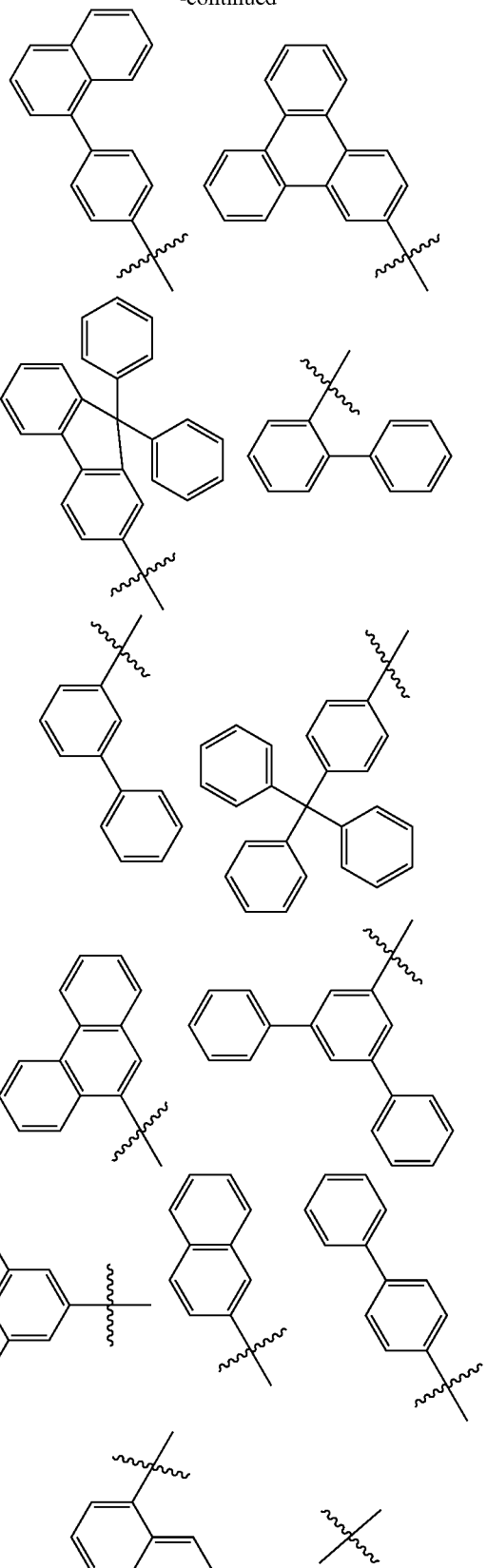

is a portion connected to X1 to X3 of Chemical Formula 1.

According to the exemplary embodiment of the present specification, p' is 0.

According to one exemplary embodiment, p is 0.

According to the exemplary embodiment of the present specification, the compound represented by Chemical Formula 1 is represented by any one of the following compounds.

According to one exemplary embodiment, the compound represented by Chemical Formula 1-1 is represented by any one of the following Chemical Formulas 1-1-1 to 1-1-37.

According to another exemplary embodiment, the compound represented by Chemical Formula 1-2 is represented by any one of the following Chemical Formulas 1-2-1 to 1-2-8.

According to another exemplary embodiment, the compound represented by Chemical Formula 1-3 is represented by any one of the following Chemical Formulas 1-3-1 to 1-3-8.

According to another exemplary embodiment, the compound represented by Chemical Formula 1-4 is represented by any one of the following Chemical Formulas 1-4-1 to 1-4-8.

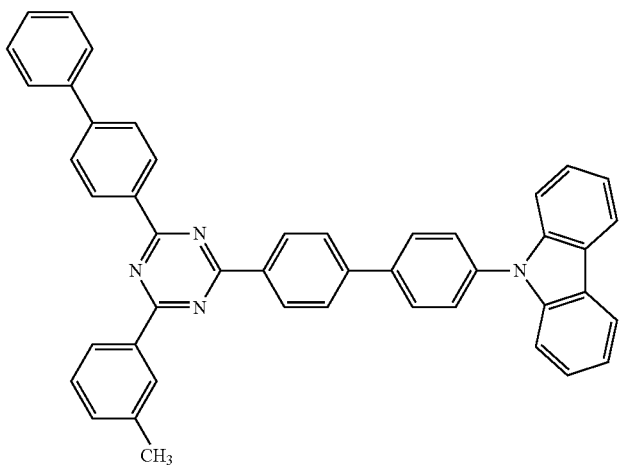

Chemical Formula 1-1-1

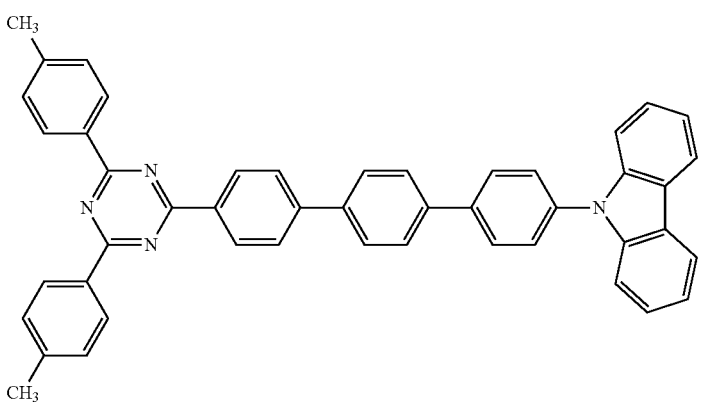

Chemical Formula 1-1-2

Chemical Formula 1-1-3
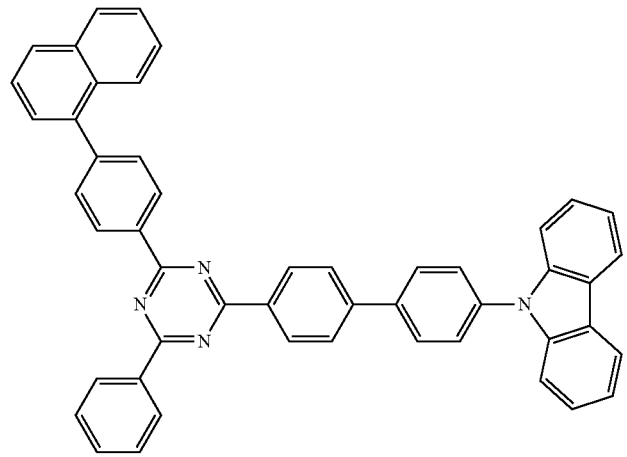
Chemical Formula 1-1-4
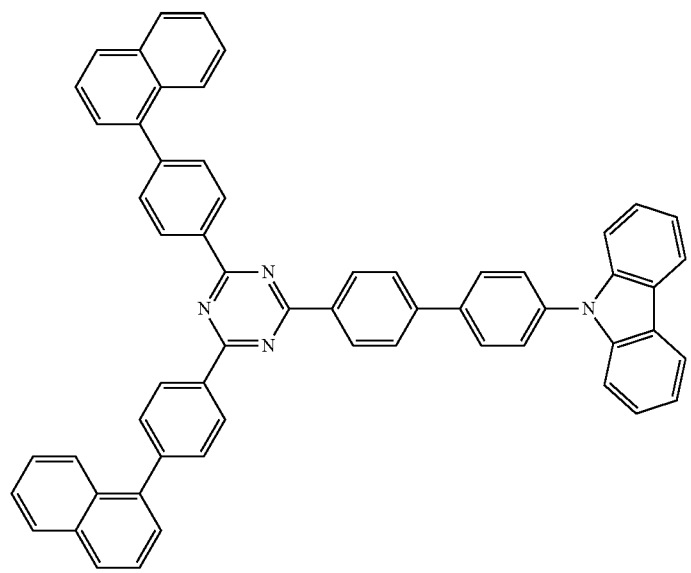
Chemical Formula 1-1-5
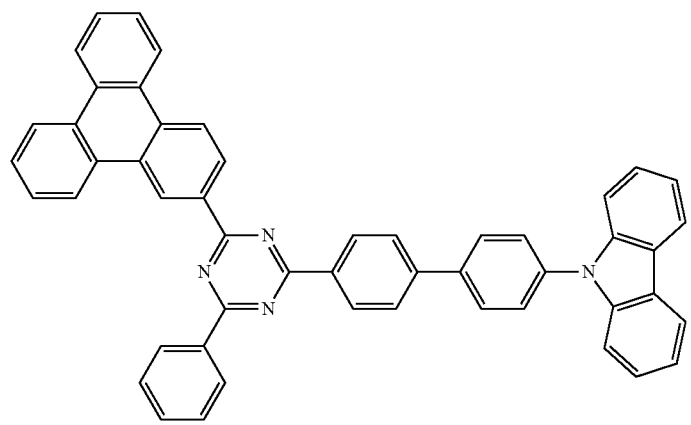

Chemical Formula 1-1-6
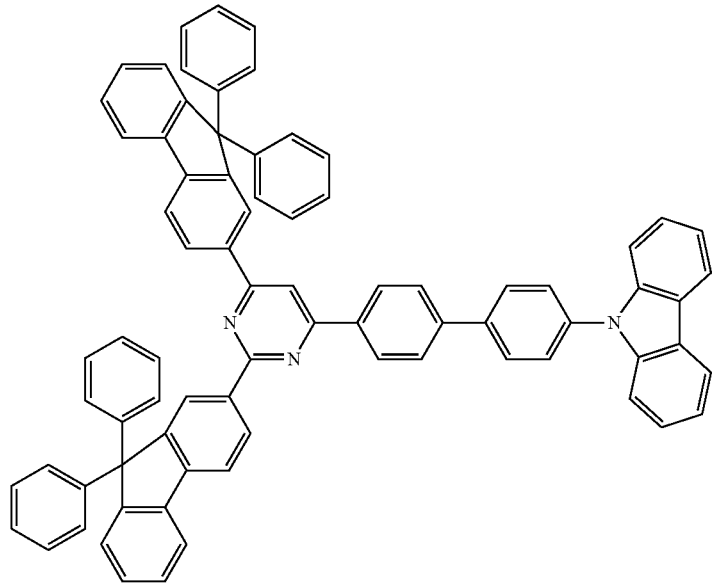
Chemical Formula 1-1-7
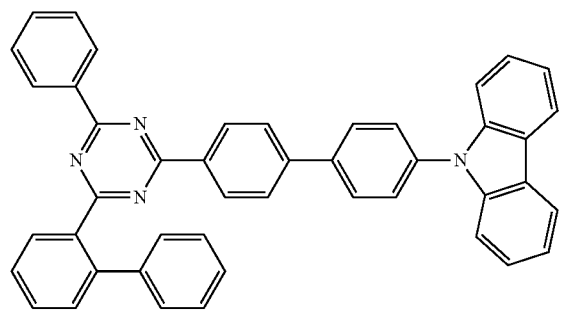
Chemical Formula 1-1-8
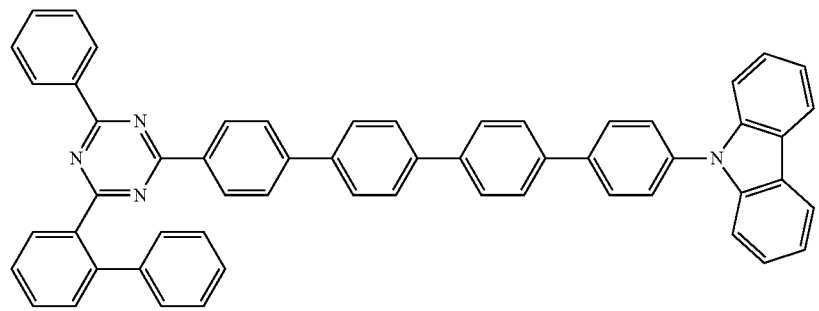
Chemical Formula 1-1-9
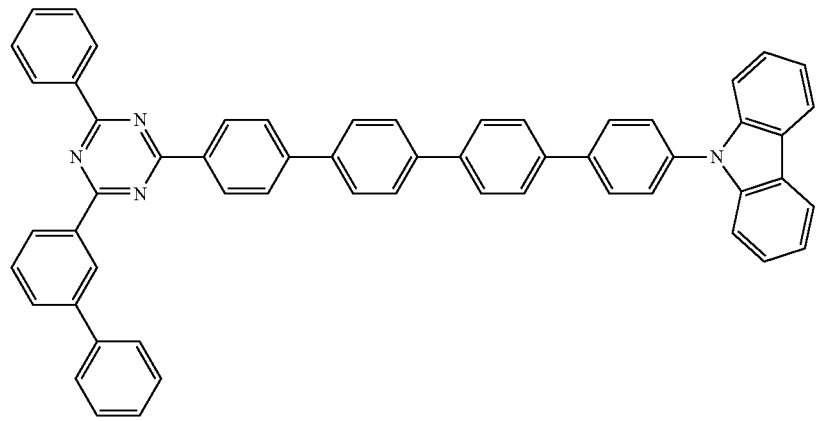

Chemical Formula 1-1-10
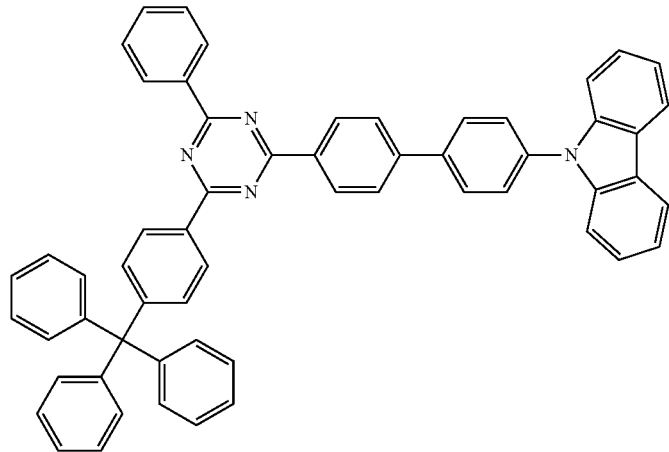
Chemical Formula 1-1-11
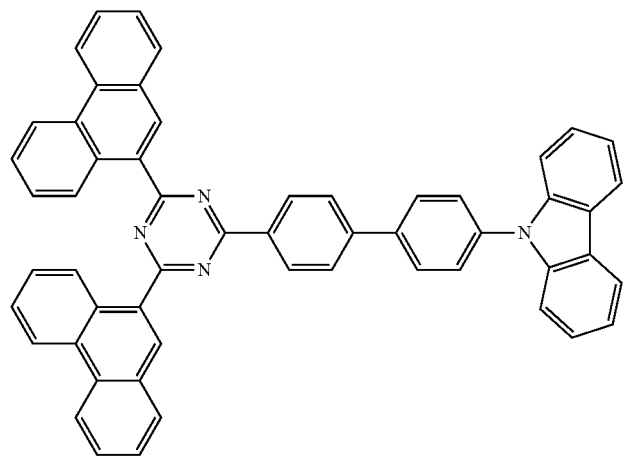
Chemical Formula 1-1-12
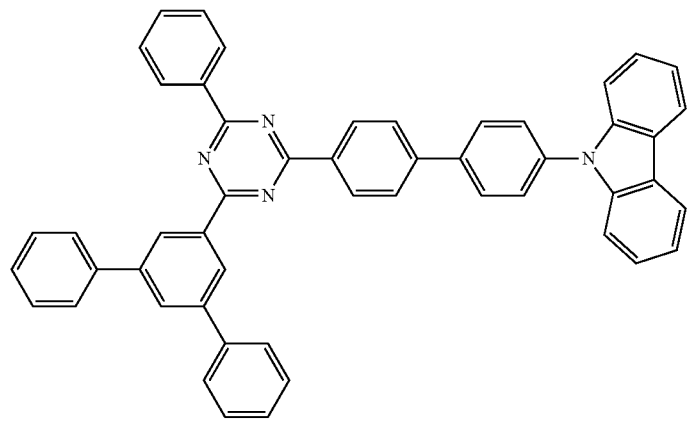

Chemical Formula 1-1-13
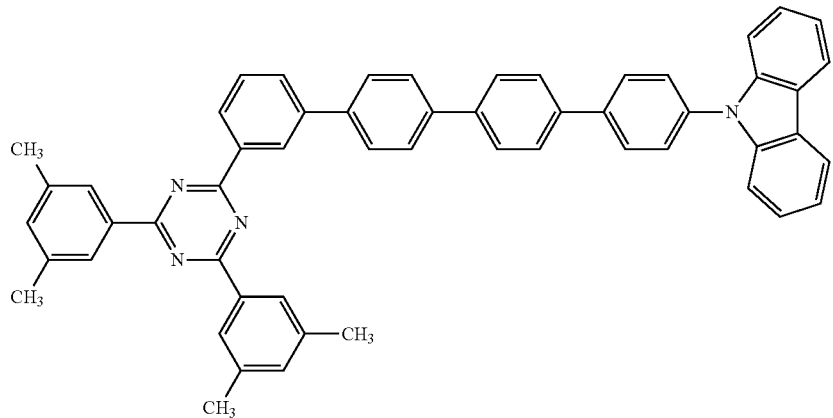
Chemical Formula 1-1-14
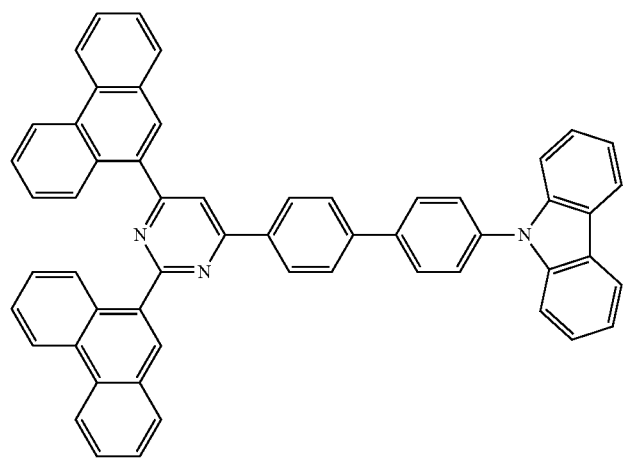
Chemical Formula 1-1-15
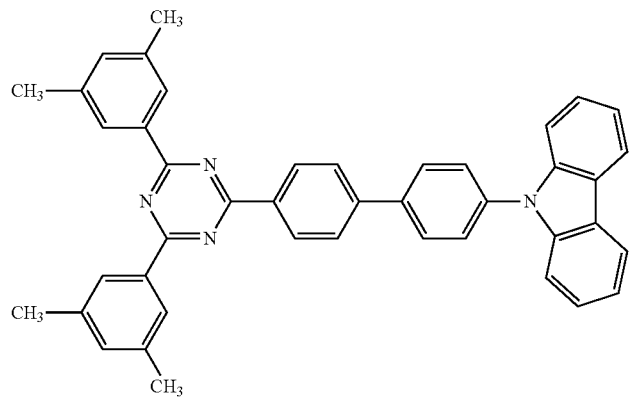

Chemical Formula 1-1-16
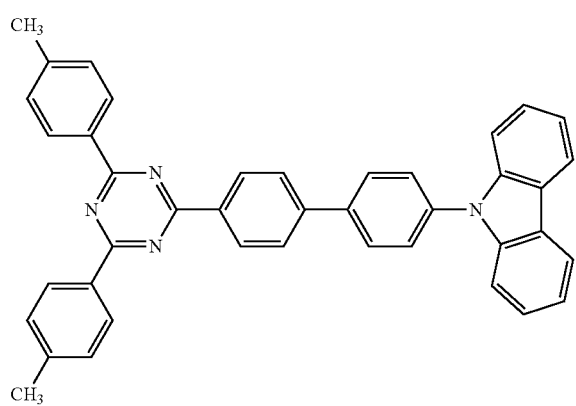
Chemical Formula 1-1-17
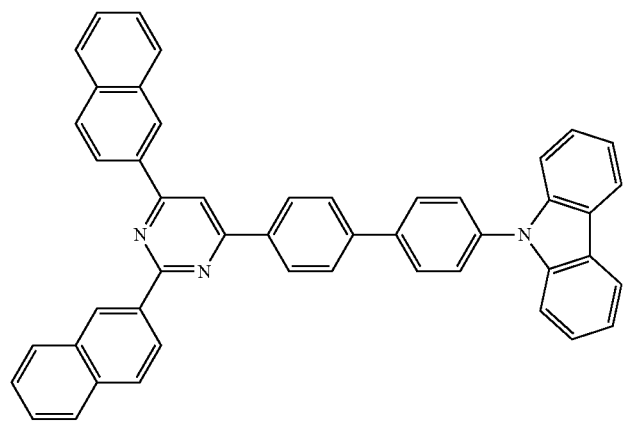
Chemical Formula 1-1-18
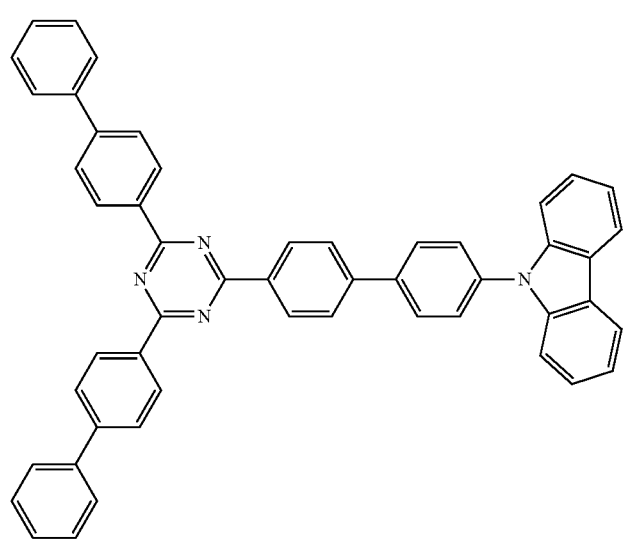
Chemical Formula 1-1-19
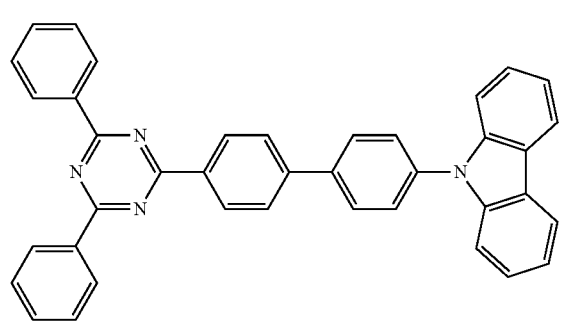

-continued
Chemical Formula 1-1-20
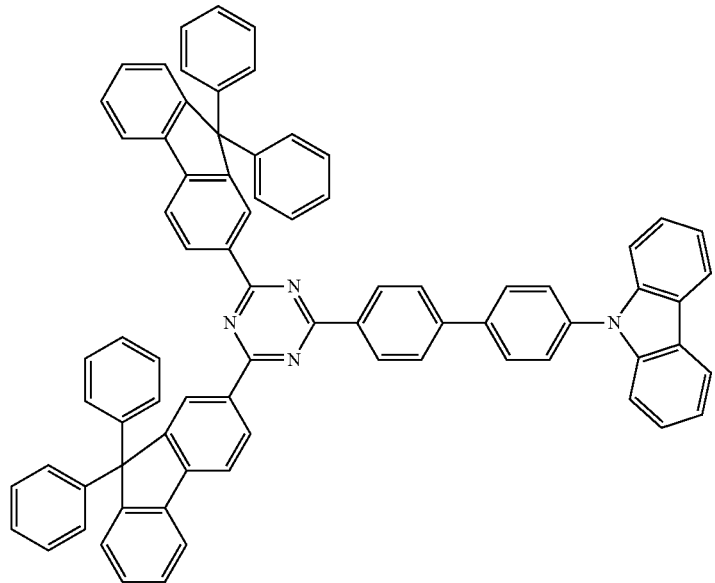
Chemical Formula 1-1-21
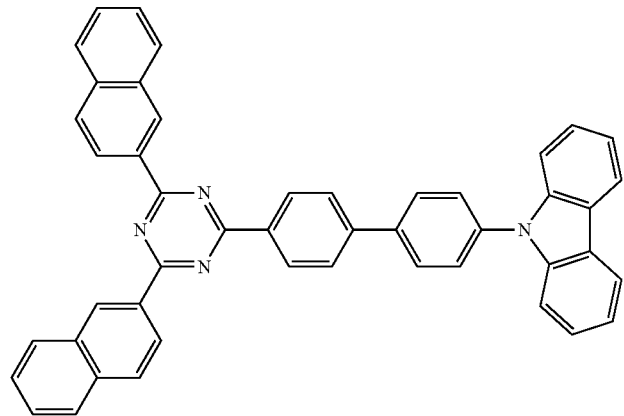
Chemical Formula 1-1-22
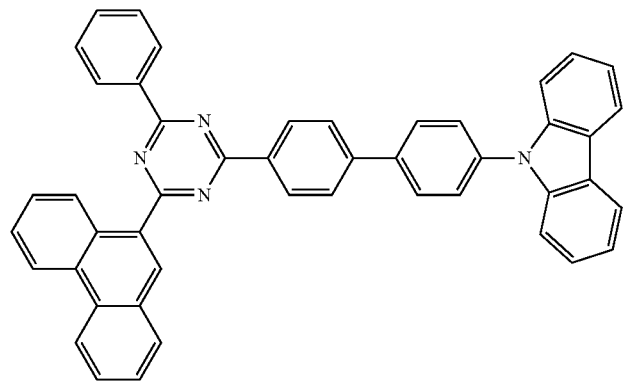

-continued
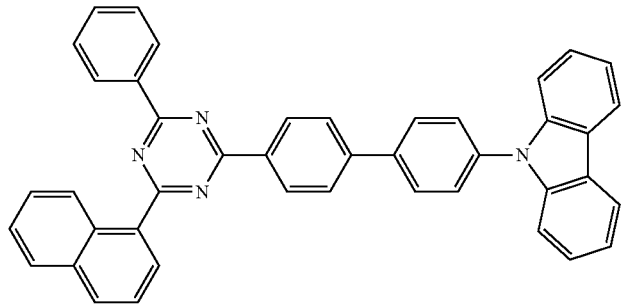
Chemical Formula 1-1-23
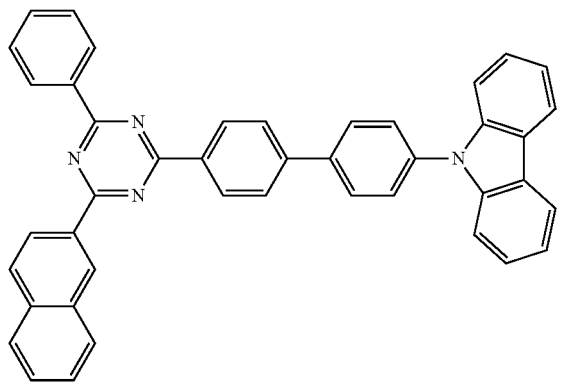
Chemical Formula 1-1-24
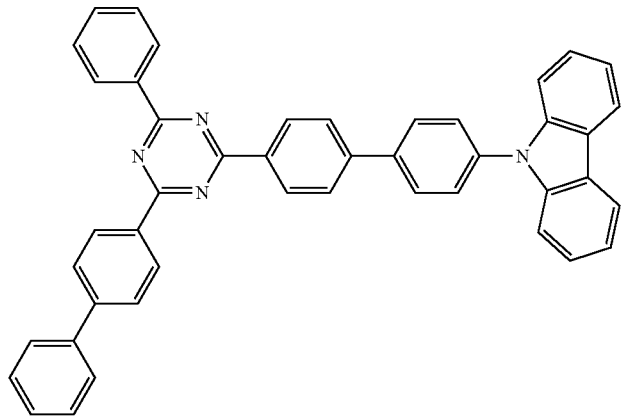
Chemical Formula 1-1-25
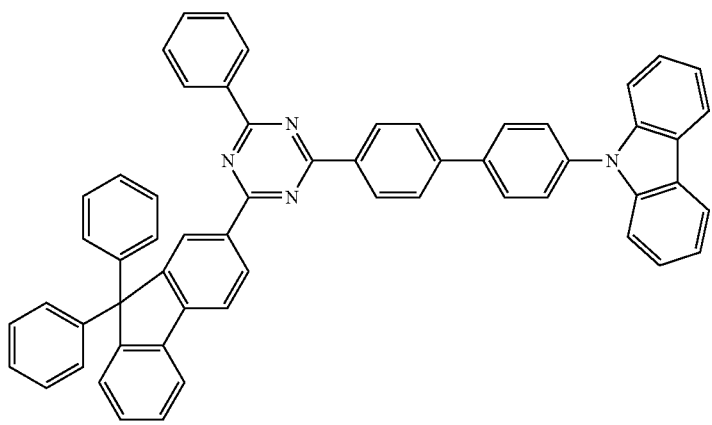
Chemical Formula 1-1-26

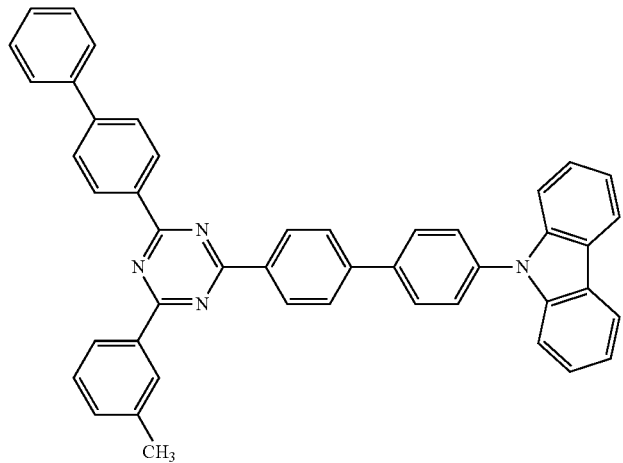
Chemical Formula 1-1-27
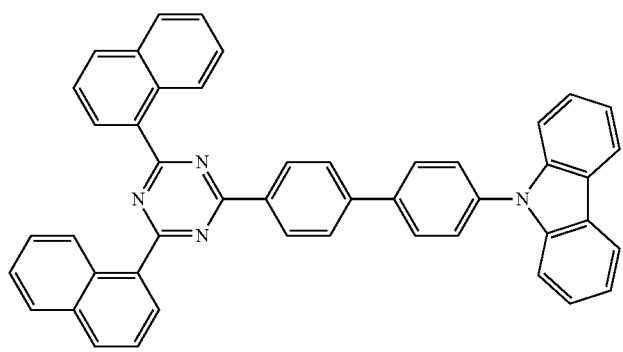
Chemical Formula 1-1-28
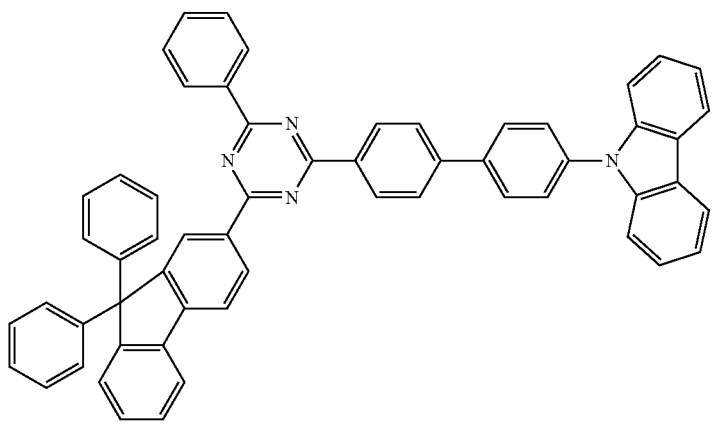
Chemical Formula 1-1-29

Chemical Formula 1-1-30
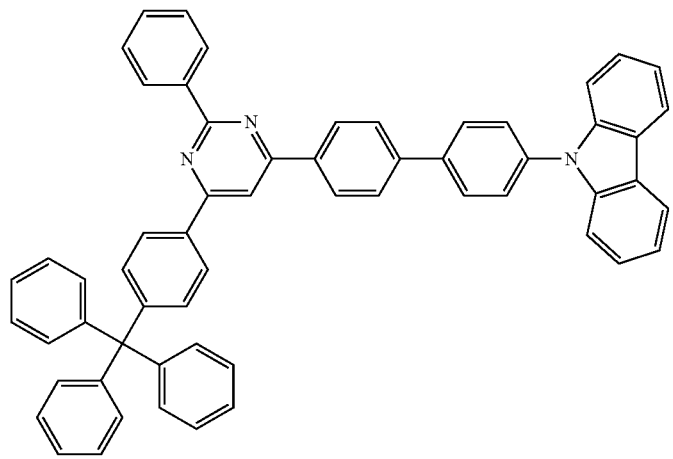
Chemical Formula 1-1-31
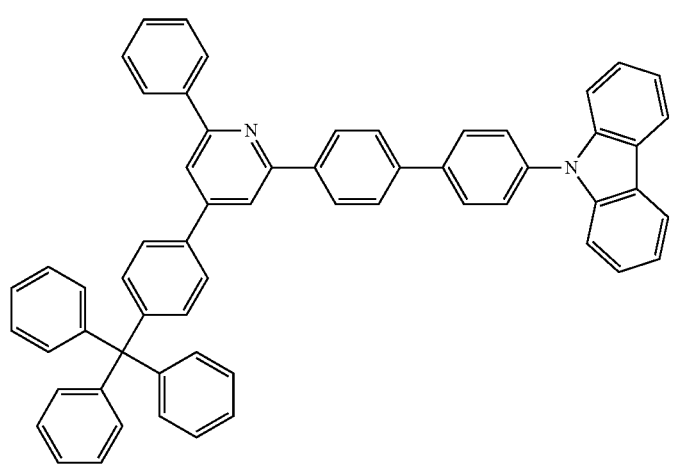
Chemical Formula 1-1-32
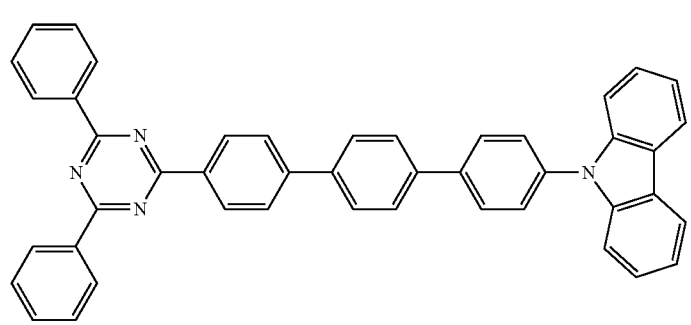
Chemical Formula 1-1-33
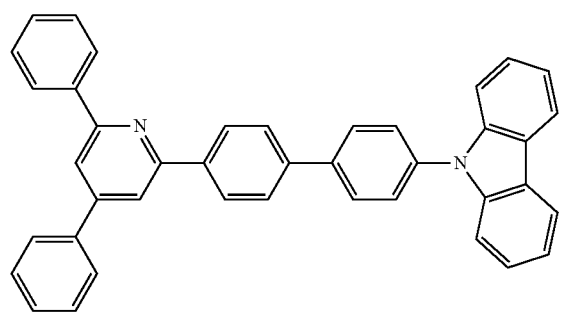

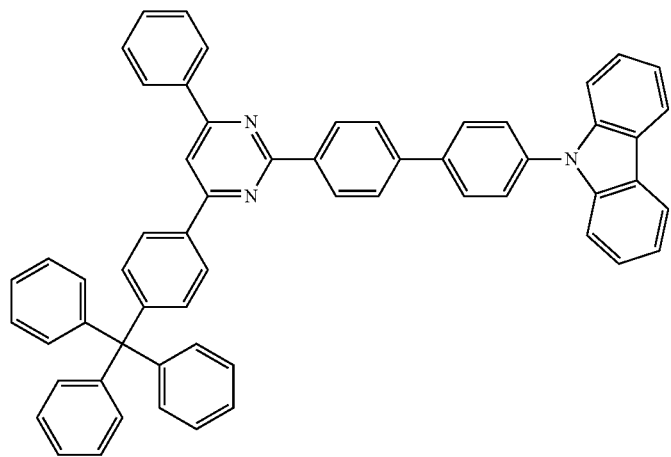
Chemical Formula 1-1-34
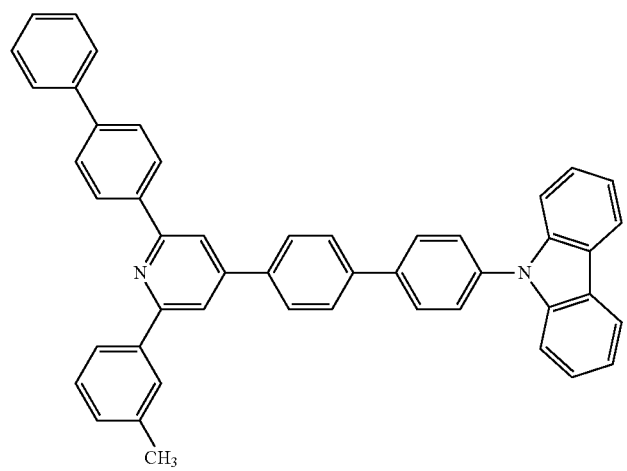
Chemical Formula 1-1-35
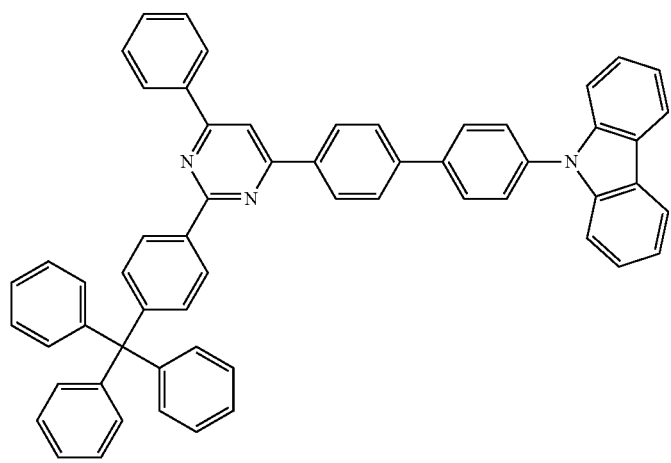
Chemical Formula 1-1-36

Chemical Formula 1-1-37
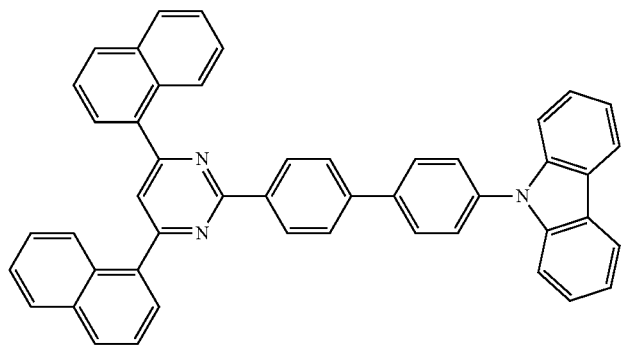
Chemical Formula 1-2-1
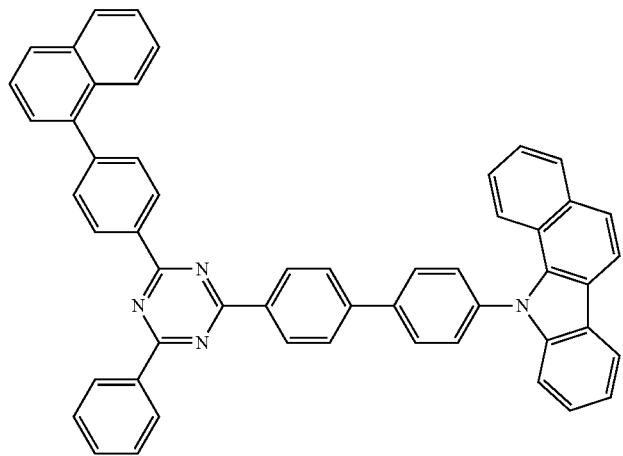
Chemical Formula 1-2-2
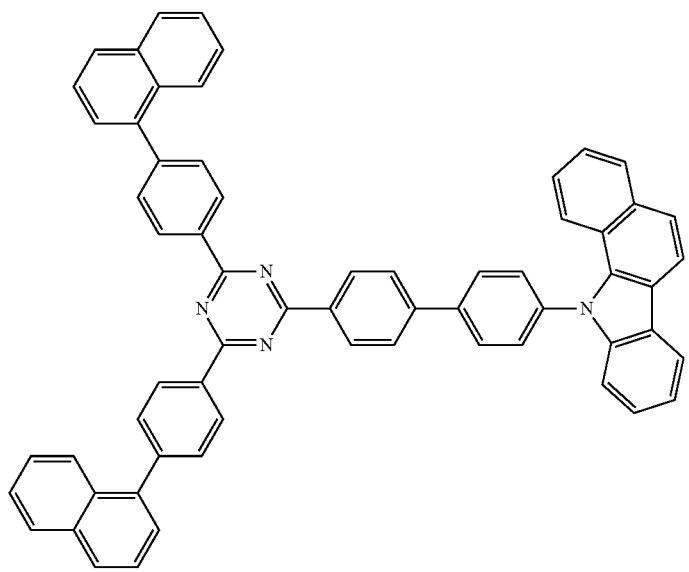

Chemical Formula 1-2-3
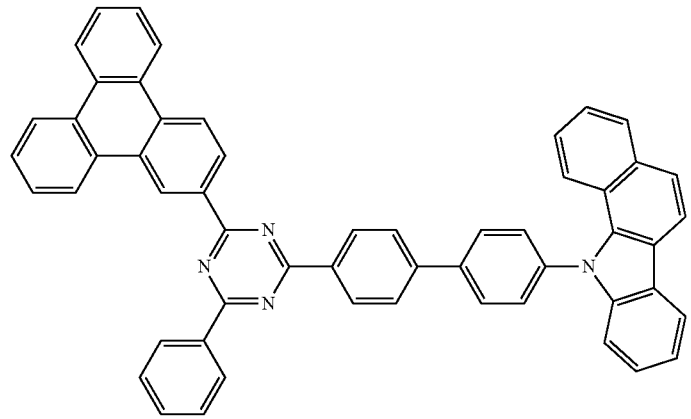
Chemical Formula 1-2-4
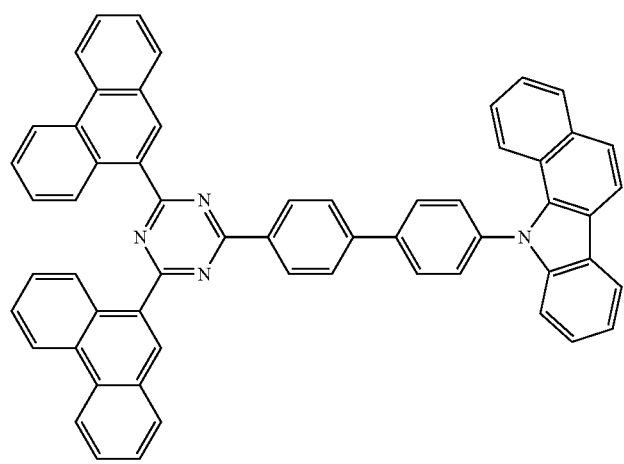
Chemical Formula 1-2-5
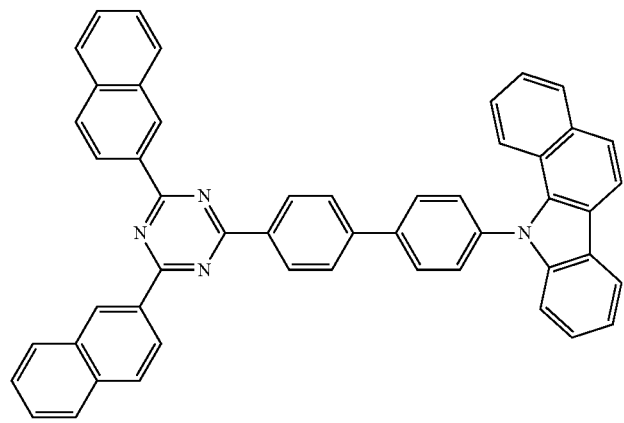

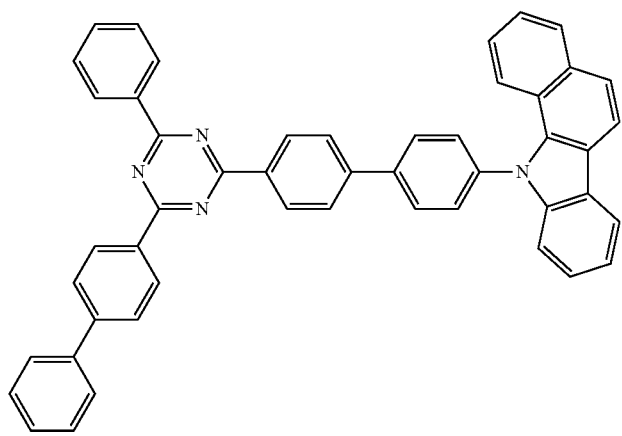
Chemical Formula 1-2-6
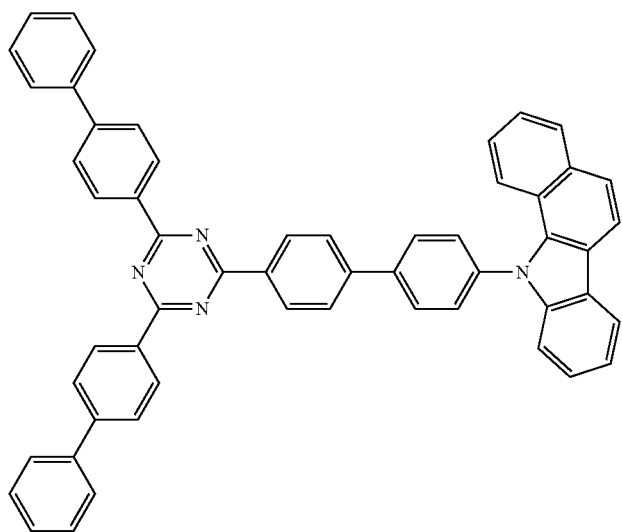
Chemical Formula 1-2-7
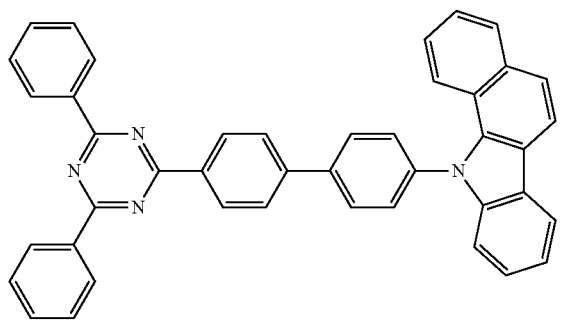
Chemical Formula 1-2-8

Chemical Formula 1-3-1
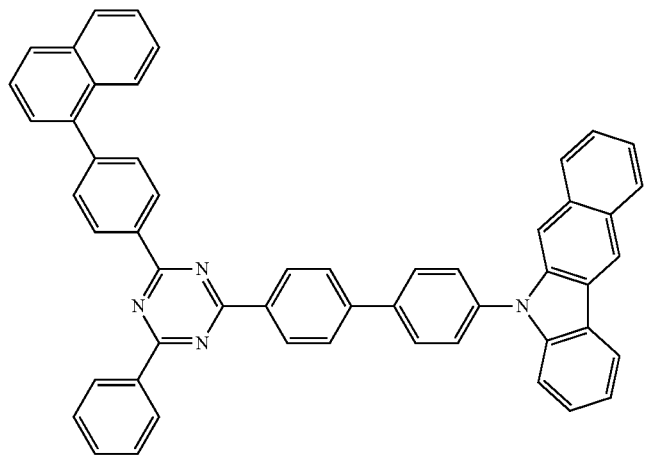
Chemical Formula 1-3-2
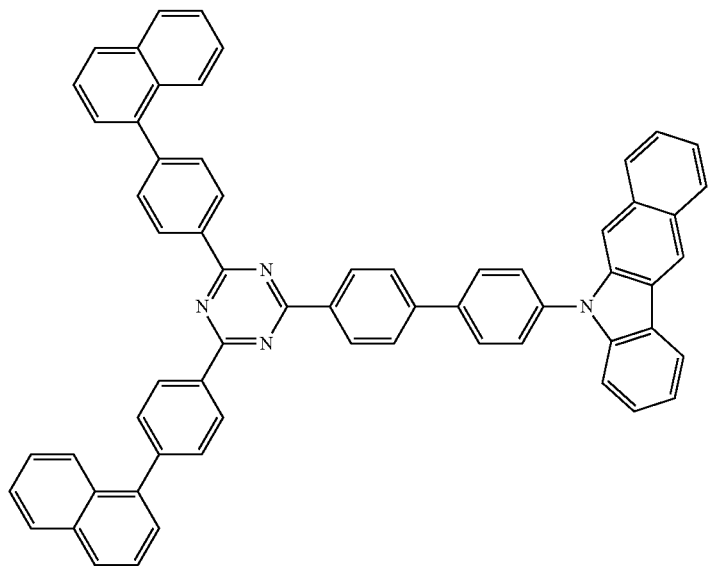
Chemical Formula 1-3-3
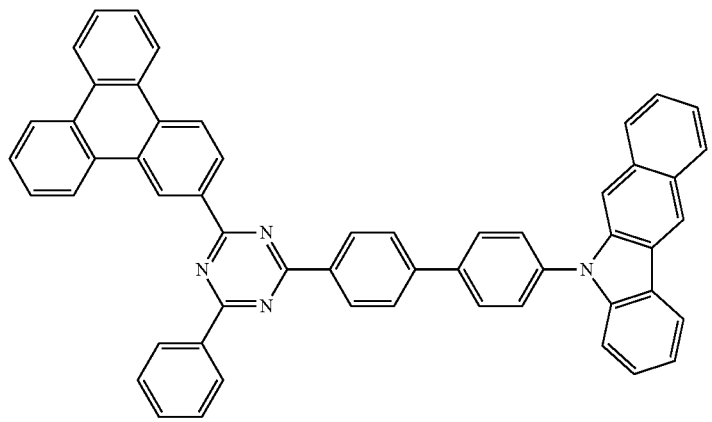

Chemical Formula 1-3-4
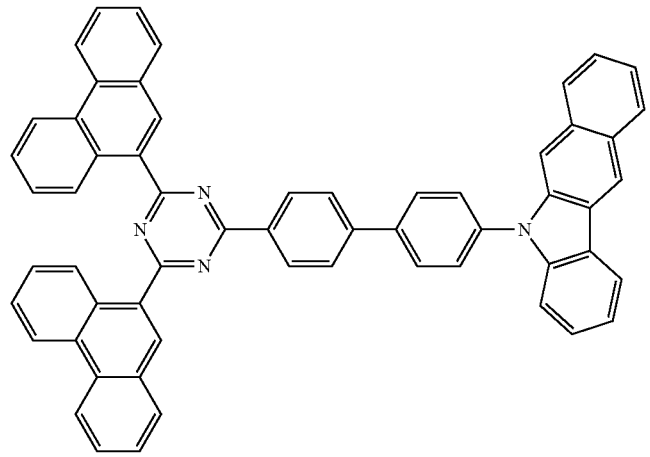
Chemical Formula 1-3-5
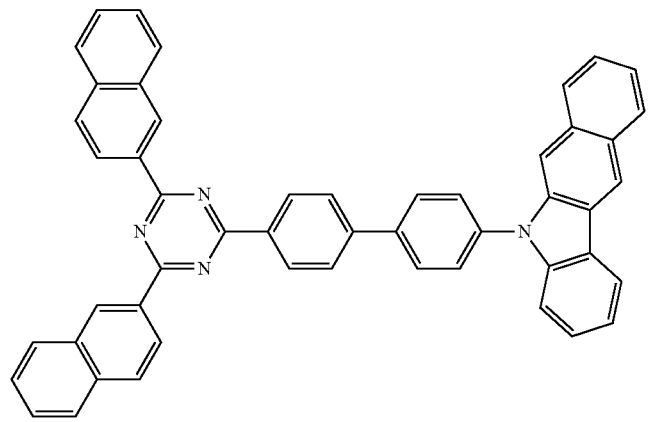
Chemical Formula 1-3-6
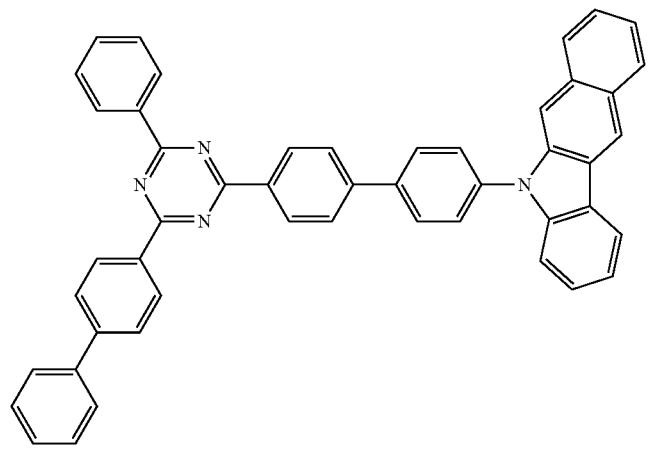

Chemical Formula 1-3-7
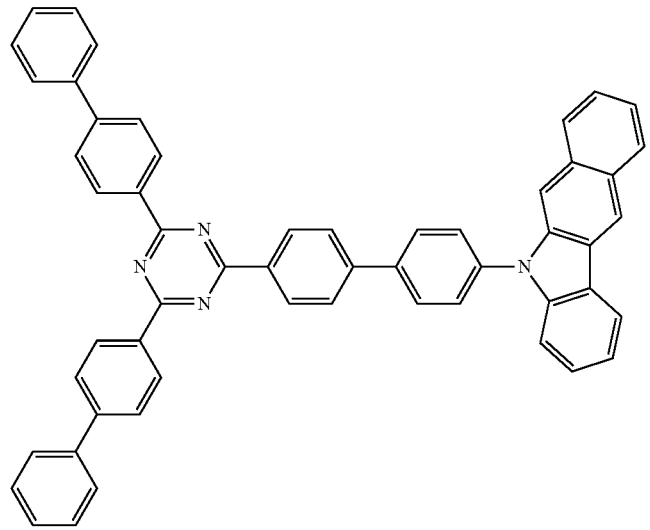
Chemical Formula 1-3-8
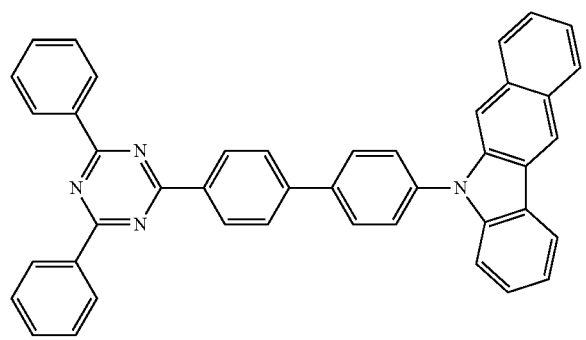
Chemical Formula 1-4-1
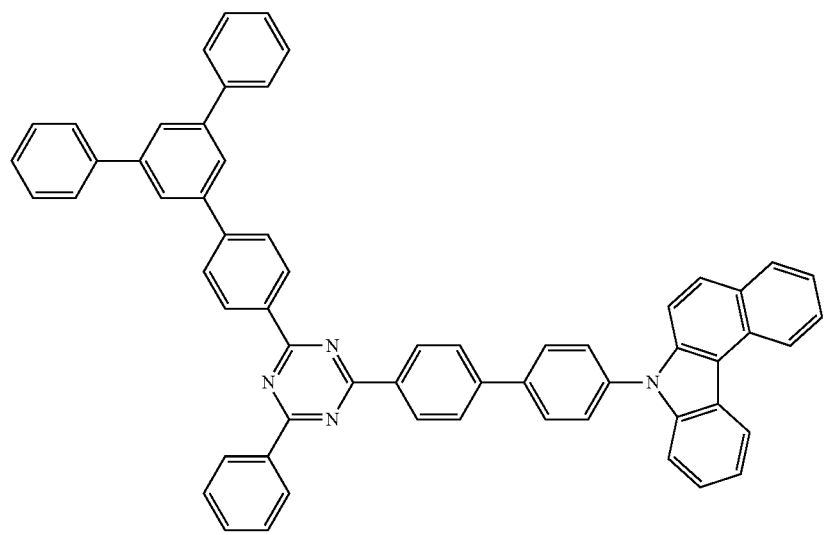

Chemical Formula 1-4-2
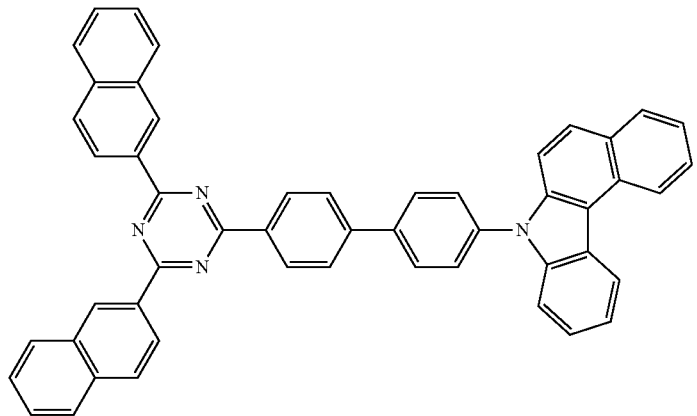
Chemical Formula 1-4-3
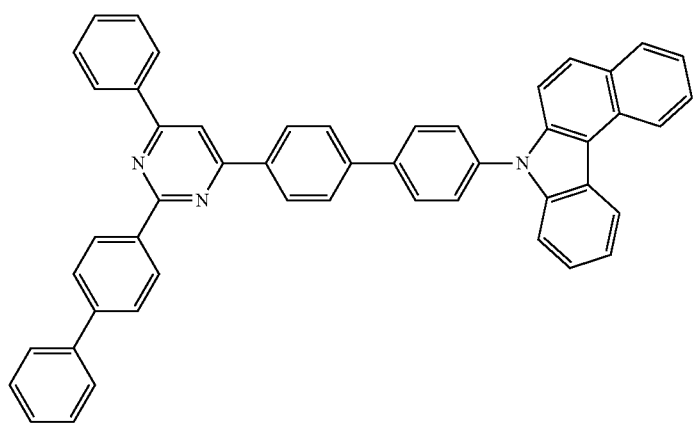
Chemical Formula 1-4-4
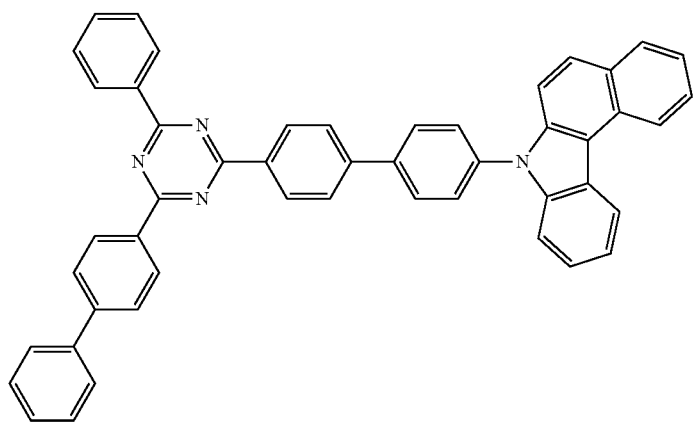

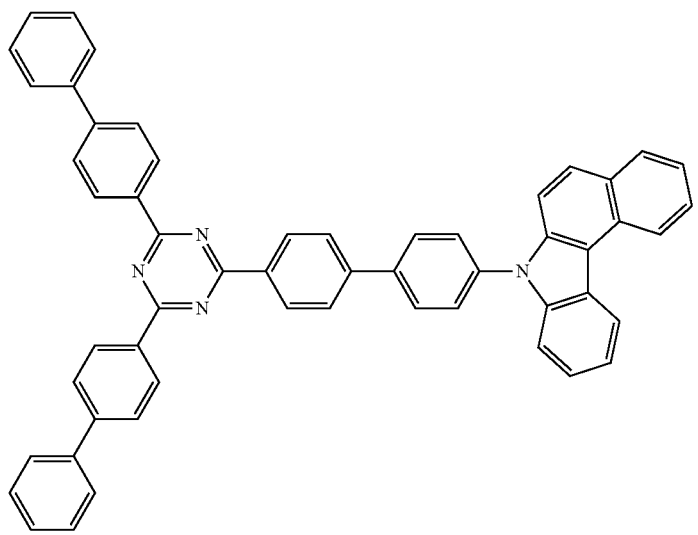
Chemical Formula 1-4-5
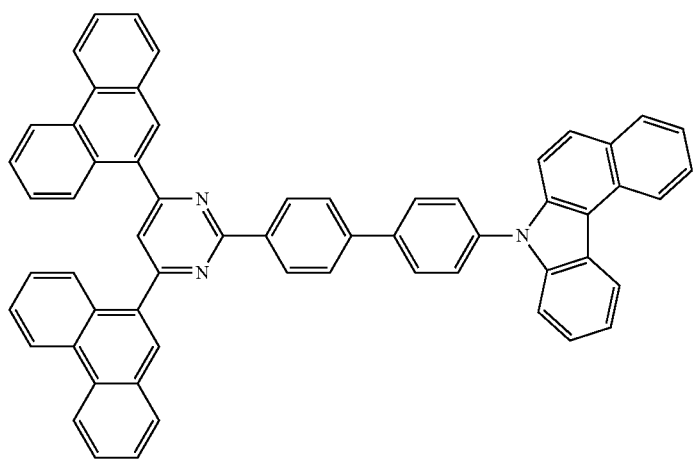
Chemical Formula 1-4-6
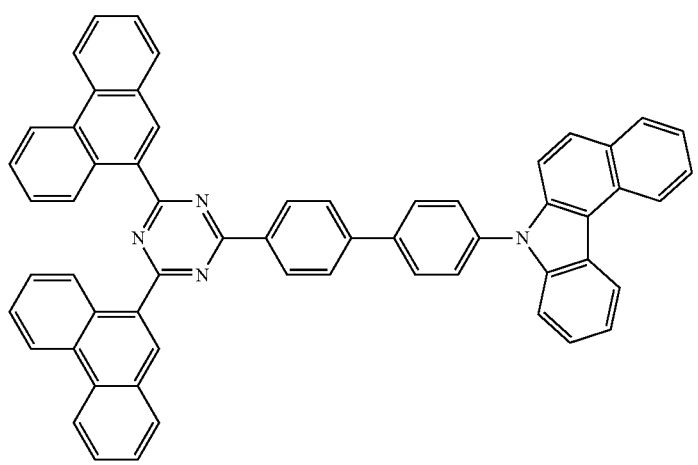
Chemical Formula 1-4-7

Chemical Formula 1-4-8

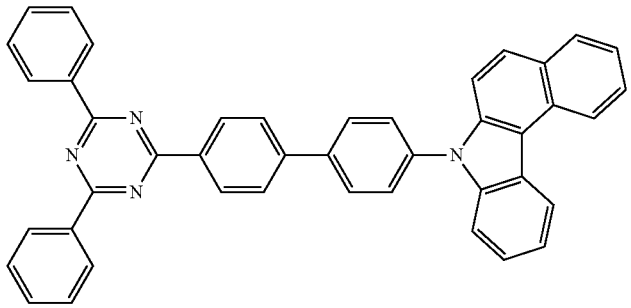

According to the exemplary embodiment of the present specification, in Chemical Formula 2, Ar3 and Ar4 are the same as or different from each other, and are each independently a substituted or unsubstituted monocyclic or polycyclic aryl group having 6 to 25 carbon atoms; or a substituted or unsubstituted monocyclic or polycyclic heteroaryl group having 2 to 25 carbon atoms, or are bonded to each other to form a substituted or unsubstituted cycle.

According to another exemplary embodiment of the present specification, Ar3 and Ar4 are the same as or different from each other, and are each independently a substituted or unsubstituted phenyl group; a substituted or unsubstituted biphenyl group; a substituted or unsubstituted fluorenyl group; a substituted or unsubstituted spirobifluorenyl group; or a substituted or unsubstituted dibenzofuran group, or are bonded to each other to form a substituted or unsubstituted dihydroacridine structure.

According to another exemplary embodiment of the present specification, Ar3 and Ar4 are the same as or different from each other, and are each independently a phenyl group; a biphenyl group; a spirobifluorenyl group; a phenyl group substituted by a phenyl group; a fluorenyl group substituted by a methyl group; or a dibenzofuran group, or are bonded to each other to form a dihydroacridine structure substituted by a substituent group selected from the group consisting of a phenyl group and an alkyl group.

According to the exemplary embodiment of the present specification, in Chemical Formula 2, Ar3 and Ar4 may be bonded to each other to form substituted or unsubstituted 9,10-dihydroacridine.

According to another exemplary embodiment of the present specification, Ar3 and Ar4 may be bonded to each other to form 9,10-dihydroacridine substituted by a methyl group; or 9,10-dihydroacridine substituted by a phenyl group and a methyl group.

According to the exemplary embodiment of the present specification, in Chemical Formula 2, L2 is a substituted or unsubstituted monocyclic or polycyclic arylene group having 6 to 20 carbon atoms.

According to another exemplary embodiment of the present specification, L2 is a substituted or unsubstituted monocyclic or polycyclic arylene group having 6 to 15 carbon atoms.

According to another exemplary embodiment of the present specification, L2 is a substituted or unsubstituted phenylene group.

According to another exemplary embodiment of the present specification, L2 is a substituted or unsubstituted phenylene group, and n is 0 or 1.

According to one exemplary embodiment of the present specification, L2 is a substituted or unsubstituted phenylene group, or n is 0.

According to another exemplary embodiment of the present specification, L2 is a phenylene group.

According to another exemplary embodiment of the present specification, $(L2)_n$ is a direct bond; or a substituted or unsubstituted phenylene group.

According to another exemplary embodiment, $(L2)_n$ is a direct bond; or a phenylene group.

According to the exemplary embodiment of the present specification,

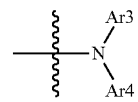

of Chemical Formula 2 is any one of the following structures.

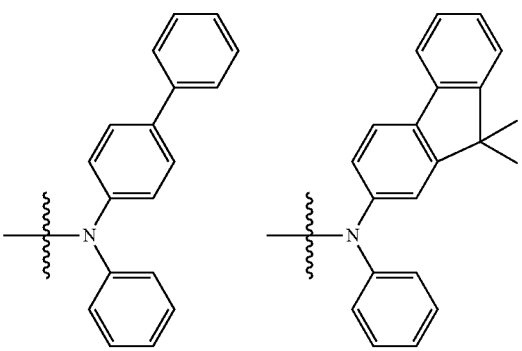

57
-continued
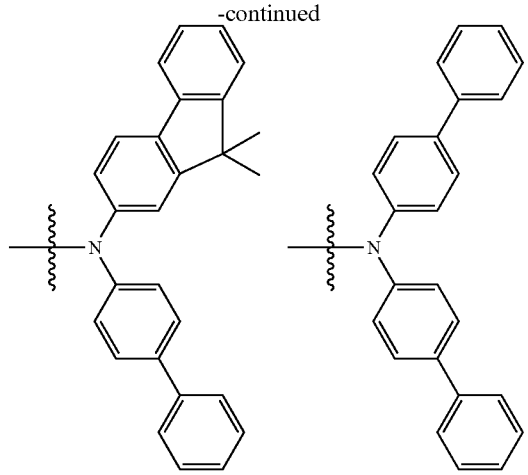
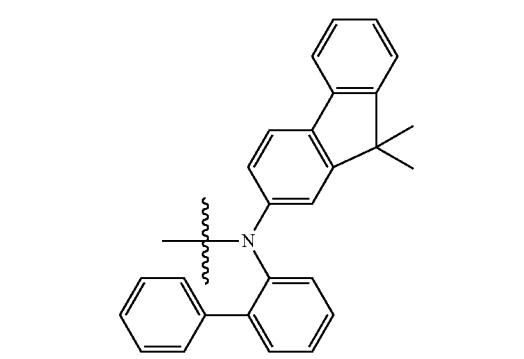
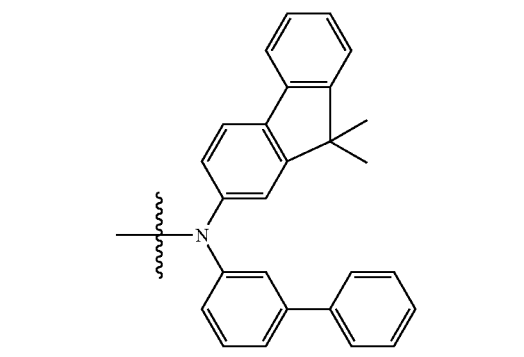
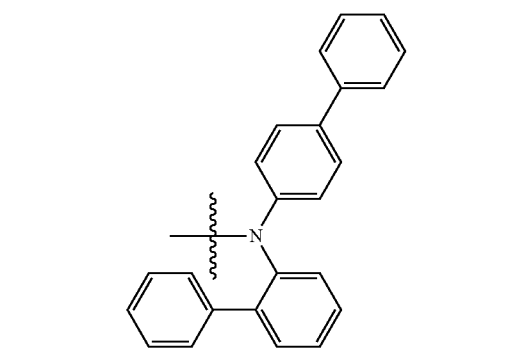
58
-continued
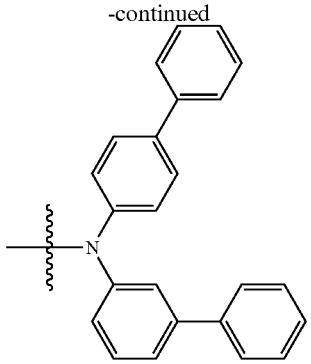
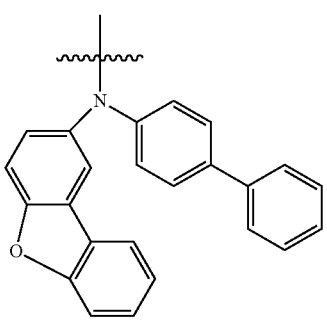
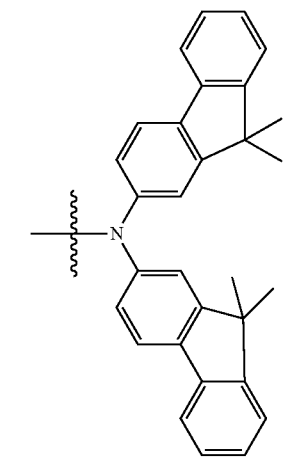
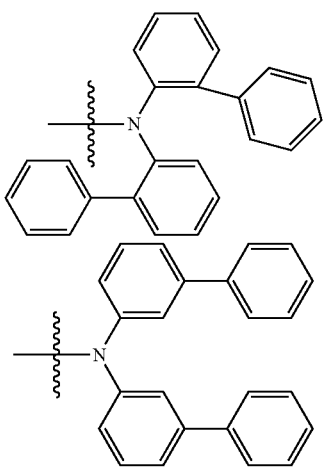

In another exemplary embodiment,

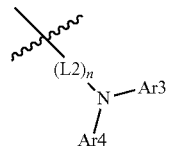

of Chemical Formula 2 is connected to R4b of the following spirobifluorene structure of Chemical Formula 2.

In another exemplary embodiment,

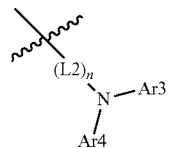

of Chemical Formula 2 is connected to R4c of the following spirobifluorene structure of Chemical Formula 2.

In another exemplary embodiment,

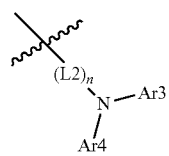

of Chemical Formula 2 is connected to R4d of the following spirobifluorene structure of Chemical Formula 2.

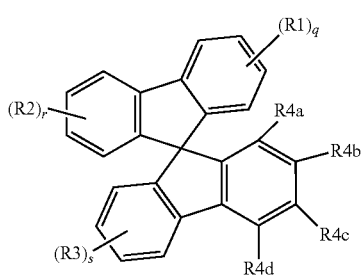

According to the exemplary embodiment of the present specification, the compound represented by Chemical Formula 2 is represented by any one of the following Chemical Formulas 2-1 to 2-45.

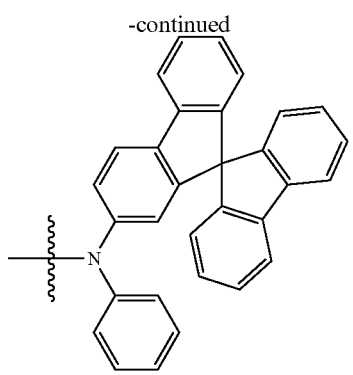

In the present specification,

means a portion bonded to $(L2)_n$ in Chemical Formula 2.

In the exemplary embodiment of the present specification,

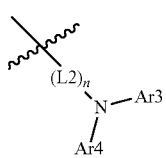

of Chemical Formula 2 is connected to R4a of the following spirobifluorene structure of Chemical Formula 2.

Chemical Formula 2-1
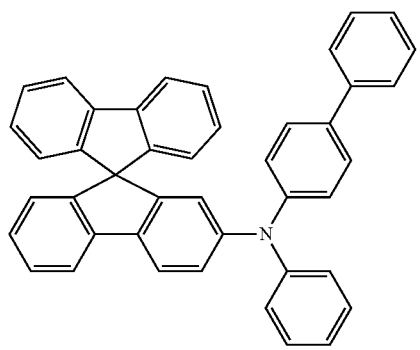
Chemical Formula 2-2
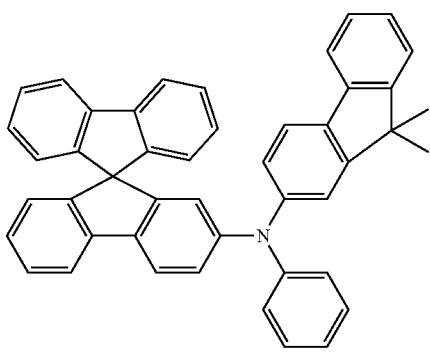
Chemical Formula 2-3
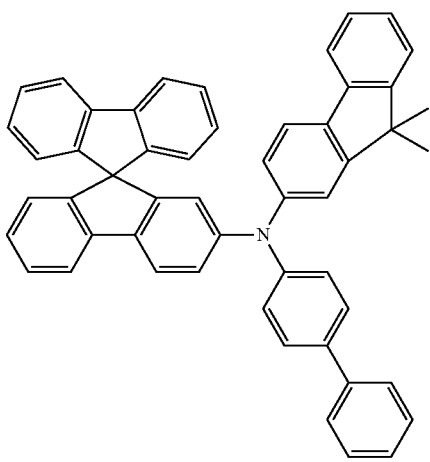
Chemical Formula 2-4
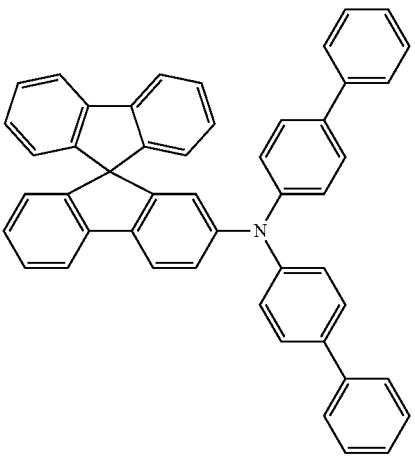
Chemical Formula 2-5
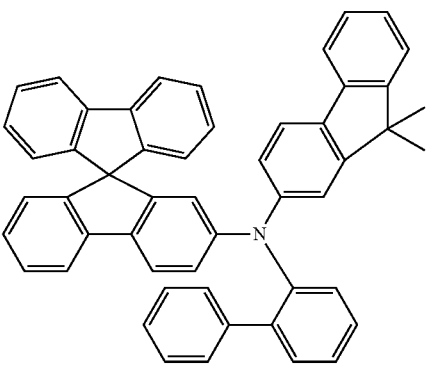
Chemical Formula 2-6
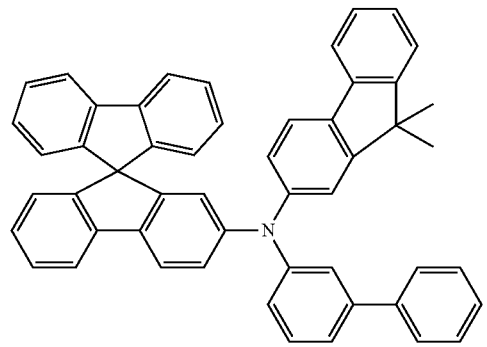
Chemical Formula 2-7
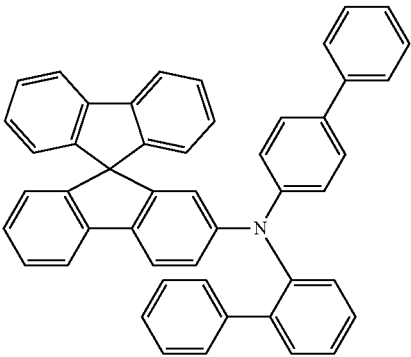

-continued
Chemical Formula 2-8
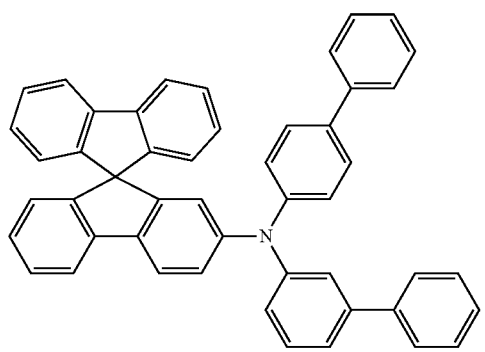
Chemical Formula 2-9
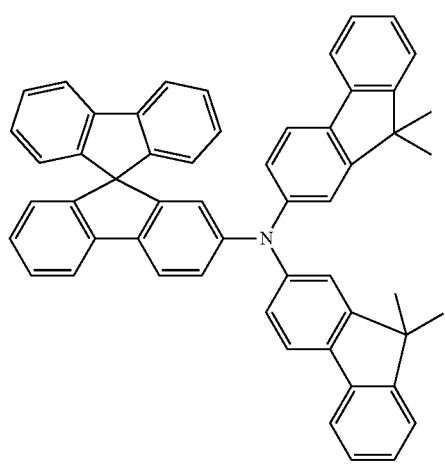
Chemical Formula 2-10
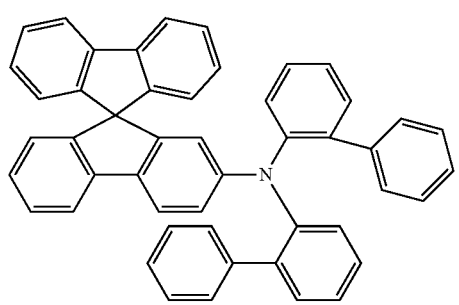
Chemical Formula 2-11
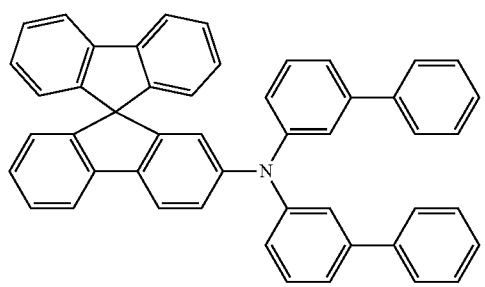
-continued
Chemical Formula 2-12
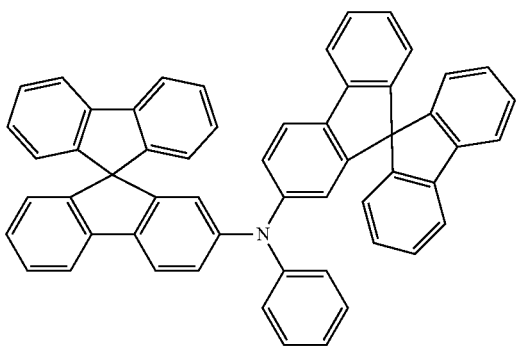
Chemical Formula 2-13
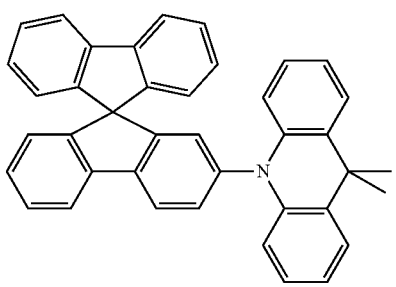
Chemical Formula 2-14
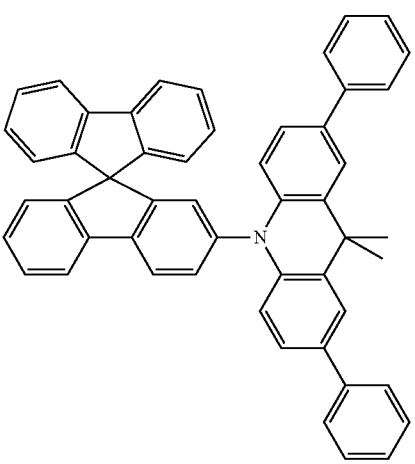
Chemical Formula 2-15
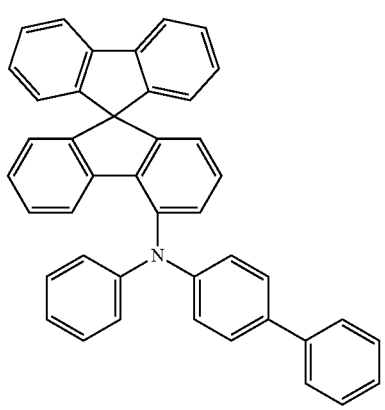

Chemical Formula 2-16
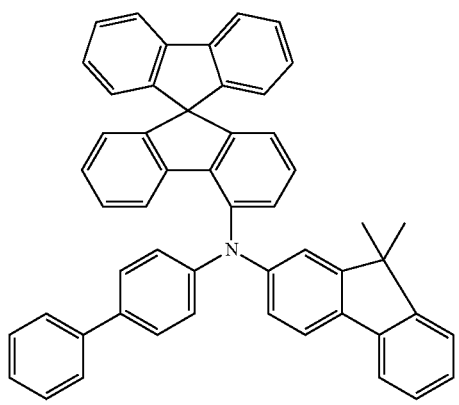
Chemical Formula 2-17
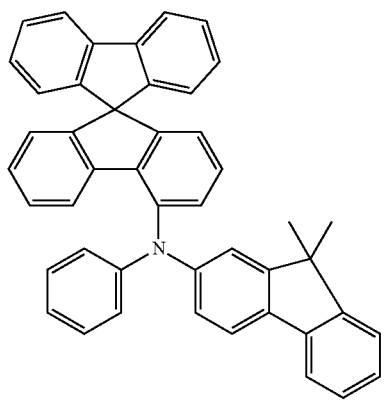
Chemical Formula 2-18
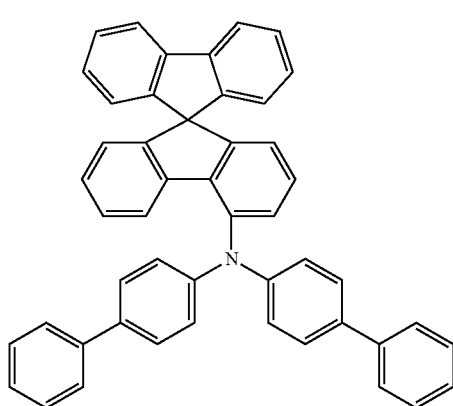
Chemical Formula 2-19
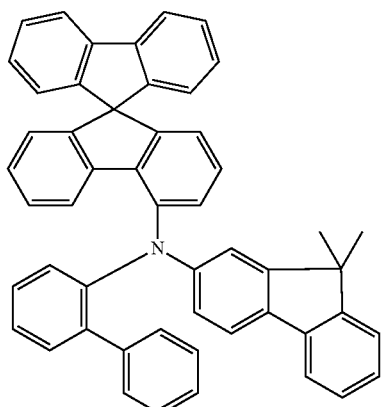
Chemical Formula 2-20
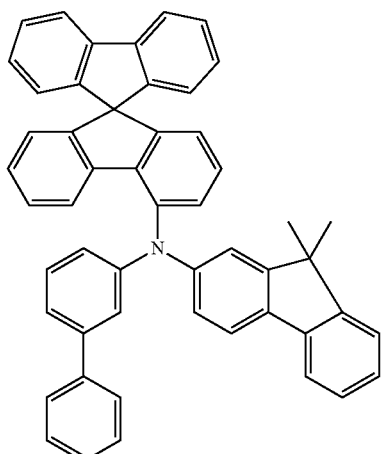
Chemical Formula 2-21
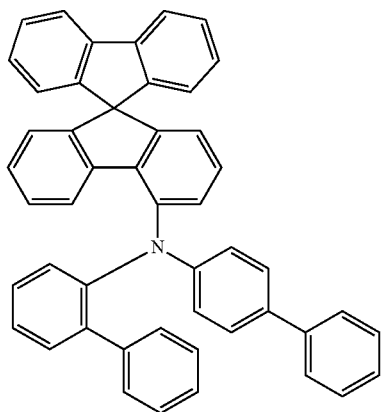

Chemical Formula 2-22
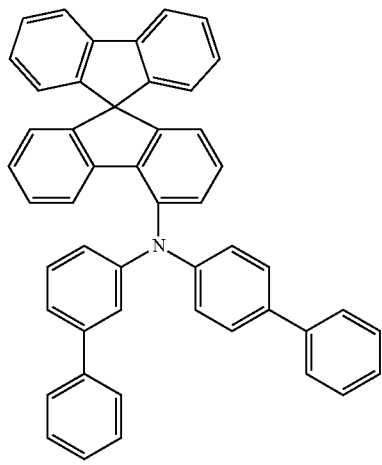
Chemical Formula 2-25
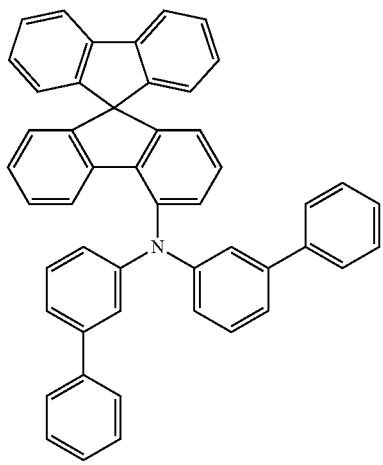
Chemical Formula 2-23
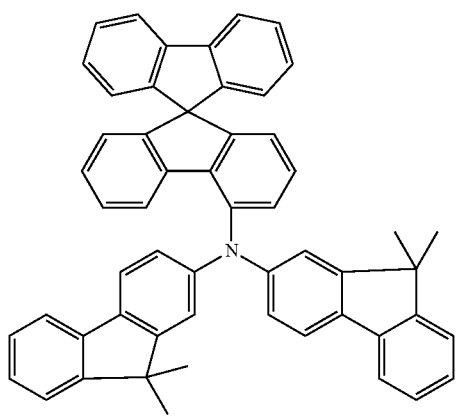
Chemical Formula 2-26
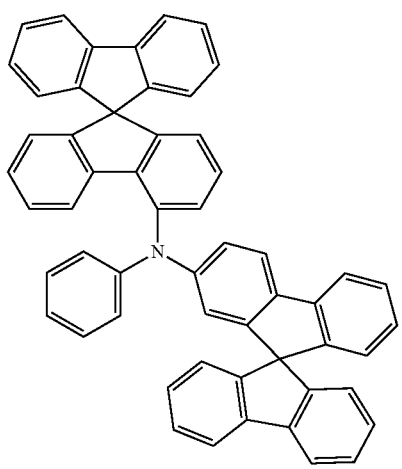
Chemical Formula 2-24
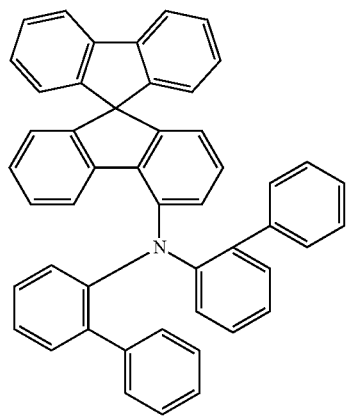
Chemical Formula 2-27
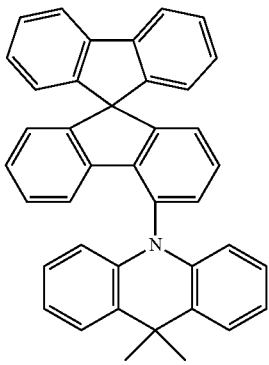

Chemical Formula 2-28
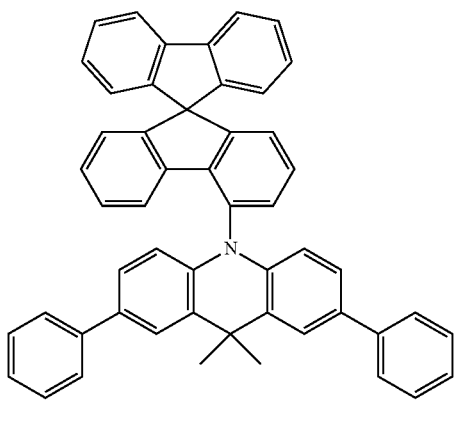
Chemical Formula 2-29
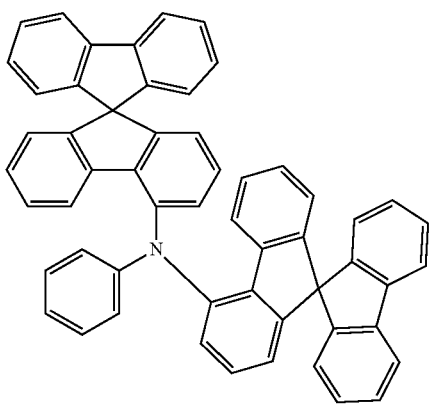
Chemical Formula 2-30
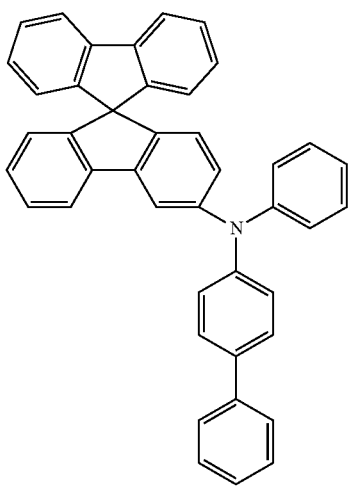
Chemical Formula 2-31
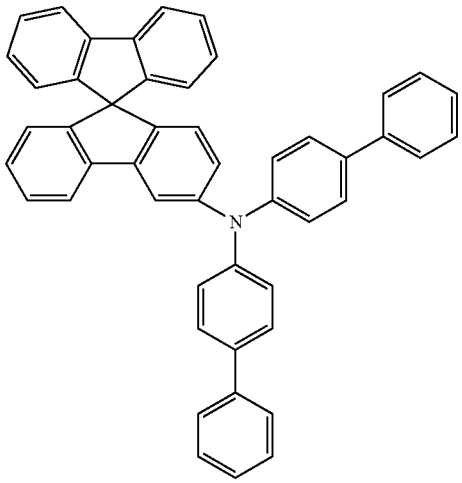
Chemical Formula 2-32
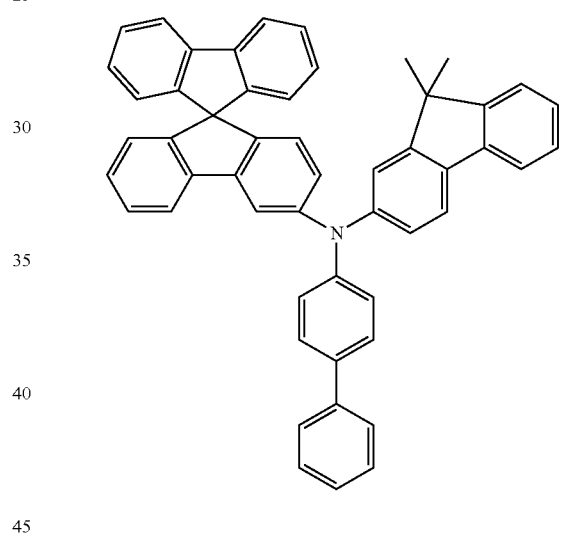
Chemical Formula 2-33
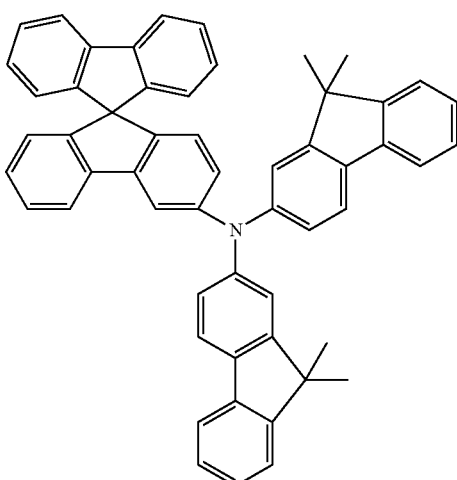

Chemical Formula 2-34
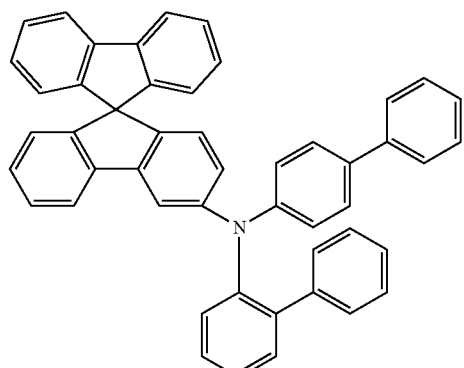
Chemical Formula 2-35
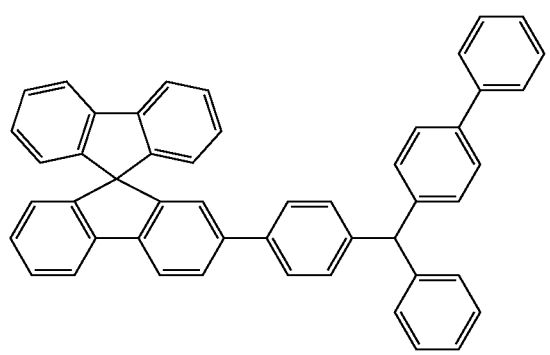
Chemical Formula 2-36
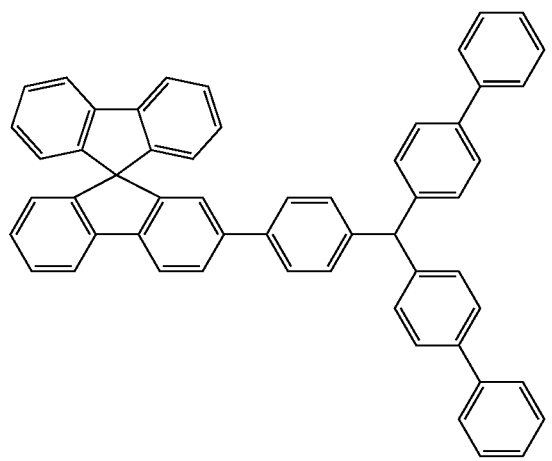
Chemical Formula 2-37
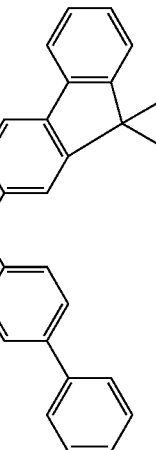
Chemical Formula 2-38
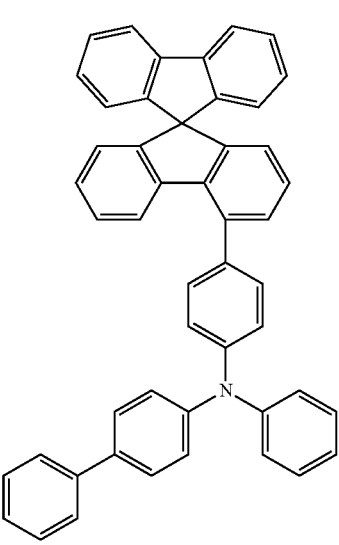
Chemical Formula 2-39
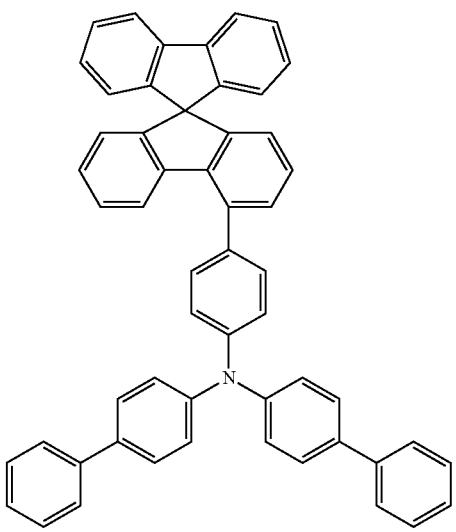

Chemical Formula 2-40

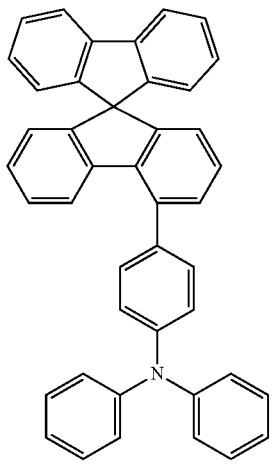

Chemical Formula 2-41

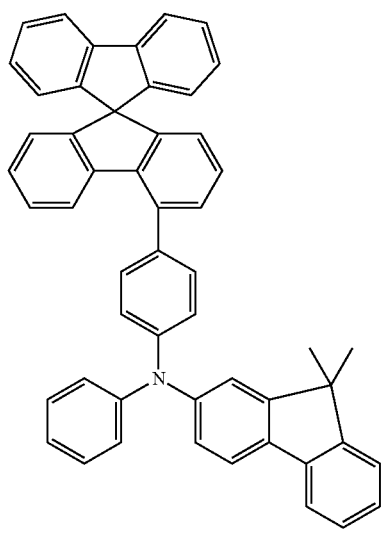

Chemical Formula 2-42

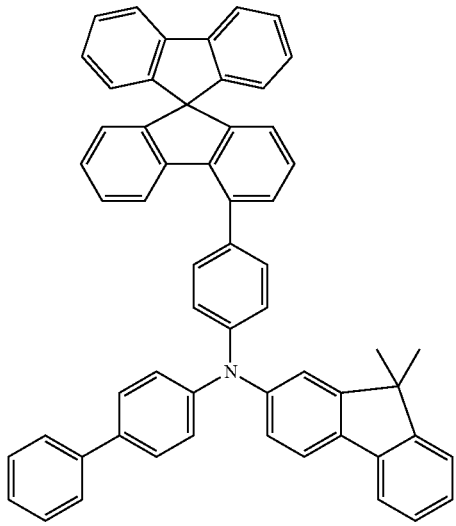

Chemical Formula 2-43

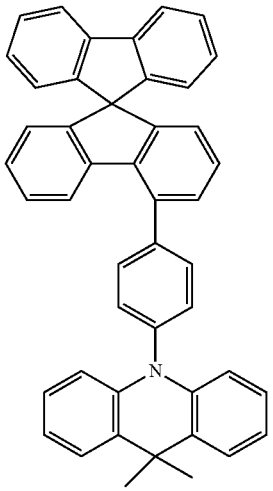

Chemical Formula 2-44

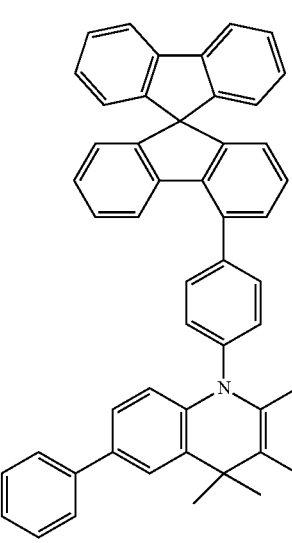

Chemical Formula 2-45

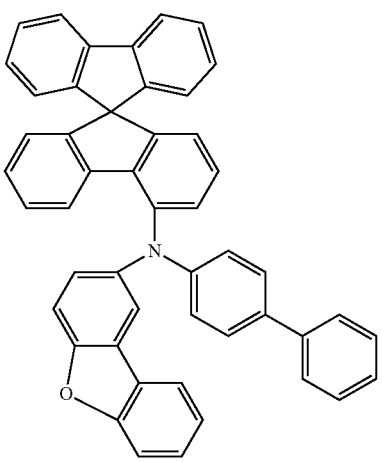

In one exemplary embodiment of the present specification, the organic material layer including the compound represented by Chemical Formula 1 is the electron transport layer, the compound represented by Chemical Formula 1 is represented by Chemical Formula 1-1-19, and the organic material layer including the compound represented by Chemical Formula 2 is the electron blocking layer.

In one exemplary embodiment, the organic material layer including the compound represented by Chemical Formula 2 is the electron blocking layer, and the compound represented by Chemical Formula 2 is represented by Chemical Formula 2-16. In another exemplary embodiment, the organic material layer including the compound represented by Chemical Formula 2 is the electron blocking layer, and the compound represented by Chemical Formula 2 is represented by Chemical Formula 2-18.

In the exemplary embodiment of the present specification, the organic material layer including the compound represented by Chemical Formula 1 may further include an n-type dopant.

In the exemplary embodiment of the present specification, the n-type dopant includes alkali metal, an alkali metal compound, alkali earth metal, or an alkali earth metal compound, or a combination thereof.

In another exemplary embodiment, the n-type dopant may be one or two or more selected from the group consisting of Li, Na, K, Rb, Cs, Mg, Ca, Sr, Ba, La, Nd, Sm, Eu, Tb, Yb, LiF, Li$_2$O, CsF, or the following compounds, but is not limited thereto.

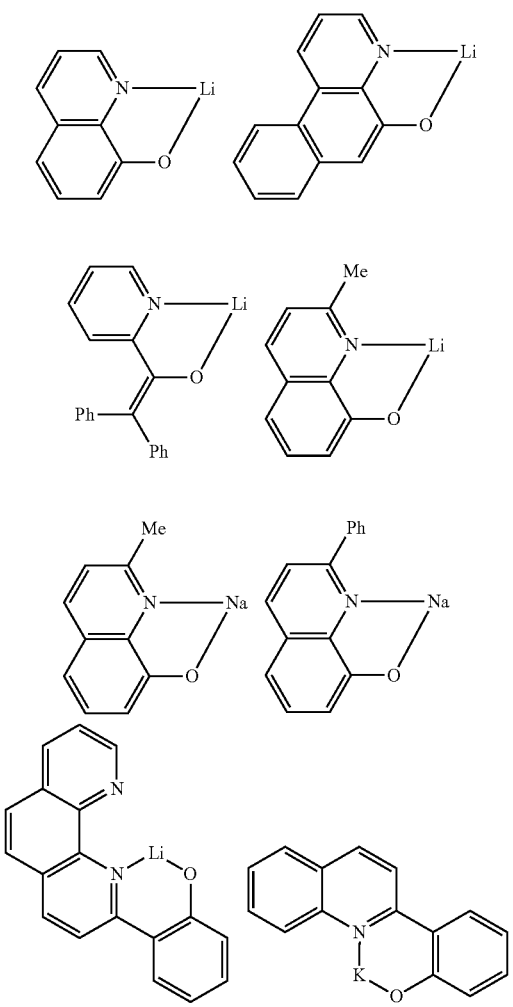

-continued

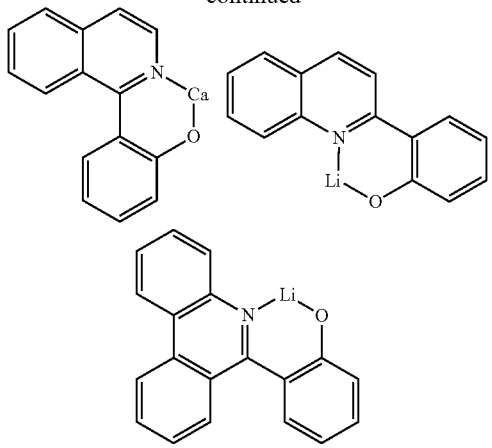

In the exemplary embodiment of the present specification, the compound represented by Chemical Formula 1 and the n-type dopant may be laminated on the organic light emitting diode at a weight ratio of 9:1 to 1:9.

In one exemplary embodiment, the compound represented by Chemical Formula 1 and the n-type dopant may be laminated on the organic light emitting diode at a weight ratio of 1:1.

The organic light emitting diode of the present specification may be manufactured by a material and a method known in the art, except that the electron transport layer and the electron blocking layer are included.

For example, the organic light emitting diode of the present specification may be manufactured by sequentially laminating the anode, the organic material layer, and the cathode on a substrate. In this case, the organic light emitting diode may be manufactured by depositing a metal, metal oxides having conductivity, or an alloy thereof on the substrate by using a physical vapor deposition (PVD) method such as a sputtering method or an e-beam evaporation method to form the anode, forming the organic material layer including the hole injection layer, the hole transport layer, the electron blocking layer, the light emitting layer, the electron transport layer, and the electron injection layer thereon, and then depositing a material that can be used as the cathode thereon. In addition to the aforementioned method, the organic light emitting diode may be manufactured by sequentially depositing a cathode material, the organic material layer, and an anode material on the substrate. In addition to the aforementioned method, the organic light emitting diode may be manufactured by sequentially depositing the anode material, the organic material layer, and the cathode material on the substrate.

The organic material layer of the organic light emitting diode of the present specification may have a multilayered structure where one or more organic material layers are laminated.

In the exemplary embodiment of the present specification, the organic light emitting diode may further include one layer or two or more layers selected from the group consisting of the hole injection layer, the hole transport layer, the electron transport layer, the electron injection layer, the electron blocking layer, and the hole blocking layer.

For example, the structure of the organic light emitting diode of the present specification may have a structure illustrated in FIG. 1 or 2, but is not limited thereto.

FIG. 1 illustrates a structure of an organic light emitting diode where an anode 201, a hole transport layer 301, an electron blocking layer 401, a light emitting layer 501, an electron transport layer 601, and a cathode 701 are sequentially laminated on a substrate 101. FIG. 1 is the exemplified structure according to the exemplary embodiment of the present specification, and may further include another organic material layer. In FIG. 1, the compound represented by Chemical Formula 2 is included in the electron blocking layer 401, and the compound represented by Chemical Formula 1 is included in the electron transport layer 601.

FIG. 2 illustrates a structure of an organic light emitting diode where the anode 201, the hole transport layer 301, the electron blocking layer 401, the light emitting layer 501, the electron transport layer 601, an electron injection layer 801, and the cathode 701 are sequentially laminated on the substrate 101. In FIG. 2, the compound represented by Chemical Formula 2 may be included in the electron blocking layer 401, and the compound represented by Chemical Formula 1 may be included in the electron transport layer 601. Further, the compound represented by Chemical Formula 2 may be included in the electron blocking layer 401, and the compound represented by Chemical Formula 1 may be included in the electron injection layer 801. Further, the compound represented by Chemical Formula 2 may be included in the electron blocking layer 401, and the compound represented by Chemical Formula 1 may be included in the electron transport layer 601 and the electron injection layer 801.

FIGS. 1 and 2 are the exemplified structures according to the exemplary embodiment of the present specification, and may further include other organic material layers.

In the case where the organic light emitting diode includes a plurality of organic material layers, the organic material layers may be formed of the same material or different materials.

As the anode material, in general, it is preferable to use a material having a large work function so as to smoothly inject holes into the organic material layer. Specific examples of the anode material that may be used in the present invention include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as ZnO:Al or $SNO_2$:Sb; conductive polymers such as poly(3-methylthiophene), poly[3,4-(ethylene-1,2-dioxy)thiophene] (PEDOT), polypyrrole, and polyaniline, and the like, but are not limited thereto.

It is preferable that the cathode material be, in general, a material having a small work function so as to easily inject electrons into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or $LiO_2$/Al, and the like, but are not limited thereto.

The hole injection material is a layer injecting the holes from the electrode, and it is preferable that the hole injection material be a compound which has an ability of transporting the holes to have a hole injection effect from the anode and an excellent hole injection effect to the light emitting layer or the light emitting material, prevents movement of the exciton generated in the light emitting layer to the electron injection layer or the electron injection material, and has an excellent thin film forming ability. It is preferable that a highest occupied molecular orbital (HOMO) of the hole injection material be between the work function of the anode material and a HOMO of a peripheral organic material layer. Specific examples of the hole injection material include metal porphyrine, oligothiophene, an arylamine-based organic material, a hexanitrilehexaazatriphenylene-based organic material, a quinacridone-based organic material, a perylene-based organic material, anthraquinone, polyaniline, a polythiophene-based conductive polymer, and the like, but are not limited thereto.

The hole transport layer is a layer receiving the holes from the hole injection layer and transporting the holes to the light emitting layer, the hole transport material is a material capable of receiving the holes from the anode or the hole injection layer and transporting the holes to the light emitting layer, and a material having large mobility to the holes is suitable as the hole transport material. Specific examples thereof include an arylamine-based organic material, a conductive polymer, a block copolymer in which a conjugate portion and a non-conjugate portion are present together, and the like, but are not limited thereto.

The light emitting material is a material that receives and combines the holes and the electrons from the hole transport layer and the electron transport layer, such that light in a visible light region is emitted, and it is preferable to use a material having excellent quantum efficiency to fluorescence or phosphorescence. Specific examples thereof include a 8-hydroxy-quinoline aluminum complex ($Alq_3$); a carbazole-based compound; a dimerized styryl compound; BAlq; a 10-hydroxybenzoquinoline-metal compound; benzoxazole, benzthiazole, and benzimidazole-based compounds; a poly(p-phenylenevinylene) (PPV)-based polymer; a spiro compound; polyfluorene, lubrene, and the like, but are not limited thereto.

The light emitting layer may include a host material and a dopant material. Examples of the host material include a condensation aromatic ring derivative, a hetero-ring-containing compound, or the like. Specific examples of the compensation aromatic ring derivative include an anthracene derivative, a pyrene derivative, a naphthalene derivative, a pentacene derivative, a phenanthrene compound, a fluoranthene compound, and the like, and specific examples of the hetero-ring-containing compound include a carbazole derivative, a dibenzofuran derivative, a ladder-type furan compound, a pyrimidine derivative, and the like, but the examples are not limited thereto.

Examples of the dopant material include an organic compound, a metal, or a metal compound.

Examples of the organic compound as the dopant material include an aromatic amine derivative, a styrylamine compound, a boron complex, a fluoranthene compound, and the like. Specifically, the aromatic amine derivative is a compensation aromatic ring derivative having a substituted or unsubstituted arylamino group, examples thereof include pyrene, anthracene, chrysene, and periflanthene having the arylamino group, the styrylamine compound is a compound where at least one arylvinyl group is substituted in substituted or unsubstituted arylamine, and in the styrylamine compound, one or two or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetraamine, and the like, but are not limited thereto. Further, a general metal or metal compound may be used as the metal or the metal compound, and specifically, a metal complex may be used. Further, examples of the metal complex include an iridium complex, a platinum complex, and the like, but are not limited thereto.

The electron injection layer is a layer injecting the electrons from the electrode, and a compound which has an ability of transporting the electrons, an electron injection effect from the cathode, and an excellent electron injection effect to the light emitting layer or the light emitting material, prevents movement of an exciton generated in the light emitting layer to the hole injection layer, and has an excellent thin film forming ability is preferable. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone, and the like, and derivatives thereof, a metal complex compound, a nitrogen-containing 5-membered cycle derivative, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)-gallium, bis(2-methyl-8-quinolinato)(1-naphtholato)aluminum, bis(2-methyl-8-quinolinato)(2-naphtholato)gallium, and the like, but are not limited thereto.

The hole blocking layer is a layer preventing holes from reaching the cathode, and in general, may be formed under the same condition as the hole injection layer. Specific examples thereof include an oxadiazole derivative, a triazole derivative, a phenanthroline derivative, BCP, an aluminum complex, and the like, but are not limited thereto.

The organic light emitting diode according to the present specification may be a top emission type, a bottom emission type, or a both-sided emission type according to the used material.

Further, the organic light emitting diode according to the present specification may be a normal type where a lower electrode is the anode and an upper electrode is the cathode, or may be an inverted type where the lower electrode is the cathode and the upper electrode is the anode.

The structure according to the exemplary embodiment of the present specification may act even in an organic electronic diode including an organic solar cell, an organic photoconductor, an organic transistor, and the like by the principle that is similar to the principle applied to the organic light emitting diode.

Hereinafter, the present specification will be described in detail through Examples. However, the Examples according to the present specification may be modified in various other forms, and the scope of the present specification is not interpreted to be limited to the Examples described in detail below. The Examples of the present specification are provided so that a person with ordinary skill in the art may fully understand the present specification.

EXAMPLES

<Example 1> Manufacturing of Organic Light Emitting Diode

The glass substrate (corning 7059 glass) on which the thin film of indium tin oxide (ITO) was applied at a thickness of 1,000 Å was immersed in distilled water having the detergent dissolved therein, and washed by the ultrasonic wave. In this case, the detergent used herein was the product commercially available from Fischer Co. and distilled water used herein was one which had been twice filtered by using the filter commercially available from Millipore Co. ITO was washed for 30 minutes, and washing with ultrasonic waves was then repeated twice for 10 minutes by using distilled water. After the completion of washing with distilled water, washing with ultrasonic waves was performed by using solvents such as isopropyl alcohol, acetone, and methanol, and the resulting product was dried and transported to the plasma washing machine. Further, the substrate was dry-washed by using the oxygen plasma for 5 minutes, and then transported to the vacuum deposition machine.

Hexanitrile hexaazatriphenylene (hereinafter, referred to as "HAT") that was the compound of the following Chemical Formula was deposited under the heat vacuum in a thickness of 100 Å on the prepared ITO transparent electrode to form the thin film. The interfacial property between the substrate and the hole injection layer can be improved by this thin film. Subsequently, the compound of Chemical Formula HT-1 was deposited in a thickness of 800 Å on the thin film to form the hole transport layer, and the compound of Chemical Formula 2-16 was deposited in a thickness of 200 Å thereon to form the electron blocking layer.

Subsequently, 10 wt % of the compound of Chemical Formula PD-1 was doped onto the compound of Chemical Formula PH-1 to form the light emitting layer in a thickness of 300 Å. The electron transport layer material of Chemical Formula 1-1-1 and lithium quinolate (LiQ) were deposited under vacuum as at a weight ratio of 1:1 on the light emitting layer to form the electronic injection and transport layer in a thickness of 300 Å. Lithium fluoride (LiF) in a thickness of 12 Å and aluminum in a thickness of 2,000 Å were subsequently deposited on the electron transport layer to form the cathode.

In the aforementioned process, the deposition rate of the organic material was maintained at 0.3 to 0.8 Å/sec. Further, the deposition rate of lithium fluoride of the cathode was maintained at 0.3 Å/sec, and the deposition rate of aluminum was maintained at 1.5 to 2.5 Å/sec. The degree of vacuum during deposition was maintained at 1 to $3 \times 10^{-7}$.

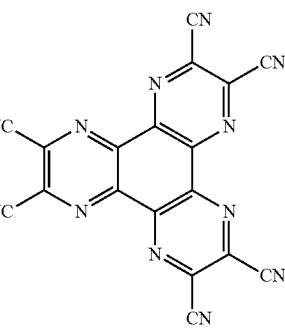

[HAT]

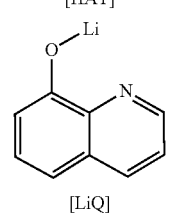

[LiQ]

-continued

[HT-1]

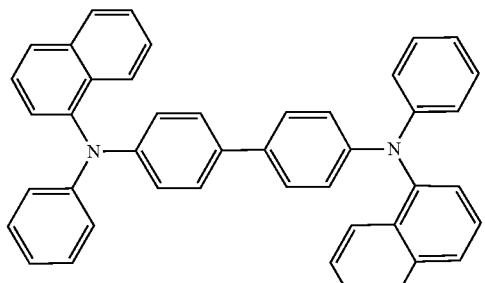

[PH-1]

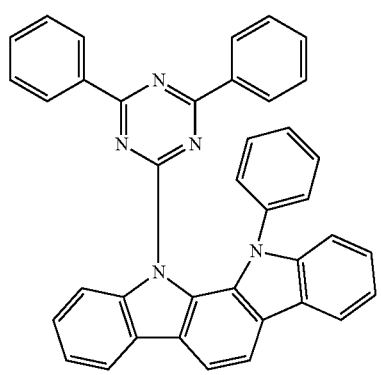

[PD-1]

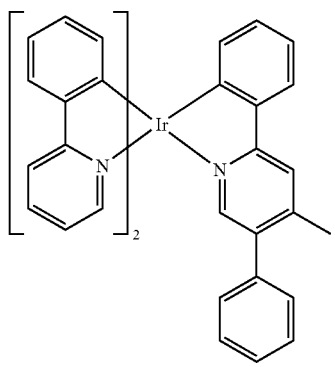

<Example 2> Manufacturing of Organic Light Emitting Diode

The organic light emitting diode was manufactured by the same method as Example 1, except that Chemical Formula 2-3 was used instead of Chemical Formula 2-16 in Example 1.

<Example 3> Manufacturing of Organic Light Emitting Diode

The organic light emitting diode was manufactured by the same method as Example 1, except that Chemical Formula 2-18 was used instead of Chemical Formula 2-16 in Example 1.

<Example 4> Manufacturing of Organic Light Emitting Diode

The organic light emitting diode was manufactured by the same method as Example 1, except that Chemical Formula 2-4 was used instead of Chemical Formula 2-16 in Example 1.

<Example 5> Manufacturing of Organic Light Emitting Diode

The organic light emitting diode was manufactured by the same method as Example 1, except that Chemical Formula 1-1-26 was used instead of Chemical Formula 1-1-1 in Example 1.

<Example 6> Manufacturing of Organic Light Emitting Diode

The organic light emitting diode was manufactured by the same method as Example 2, except that Chemical Formula 1-1-26 was used instead of Chemical Formula 1-1-1 in Example 2.

<Example 7> Manufacturing of Organic Light Emitting Diode

The organic light emitting diode was manufactured by the same method as Example 3, except that Chemical Formula 1-1-26 was used instead of Chemical Formula 1-1-1 in Example 3.

<Example 8> Manufacturing of Organic Light Emitting Diode

The organic light emitting diode was manufactured by the same method as Example 4, except that Chemical Formula 1-1-26 was used instead of Chemical Formula 1-1-1 in Example 4.

<Example 9> Manufacturing of Organic Light Emitting Diode

The organic light emitting diode was manufactured by the same method as Example 1, except that Chemical Formula 1-1-27 was used instead of Chemical Formula 1-1-1 in Example 1.

<Example 10> Manufacturing of Organic Light Emitting Diode

The organic light emitting diode was manufactured by the same method as Example 2, except that Chemical Formula 1-1-27 was used instead of Chemical Formula 1-1-1 in Example 2.

<Example 11> Manufacturing of Organic Light Emitting Diode

The organic light emitting diode was manufactured by the same method as Example 3, except that Chemical Formula 1-1-27 was used instead of Chemical Formula 1-1-1 in Example 3.

<Example 12> Manufacturing of Organic Light Emitting Diode

The organic light emitting diode was manufactured by the same method as Example 4, except that Chemical Formula 1-1-27 was used instead of Chemical Formula 1-1-1 in Example 4.

<Example 13> Manufacturing of Organic Light Emitting Diode

The organic light emitting diode was manufactured by the same method as Example 1, except that Chemical Formula 1-1-14 was used instead of Chemical Formula 1-1-1 in Example 1.

<Example 14> Manufacturing of Organic Light Emitting Diode

The organic light emitting diode was manufactured by the same method as Example 2, except that Chemical Formula 1-1-14 was used instead of Chemical Formula 1-1-1 in Example 2.

<Example 15> Manufacturing of Organic Light Emitting Diode

The organic light emitting diode was manufactured by the same method as Example 3, except that Chemical Formula 1-1-14 was used instead of Chemical Formula 1-1-1 in Example 3.

<Example 16> Manufacturing of Organic Light Emitting Diode

The organic light emitting diode was manufactured by the same method as Example 4, except that Chemical Formula 1-1-14 was used instead of Chemical Formula 1-1-1 in Example 4.

<Example 17> Manufacturing of Organic Light Emitting Diode

The organic light emitting diode was manufactured by the same method as Example 1, except that Chemical Formula 1-1-19 was used instead of Chemical Formula 1-1-1 in Example 1.

<Example 18> Manufacturing of Organic Light Emitting Diode

The organic light emitting diode was manufactured by the same method as Example 2, except that Chemical Formula 1-1-19 was used instead of Chemical Formula 1-1-1 in Example 2.

<Example 19> Manufacturing of Organic Light Emitting Diode

The organic light emitting diode was manufactured by the same method as Example 3, except that Chemical Formula 1-1-19 was used instead of Chemical Formula 1-1-1 in Example 3.

<Example 20> Manufacturing of Organic Light Emitting Diode

The organic light emitting diode was manufactured by the same method as Example 4, except that Chemical Formula 1-1-19 was used instead of Chemical Formula 1-1-1 in Example 4.

<Example 21> Manufacturing of Organic Light Emitting Diode

The organic light emitting diode was manufactured by the same method as Example 1, except that Chemical Formula 1-4-4 was used instead of Chemical Formula 1-1-1 in Example 1.

<Example 22> Manufacturing of Organic Light Emitting Diode

The organic light emitting diode was manufactured by the same method as Example 2, except that Chemical Formula 1-4-4 was used instead of Chemical Formula 1-1-1 in Example 2.

<Example 23> Manufacturing of Organic Light Emitting Diode

The organic light emitting diode was manufactured by the same method as Example 3, except that Chemical Formula 1-4-4 was used instead of Chemical Formula 1-1-1 in Example 3.

<Example 24> Manufacturing of Organic Light Emitting Diode

The organic light emitting diode was manufactured by the same method as Example 4, except that Chemical Formula 1-4-4 was used instead of Chemical Formula 1-1-1 in Example 4.

<Comparative Example 1> Manufacturing of Organic Light Emitting Diode

The organic light emitting diode was manufactured by the same method as Example 1, except that the following Chemical Formula ET-1 was used instead of Chemical Formula 1-1-1 in Example 1.

[ET-1]

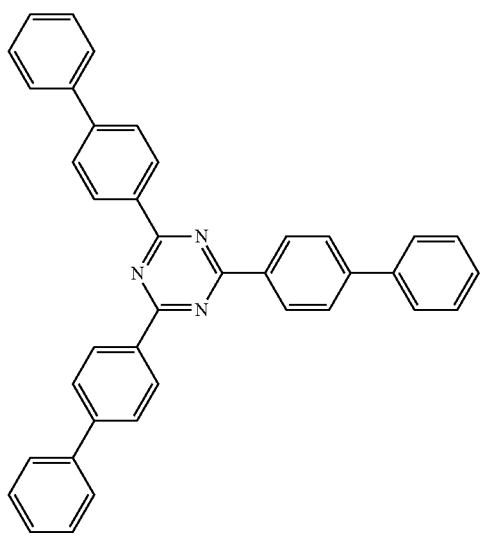

\<Comparative Example 2\> Manufacturing of Organic Light Emitting Diode

The organic light emitting diode was manufactured by the same method as Example 2, except that Chemical Formula ET-1 was used instead of Chemical Formula 1-1-1 in Example 2.

\<Comparative Example 3\> Manufacturing of Organic Light Emitting Diode

The organic light emitting diode was manufactured by the same method as Example 3, except that Chemical Formula ET-1 was used instead of Chemical Formula 1-1-1 in Example 3.

\<Comparative Example 4\> Manufacturing of Organic Light Emitting Diode

The organic light emitting diode was manufactured by the same method as Example 4, except that Chemical Formula ET-1 was used instead of Chemical Formula 1-1-1 in Example 4.

\<Comparative Example 5\> Manufacturing of Organic Light Emitting Diode

The organic light emitting diode was manufactured by the same method as Example 1, except that the following Chemical Formula ET-2 was used instead of Chemical Formula 1-1-1 in Example 1.

[ET-2]

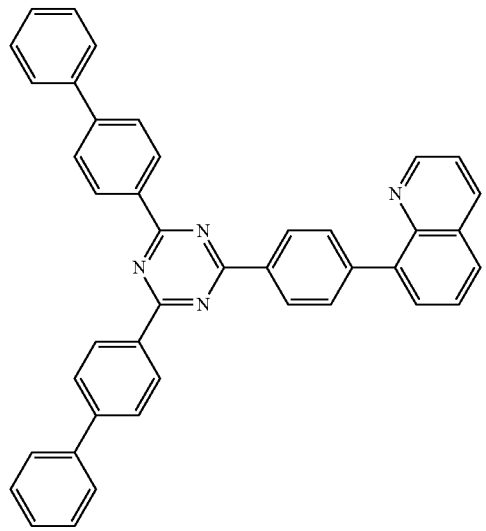

\<Comparative Example 6\> Manufacturing of Organic Light Emitting Diode

The organic light emitting diode was manufactured by the same method as Example 2, except that Chemical Formula ET-2 was used instead of Chemical Formula 1-1-1 in Example 2.

\<Comparative Example 7\> Manufacturing of Organic Light Emitting Diode

The organic light emitting diode was manufactured by the same method as Example 3, except that Chemical Formula ET-2 was used instead of Chemical Formula 1-1-1 in Example 3.

\<Comparative Example 8\> Manufacturing of Organic Light Emitting Diode

The organic light emitting diode was manufactured by the same method as Example 4, except that Chemical Formula ET-2 was used instead of Chemical Formula 1-1-1 in Example 4.

\<Comparative Example 9\> Manufacturing of Organic Light Emitting Diode

The organic light emitting diode was manufactured by the same method as Example 1, except that the following Chemical Formula ET-3 was used instead of Chemical Formula 1-1-1 in Example 1.

[ET-3]

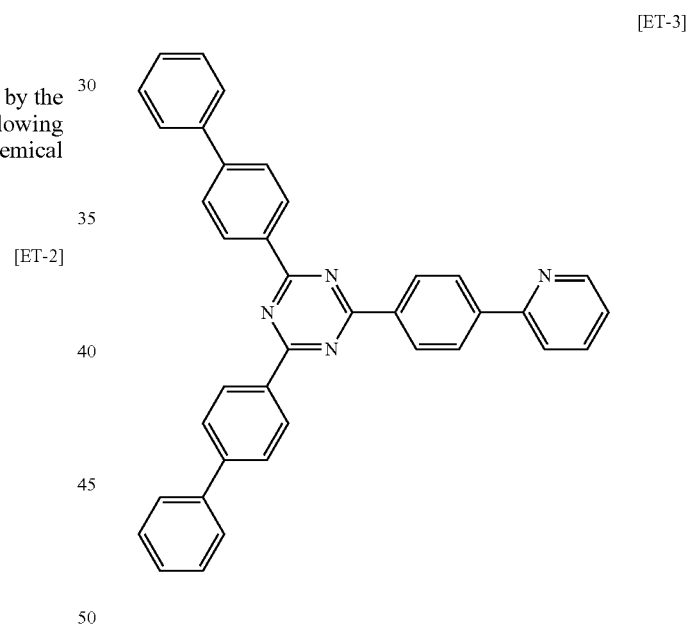

\<Comparative Example 10\> Manufacturing of Organic Light Emitting Diode

The organic light emitting diode was manufactured by the same method as Example 2, except that Chemical Formula ET-3 was used instead of Chemical Formula 1-1-1 in Example 2.

\<Comparative Example 11\> Manufacturing of Organic Light Emitting Diode

The organic light emitting diode was manufactured by the same method as Example 3, except that Chemical Formula ET-3 was used instead of Chemical Formula 1-1-1 in Example 3.

\<Comparative Example 12\> Manufacturing of Organic Light Emitting Diode

The organic light emitting diode was manufactured by the same method as Example 4, except that Chemical Formula ET-3 was used instead of Chemical Formula 1-1-1 in Example 4.

\<Comparative Example 13\> Manufacturing of Organic Light Emitting Diode

The organic light emitting diode was manufactured by the same method as Example 1, except that the following Chemical Formula ET-4 was used instead of Chemical Formula 1-1-1 in Example 1.

[ET-4]

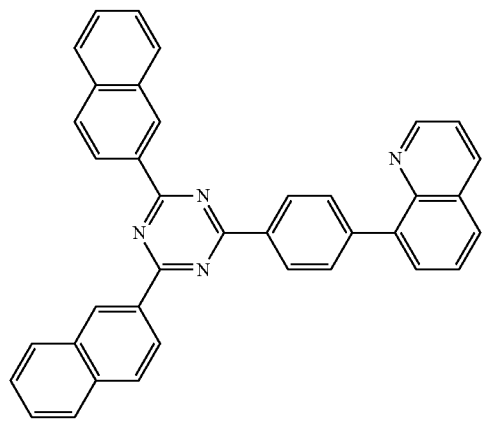

\<Comparative Example 14\> Manufacturing of Organic Light Emitting Diode

The organic light emitting diode was manufactured by the same method as Example 2, except that Chemical Formula ET-4 was used instead of Chemical Formula 1-1-1 in Example 2.

\<Comparative Example 15\> Manufacturing of Organic Light Emitting Diode

The organic light emitting diode was manufactured by the same method as Example 3, except that Chemical Formula ET-4 was used instead of Chemical Formula 1-1-1 in Example 3.

\<Comparative Example 16\> Manufacturing of Organic Light Emitting Diode

The organic light emitting diode was manufactured by the same method as Example 4, except that Chemical Formula ET-4 was used instead of Chemical Formula 1-1-1 in Example 4.

\<Comparative Example 17\> Manufacturing of Organic Light Emitting Diode

The organic light emitting diode was manufactured by the same method as Example 1, except that the following Chemical Formula ET-5 was used instead of Chemical Formula 1-1-1 in Example 1.

[ET-5]

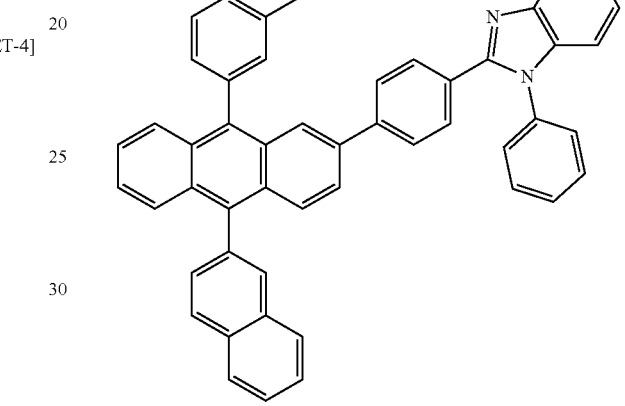

\<Comparative Example 18\> Manufacturing of Organic Light Emitting Diode

The organic light emitting diode was manufactured by the same method as Example 2, except that Chemical Formula ET-5 was used instead of Chemical Formula 1-1-1 in Example 2.

\<Comparative Example 19\> Manufacturing of Organic Light Emitting Diode

The organic light emitting diode was manufactured by the same method as Example 3, except that Chemical Formula ET-5 was used instead of Chemical Formula 1-1-1 in Example 3.

\<Comparative Example 20\> Manufacturing of Organic Light Emitting Diode

The organic light emitting diode was manufactured by the same method as Example 4, except that Chemical Formula ET-5 was used instead of Chemical Formula 1-1-1 in Example 4.

<Comparative Example 21> Manufacturing of Organic Light Emitting Diode The organic light emitting diode was manufactured by the same method as Example 1, except that the following Chemical Formula ET-6 was used instead of Chemical Formula 1-1-1 in Example 1.

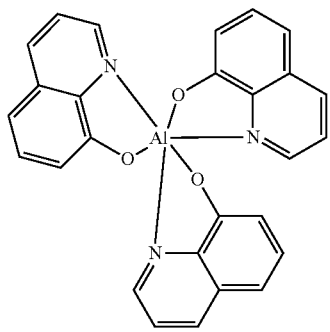

[ET-6]

<Comparative Example 22> Manufacturing of Organic Light Emitting Diode The organic light emitting diode was manufactured by the same method as Example 2, except that Chemical Formula ET-6 was used instead of Chemical Formula 1-1-1 in Example 2.

<Comparative Example 23> Manufacturing of Organic Light Emitting Diode The organic light emitting diode was manufactured by the same method as Example 3, except that Chemical Formula ET-6 was used instead of Chemical Formula 1-1-1 in Example 3.

<Comparative Example 24> Manufacturing of Organic Light Emitting Diode The organic light emitting diode was manufactured by the same method as Example 4, except that Chemical Formula ET-6 was used instead of Chemical Formula 1-1-1 in Example 4.

<Comparative Example 25> Manufacturing of Organic Light Emitting Diode The organic light emitting diode was manufactured by the same method as Example 1, except that Chemical Formula EB-1 was used instead of Chemical Formula 2-16 in Example 1.

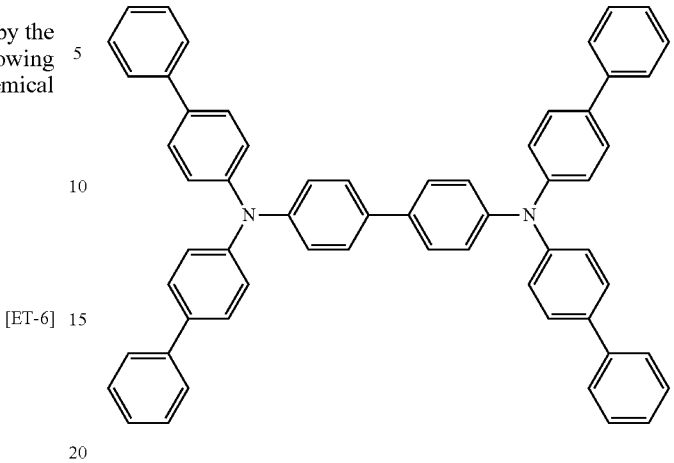

[EB-1]

<Comparative Example 26> Manufacturing of Organic Light Emitting Diode The organic light emitting diode was manufactured by the same method as Example 5, except that Chemical Formula EB-1 was used instead of Chemical Formula 2-16 in Example 5.

<Comparative Example 27> Manufacturing of Organic Light Emitting Diode The organic light emitting diode was manufactured by the same method as Example 9, except that Chemical Formula EB-1 was used instead of Chemical Formula 2-16 in Example 9.

<Comparative Example 28> Manufacturing of Organic Light Emitting Diode The organic light emitting diode was manufactured by the same method as Example 13, except that Chemical Formula EB-1 was used instead of Chemical Formula 2-16 in Example 13.

<Comparative Example 29> Manufacturing of Organic Light Emitting Diode The organic light emitting diode was manufactured by the same method as Example 17, except that Chemical Formula EB-1 was used instead of Chemical Formula 2-16 in Example 17.

<Comparative Example 30> Manufacturing of Organic Light Emitting Diode The organic light emitting diode was manufactured by the same method as Example 21, except that Chemical Formula EB-1 was used instead of Chemical Formula 2-16 in Example 21.

<Comparative Example 31> Manufacturing of Organic Light Emitting Diode The organic light emitting diode was manufactured by the same method as Example 1, except that Chemical Formula EB-2 was used instead of Chemical Formula 2-16 in Example 1.

[EB-2]

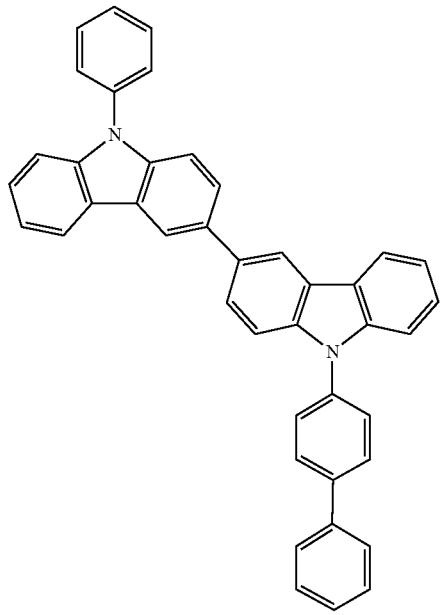

<Comparative Example 32> Manufacturing of Organic Light Emitting Diode

The organic light emitting diode was manufactured by the same method as Example 5, except that Chemical Formula EB-2 was used instead of Chemical Formula 2-16 in Example 5.

<Comparative Example 33> Manufacturing of Organic Light Emitting Diode

The organic light emitting diode was manufactured by the same method as Example 9, except that Chemical Formula EB-2 was used instead of Chemical Formula 2-16 in Example 9.

<Comparative Example 34> Manufacturing of Organic Light Emitting Diode

The organic light emitting diode was manufactured by the same method as Example 13, except that Chemical Formula EB-2 was used instead of Chemical Formula 2-16 in Example 13.

<Comparative Example 35> Manufacturing of Organic Light Emitting Diode

The organic light emitting diode was manufactured by the same method as Example 17, except that Chemical Formula EB-2 was used instead of Chemical Formula 2-16 in Example 17.

<Comparative Example 36> Manufacturing of Organic Light Emitting Diode

The organic light emitting diode was manufactured by the same method as Example 21, except that Chemical Formula EB-2 was used instead of Chemical Formula 2-16 in Example 21.

<Comparative Example 37> Manufacturing of Organic Light Emitting Diode

The organic light emitting diode was manufactured by the same method as Example 1, except that the compound of ET-1 and Chemical Formula EB-1 were used instead of Chemical Formula 1-1-1 and Chemical Formula 2-16 in Example 1, respectively.

<Comparative Example 38> Manufacturing of Organic Light Emitting Diode

The organic light emitting diode was manufactured by the same method as Example 1, except that the compound of ET-1 and Chemical Formula EB-2 were used instead of Chemical Formula 1-1-1 and Chemical Formula 2-16 in Example 1, respectively.

<Comparative Example 39> Manufacturing of Organic Light Emitting Diode

The organic light emitting diode was manufactured by the same method as Example 1, except that the compound of ET-2 and Chemical Formula EB-1 were used instead of Chemical Formula 1-1-1 and Chemical Formula 2-16 in Example 1, respectively.

<Comparative Example 40> Manufacturing of Organic Light Emitting Diode

The organic light emitting diode was manufactured by the same method as Example 1, except that the compound of ET-2 and Chemical Formula EB-2 were used instead of Chemical Formula 1-1-1 and Chemical Formula 2-16 in Example 1, respectively.

<Comparative Example 41> Manufacturing of Organic Light Emitting Diode

The organic light emitting diode was manufactured by the same method as Example 1, except that the compound of ET-3 and Chemical Formula EB-1 were used instead of Chemical Formula 1-1-1 and Chemical Formula 2-16 in Example 1, respectively.

<Comparative Example 42> Manufacturing of Organic Light Emitting Diode

The organic light emitting diode was manufactured by the same method as Example 1, except that the compound of ET-3 and Chemical Formula EB-2 were used instead of Chemical Formula 1-1-1 and Chemical Formula 2-16 in Example 1, respectively.

<Comparative Example 43> Manufacturing of Organic Light Emitting Diode

The organic light emitting diode was manufactured by the same method as Example 1, except that the compound of ET-4 and Chemical Formula EB-1 were used instead of Chemical Formula 1-1-1 and Chemical Formula 2-16 in Example 1, respectively.

<Comparative Example 44> Manufacturing of Organic Light Emitting Diode

The organic light emitting diode was manufactured by the same method as Example 1, except that the compound of ET-4 and Chemical Formula EB-2 were used instead of Chemical Formula 1-1-1 and Chemical Formula 2-16 in Example 1, respectively.

<Comparative Example 45> Manufacturing of Organic Light Emitting Diode

The organic light emitting diode was manufactured by the same method as Example 1, except that the compound of ET-5 and Chemical Formula EB-1 were used instead of Chemical Formula 1-1-1 and Chemical Formula 2-16 in Example 1, respectively.

<Comparative Example 46> Manufacturing of Organic Light Emitting Diode

The organic light emitting diode was manufactured by the same method as Example 1, except that the compound of ET-5 and Chemical Formula EB-2 were used instead of Chemical Formula 1-1-1 and Chemical Formula 2-16 in Example 1, respectively.

<Comparative Example 47> Manufacturing of Organic Light Emitting Diode

The organic light emitting diode was manufactured by the same method as Example 1, except that the compound of ET-6 and Chemical Formula EB-1 were used instead of Chemical Formula 1-1-1 and Chemical Formula 2-16 in Example 1, respectively.

<Comparative Example 48> Manufacturing of Organic Light Emitting Diode

The organic light emitting diode was manufactured by the same method as Example 1, except that the compound of ET-6 and Chemical Formula EB-2 were used instead of Chemical Formula 1-1-1 and Chemical Formula 2-16 in Example 1, respectively.

<Comparative Example 49> Manufacturing of Organic Light Emitting Diode

The organic light emitting diode was manufactured by the same method as Example 17, except that the electron blocking layer including Chemical Formula 2-16 was not formed and the compound of HT-1 was deposited in a thickness of 1,400 Å to form the hole transport layer in Example 17.

<Comparative Example 50> Manufacturing of Organic Light Emitting Diode

The organic light emitting diode was manufactured by the same method as Example 1, except that the following Chemical Formula ET-7 was used instead of Chemical Formula 1-1-1 in Example 1.

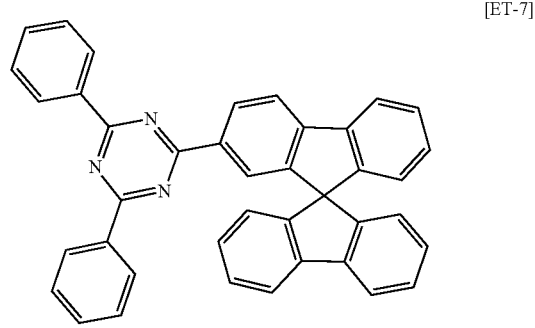 [SMILES: c1ccc(-c2nc(-c3ccccc3)nc(-c3ccc4c(c3)C3(c5ccccc5-c5ccccc53)c3ccccc3-4)n2)cc1]

[ET-7]

<Comparative Example 51> Manufacturing of Organic Light Emitting Diode

The organic light emitting diode was manufactured by the same method as Example 2, except that Chemical Formula ET-7 was used instead of Chemical Formula 1-1-1 in Example 2.

<Comparative Example 52> Manufacturing of Organic Light Emitting Diode

The organic light emitting diode was manufactured by the same method as Example 3, except that Chemical Formula ET-7 was used instead of Chemical Formula 1-1-1 in Example 3.

<Comparative Example 53> Manufacturing of Organic Light Emitting Diode

The organic light emitting diode was manufactured by the same method as Example 4, except that Chemical Formula ET-7 was used instead of Chemical Formula 1-1-1 in Example 4.

<Comparative Example 54> Manufacturing of Organic Light Emitting Diode

The organic light emitting diode was manufactured by the same method as Example 1, except that the following Chemical Formula ET-8 was used instead of Chemical Formula 1-1-1 in Example 1.

[ET-8]

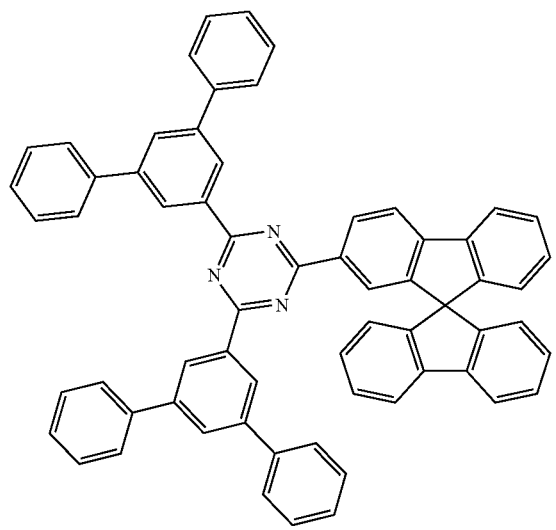

[ET-9]

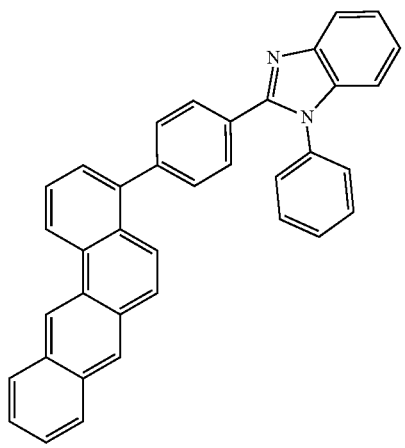

<Comparative Example 55> Manufacturing of Organic Light Emitting Diode

The organic light emitting diode was manufactured by the same method as Example 2, except that Chemical Formula ET-8 was used instead of Chemical Formula 1-1-1 in Example 2.

<Comparative Example 56> Manufacturing of Organic Light Emitting Diode

The organic light emitting diode was manufactured by the same method as Example 3, except that Chemical Formula ET-8 was used instead of Chemical Formula 1-1-1 in Example 3.

<Comparative Example 57> Manufacturing of Organic Light Emitting Diode

The organic light emitting diode was manufactured by the same method as Example 4, except that Chemical Formula ET-8 was used instead of Chemical Formula 1-1-1 in Example 4.

<Comparative Example 58> Manufacturing of Organic Light Emitting Diode

The organic light emitting diode was manufactured by the same method as Example 1, except that the following Chemical Formula ET-9 was used instead of Chemical Formula 1-1-1 in Example 1.

<Comparative Example 59> Manufacturing of Organic Light Emitting Diode

The organic light emitting diode was manufactured by the same method as Example 2, except that Chemical Formula ET-9 was used instead of Chemical Formula 1-1-1 in Example 2.

<Comparative Example 60> Manufacturing of Organic Light Emitting Diode

The organic light emitting diode was manufactured by the same method as Example 3, except that Chemical Formula ET-9 was used instead of Chemical Formula 1-1-1 in Example 3.

<Comparative Example 61> Manufacturing of Organic Light Emitting Diode

The organic light emitting diode was manufactured by the same method as Example 4, except that Chemical Formula ET-9 was used instead of Chemical Formula 1-1-1 in Example 4.

The driving voltage and light emitting efficiency of the organic light emitting diode manufactured by the aforementioned method were measured at the current density of 10 $mA/cm^2$, and the time (LT98) at which brightness was 98% of initial brightness at the current density of 20 $mA/cm^2$ was measured. The result is described in the following Table 1.

TABLE 1

| | Voltage (V) | Current efficiency (cd/A) | Color coordinates (x, y) | Life Time 98 at 20 $mA/cm^2$ |
|---|---|---|---|---|
| Experimental Example 1 | 4.40 | 71.2 | (0.455, 0.533) | 245 |
| Experimental Example 2 | 4.21 | 73.1 | (0.453, 0.537) | 232 |
| Experimental Example 3 | 4.72 | 68.5 | (0.444, 0.536) | 277 |
| Experimental Example 4 | 4.51 | 67.3 | (0.442, 0.542) | 270 |
| Experimental Example 5 | 4.47 | 69.2 | (0.454, 0.534) | 275 |
| Experimental Example 6 | 4.30 | 70.1 | (0.453, 0.529) | 279 |

TABLE 1-continued

| | Voltage (V) | Current efficiency (cd/A) | Color coordinates (x, y) | Life Time 98 at 20 mA/cm² |
|---|---|---|---|---|
| Experimental Example 7 | 4.80 | 65.5 | (0.454, 0.536) | 307 |
| Experimental Example 8 | 4.60 | 65.0 | (0.451, 0.547) | 311 |
| Experimental Example 9 | 4.51 | 73.1 | (0.453, 0.523) | 290 |
| Experimental Example 10 | 4.44 | 72.0 | (0.453, 0.538) | 301 |
| Experimental Example 11 | 4.85 | 69.7 | (0.443, 0.534) | 320 |
| Experimental Example 12 | 4.77 | 67.7 | (0.455, 0.537) | 318 |
| Experimental Example 13 | 4.42 | 70.1 | (0.454, 0.533) | 311 |
| Experimental Example 14 | 4.34 | 69.3 | (0.453, 0.537) | 302 |
| Experimental Example 15 | 4.55 | 67.1 | (0.439, 0.536) | 310 |
| Experimental Example 16 | 4.41 | 65.5 | (0.455, 0.539) | 325 |
| Experimental Example 17 | 4.22 | 68.1 | (0.455, 0.545) | 315 |
| Experimental Example 18 | 4.24 | 68.3 | (0.454, 0.546) | 322 |
| Experimental Example 19 | 4.35 | 66.0 | (0.441, 0.537) | 325 |
| Experimental Example 20 | 4.01 | 64.4 | (0.450, 0.541) | 328 |
| Experimental Example 21 | 4.0 | 74.1 | (0.455, 0.545) | 299 |
| Experimental Example 22 | 4.20 | 72.9 | (0.454, 0.546) | 328 |
| Experimental Example 23 | 4.11 | 74.4 | (0.441, 0.537) | 308 |
| Experimental Example 24 | 4.03 | 71.2 | (0.450, 0.541) | 318 |
| Comparative Example 1 | 4.51 | 64.1 | (0.454, 0.532) | 190 |
| Comparative Example 2 | 4.33 | 66.1 | (0.463, 0.538) | 179 |
| Comparative Example 3 | 4.75 | 59.1 | (0.444, 0.536) | 200 |
| Comparative Example 4 | 4.66 | 61.0 | (0.443, 0.542) | 210 |
| Comparative Example 5 | 4.44 | 55.0 | (0.453, 0.533) | 220 |
| Comparative Example 6 | 4.45 | 48.1 | (0.463, 0.539) | 180 |
| Comparative Example 7 | 4.69 | 51.1 | (0.446, 0.537) | 205 |
| Comparative Example 8 | 4.59 | 58.0 | (0.443, 0.542) | 230 |
| Comparative Example 9 | 4.34 | 51.0 | (0.454, 0.543) | 250 |
| Comparative Example 10 | 4.40 | 45.0 | (0.464, 0.533) | 185 |
| Comparative Example 11 | 4.58 | 49.1 | (0.447, 0.536) | 225 |
| Comparative Example 12 | 4.44 | 49.5 | (0.443, 0.543) | 228 |
| Comparative Example 13 | 4.74 | 59.0 | (0.454, 0.532) | 177 |
| Comparative Example 14 | 4.80 | 51.0 | (0.455, 0.533) | 185 |
| Comparative Example 15 | 5.01 | 55.0 | (0.446, 0.535) | 202 |
| Comparative Example 16 | 4.94 | 55.5 | (0.443, 0.544) | 220 |
| Comparative Example 17 | 4.31 | 70.1 | (0.454, 0.532) | 140 |
| Comparative Example 18 | 4.33 | 68.1 | (0.463, 0.538) | 155 |
| Comparative Example 19 | 4.65 | 59.3 | (0.444, 0.536) | 105 |
| Comparative Example 20 | 4.51 | 63.0 | (0.443, 0.542) | 120 |
| Comparative Example 21 | 5.01 | 48.1 | (0.454, 0.532) | 110 |
| Comparative Example 22 | 5.11 | 42.0 | (0.463, 0.548) | 150 |
| Comparative Example 23 | 4.98 | 51.9 | (0.454, 0.536) | 160 |
| Comparative Example 24 | 4.67 | 48.0 | (0.443, 0.542) | 123 |
| Comparative Example 25 | 4.36 | 55.0 | (0.443, 0.542) | 215 |
| Comparative Example 26 | 4.42 | 55.0 | (0.453, 0.533) | 222 |
| Comparative Example 27 | 4.41 | 48.1 | (0.463, 0.539) | 179 |
| Comparative Example 28 | 4.29 | 51.2 | (0.446, 0.537) | 230 |
| Comparative Example 29 | 4.45 | 57.9 | (0.443, 0.542) | 245 |
| Comparative Example 30 | 4.34 | 52.0 | (0.454, 0.543) | 228 |
| Comparative Example 31 | 4.75 | 70.0 | (0.456, 0.532) | 96 |
| Comparative Example 32 | 4.99 | 66.0 | (0.455, 0.532) | 105 |
| Comparative Example 33 | 6.15 | 48.1 | (0.446, 0.536) | 171 |
| Comparative Example 34 | 5.11 | 55.6 | (0.443, 0.534) | 148 |
| Comparative Example 35 | 6.05 | 64.4 | (0.455, 0.532) | 116 |
| Comparative Example 36 | 7.10 | 77.1 | (0.465, 0.538) | 80 |
| Comparative Example 37 | 6.60 | 67.2 | (0.454, 0.532) | 105 |
| Comparative Example 38 | 6.35 | 69.1 | (0.463, 0.537) | 136 |
| Comparative Example 39 | 6.55 | 66.1 | (0.444, 0.536) | 180 |
| Comparative Example 40 | 4.66 | 71.0 | (0.443, 0.542) | 112 |
| Comparative Example 41 | 6.02 | 53.0 | (0.453, 0.523) | 162 |
| Comparative Example 42 | 5.99 | 65.0 | (0.463, 0.539) | 170 |
| Comparative Example 43 | 6.69 | 55.0 | (0.446, 0.537) | 205 |
| Comparative Example 44 | 7.10 | 68.0 | (0.443, 0.542) | 98 |
| Comparative Example 45 | 6.95 | 62.0 | (0.454, 0.543) | 150 |
| Comparative Example 46 | 6.77 | 65.0 | (0.464, 0.533) | 205 |
| Comparative Example 47 | 5.98 | 58.0 | (0.454, 0.532) | 177 |
| Comparative Example 48 | 6.09 | 70.0 | (0.455, 0.533) | 155 |
| Comparative Example 49 | 7.02 | 40.6 | (0.452, 0.546) | 99 |
| Comparative Example 50 | 4.55 | 55.0 | (0.454, 0.532) | 200 |
| Comparative Example 51 | 4.41 | 61.1 | (0.463, 0.538) | 188 |
| Comparative Example 52 | 4.82 | 51.1 | (0.444, 0.536) | 210 |
| Comparative Example 53 | 4.75 | 54.0 | (0.443, 0.542) | 225 |
| Comparative Example 54 | 4.69 | 52.0 | (0.453, 0.532) | 220 |
| Comparative Example 55 | 4.55 | 58.2 | (0.463, 0.538) | 191 |
| Comparative Example 56 | 5.01 | 49.1 | (0.443, 0.535) | 234 |
| Comparative Example 57 | 4.91 | 51.1 | (0.443, 0.543) | 251 |
| Comparative Example 58 | 4.44 | 68.2 | (0.454, 0.532) | 110 |

TABLE 1-continued

|  | Voltage (V) | Current efficiency (cd/A) | Color coordinates (x, y) | Life Time 98 at 20 mA/cm² |
|---|---|---|---|---|
| Comparative Example 59 | 4.39 | 70.1 | (0.459, 0.535) | 124 |
| Comparative Example 60 | 4.74 | 64.3 | (0.444, 0.535) | 125 |
| Comparative Example 61 | 4.69 | 66.0 | (0.443, 0.542) | 141 |

As seen in Table 1, it can be confirmed that the organic light emitting diode using the compound represented by Chemical Formula 1 as the electron transport material according to the exemplary embodiment of the present specification has high efficiency, a low driving voltage, and a long life-span as compared to the case where an existing electron transport material is used.

This is because the compound represented by Chemical Formula 1 is a bipolar type including both a p type and an n type, so that hole leakage can be prevented and an exciton can be effectively confined in the light emitting layer.

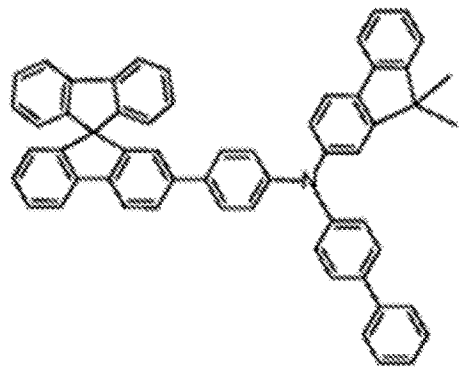

The invention claimed is:

1. An organic light emitting diode comprising:
an anode;
a cathode;
a light emitting layer provided between the anode and the cathode;
an organic material layer provided between the cathode and the light emitting layer and including a compound of any one of the following Chemical Formulae 1-2 to 1-4:

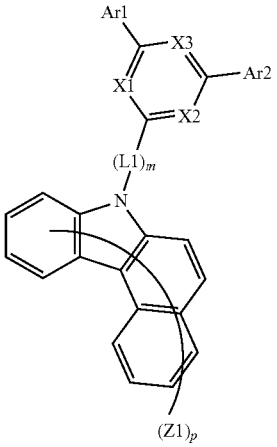

Chemical Formula 1-2

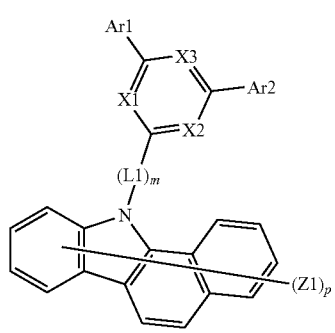

Chemical Formula 1-3

Chemical Formula 1-4 wherein in Chemical Formulae 1-2 to 1-4:

X1 to X3 are the same as or different from each other, and are each independently N or CH;

at least one of X1 to X3 is N;

L1 is a substituted or unsubstituted monocyclic arylene group having 6 to 24 carbon atoms;

m is an integer of 1 to 2;

in the case where m is an integer of 2, the two L1s are the same as or different from each other; and Ar1 and Ar2 are the same as or different from each other, and are each independently a substituted or unsubstituted monocyclic or polycyclic aryl group having 6 to 20 carbon atoms;

provided that at least one of Ar1 and Ar2 is a phenyl group substituted by a substituted or unsubstituted aryl group; a biphenyl group substituted by one or two or more substituent groups selected from the group consisting of a substituted or unsubstituted alkyl group and a substituted or unsubstituted aryl group; a terphenyl group that is unsubstituted or substituted by one or two or more substituent groups selected from the group consisting of a substituted or unsubstituted alkyl group and a substituted or unsubstituted aryl group; a naphthyl group that is unsubstituted or substituted by one or two or more substituent groups selected from the group consisting of a substituted or unsubstituted alkyl group and a substituted or unsubstituted aryl group; a triphenylenylene group that is unsubstituted or substituted by one or two or more substituent groups selected from the group consisting of a substituted or unsubstituted alkyl group and a substituted or unsubstituted aryl group; a fluorenyl group that is unsubstituted or substituted by a substituted or unsubstituted alkyl group; or a phenanthrenyl group substituted by one or two or more substituent groups selected from the group consisting of a substituted or unsubstituted alkyl group and a substituted or unsubstituted aryl group;

Z1 is deuterium; and p is an integer of 0 to 10, wherein the four-ring system of Chemical Formulae 1-2 to 1-4 includes as the only possible substituents the moiety

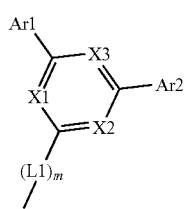

on the ring nitrogen, and hydrogen or deuterium on the carbon atoms, as defined above; and an organic material layer provided between the anode and the light emitting layer and including a compound of the following Chemical Formula 2:

Chemical Formula 2

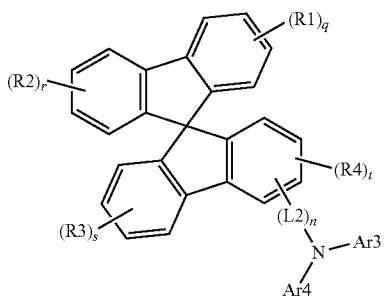

wherein in Chemical Formula 2:

Ar3 is an unsubstituted phenyl group, a substituted or unsubstituted biphenyl group, a substituted or unsubstituted fluorenyl group, a substituted or unsubstituted spirobifluorenyl group, or a substituted or unsubstituted dibenzofuran group, and Ar4 is an unsubstituted phenyl group, a substituted or unsubstituted biphenyl group, a substituted or unsubstituted fluorenyl group, a substituted or unsubstituted spirobifluorenyl group, or a substituted or unsubstituted dibenzofuran group, or Ar3 and Ar4 are bonded to each other to form a substituted or unsubstituted dihydroacridine structure;

L2 is a substituted or unsubstituted monocyclic or polycyclic arylene group having 6 to 20 carbon atoms;

n is an integer of 0 to 5;

in the case where n is 2 or more, the two or more L2s are the same as or different from each other;

R1 to R4 are the same as or different from each other, and are each independently hydrogen or deuterium;

q, r, and s are each an integer of 1 to 4;

t is an integer of 1 to 3;

in the case where q is 2 or more, the two or more R1s are the same as or different from each other;

in the case where r is 2 or more, the two or more R2s are the same as or different from each other;

in the case where s is 2 or more, the two or more R3s are the same as or different from each other; and in the case where t is 2 or more, the two or more R4s are the same as or different from each other.

2. The organic light emitting diode of claim 1, wherein the organic material layer including the compound of any one of the Chemical Formulae 1-2 to 1-4 is an electron transport layer, an electron injection layer, or a layer simultaneously transporting and injecting electrons.

3. The organic light emitting diode of claim 1, wherein the organic material layer including the compound of Chemical Formula 2 is an electron blocking layer.

4. The organic light emitting diode of claim 1, wherein the organic material layer including the compound of Chemical Formula 2 is in contact with the light emitting layer.

5. The organic light emitting diode of claim 1, further comprising:

one or two or more layers selected from the group consisting of an electron injection layer and an electron transport layer between the light emitting layer and the cathode.

6. The organic light emitting diode of claim 1, further comprising:

one or two or more layers selected from the group consisting of a hole injection layer, a hole transport layer, and an electron blocking layer between the light emitting layer and the anode.

7. The organic light emitting diode of claim 1, wherein L1 is a substituted or unsubstituted phenylene group, a substituted or unsubstituted biphenylene group, a substituted or unsubstituted terphenylene group, or a substituted or unsubstituted quaterphenylene group.

8. The organic light emitting diode of claim 1, wherein X1 to X3 are N.

9. The organic light emitting diode of claim 1, wherein the compound of any one of Chemical Formulae 1-2 to 1-4 is any one of the following compounds:

Chemical Formula 1-2-1

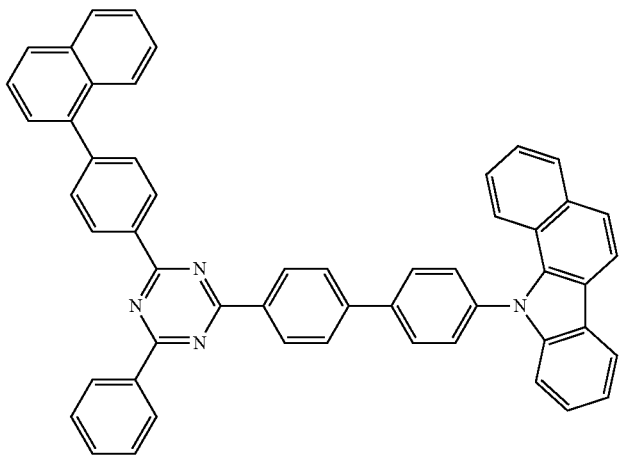

-continued
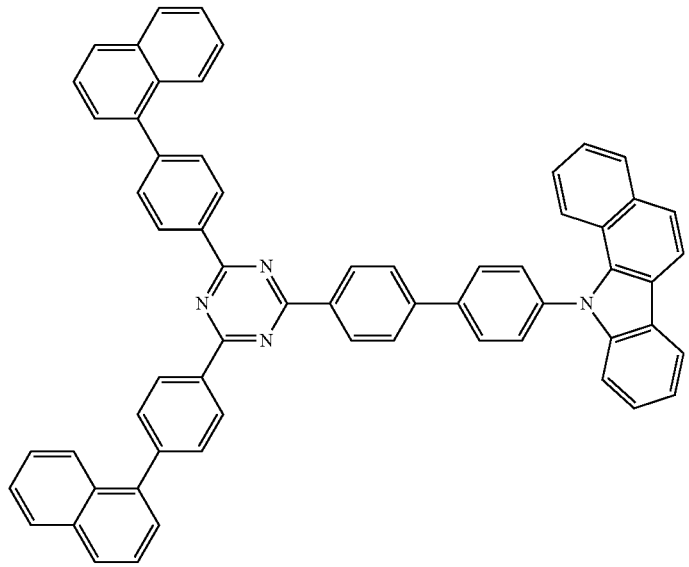
Chemical Formula 1-2-2
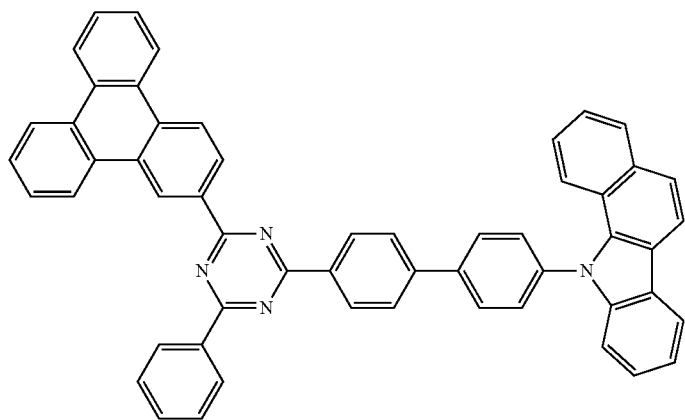
Chemical Formula 1-2-3
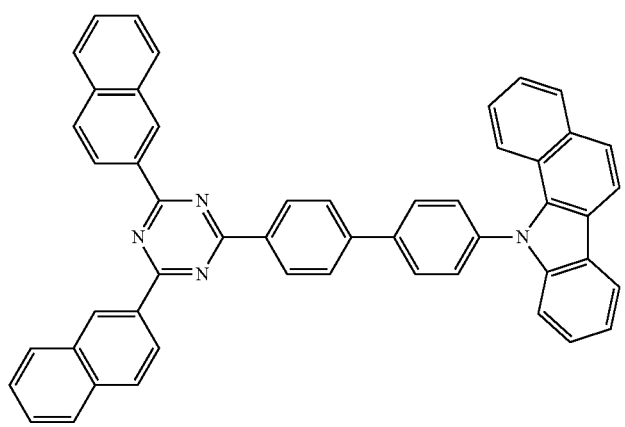
Chemical Formula 1-2-5

Chemical Formula 1-3-1
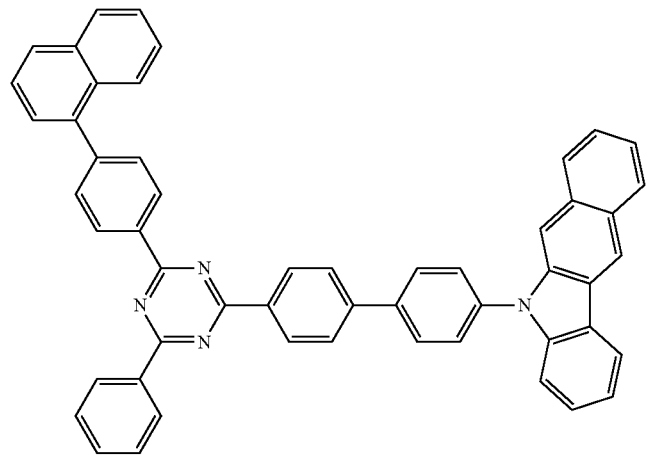
Chemical Formula 1-3-2
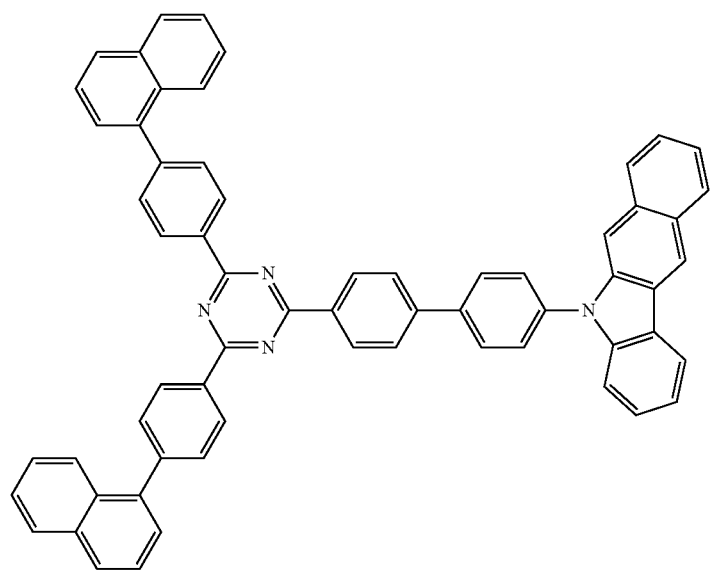
Chemical Formula 1-3-3
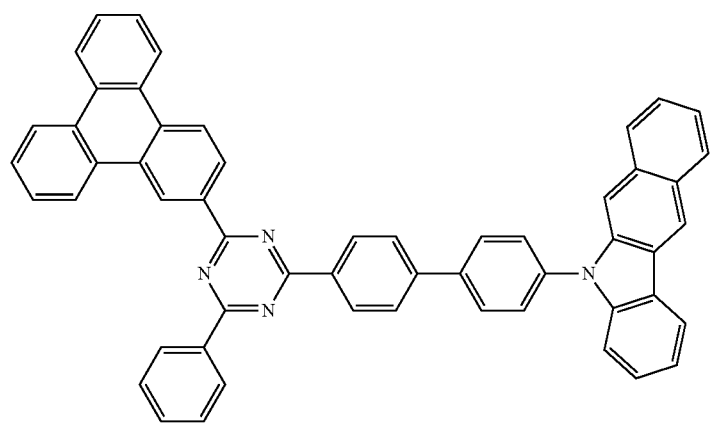

Chemical Formula 1-3-5
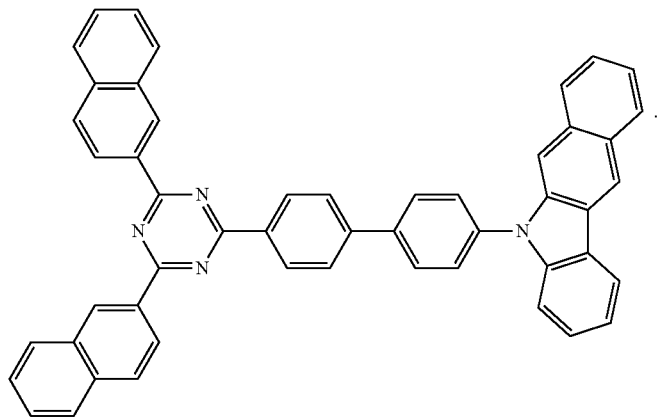
Chemical Formula 1-4-1
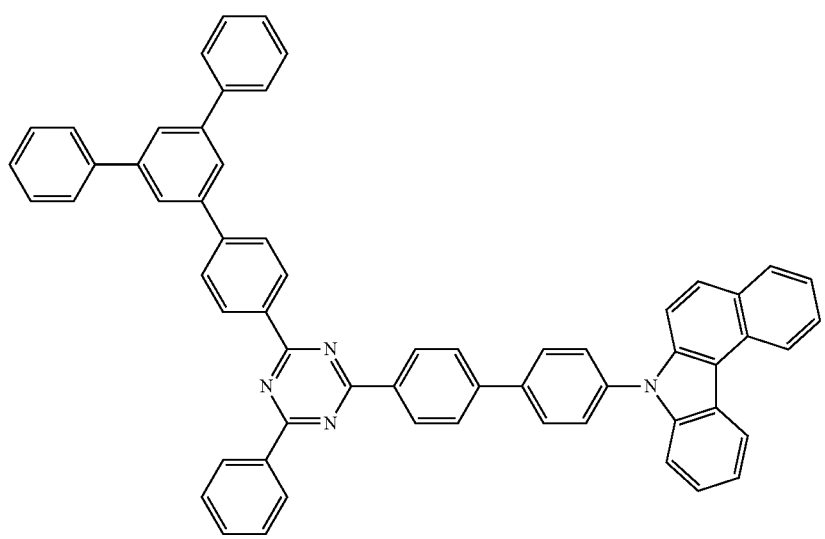
Chemical Formula 1-4-2
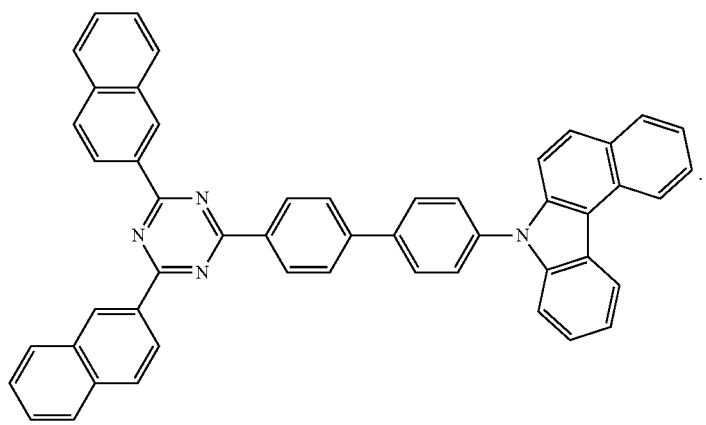

10. The organic light emitting diode of claim 1, wherein:
L2 is a substituted or unsubstituted phenylene group; or
n is 0.

11. The organic light emitting diode of claim 1, wherein the compound of Chemical Formula 2 is any one of the following Chemical Formulas 2-1 to 2-45:

Chemical Formula 2-1

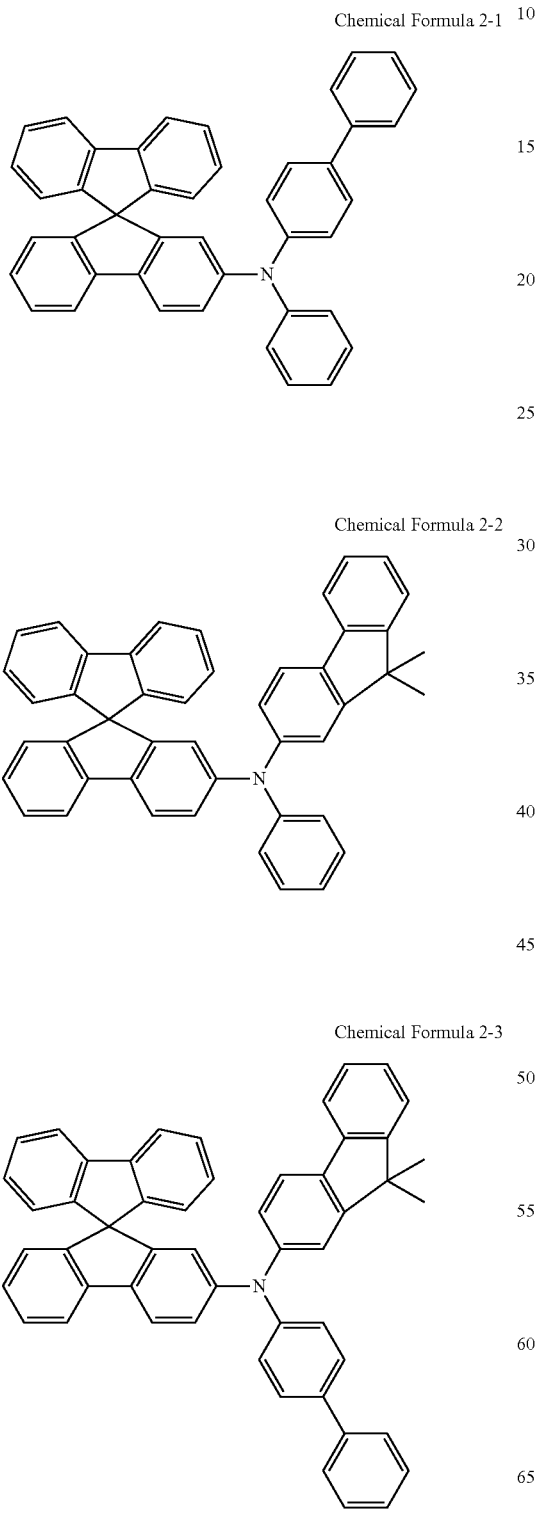

Chemical Formula 2-2

Chemical Formula 2-3

-continued

Chemical Formula 2-4

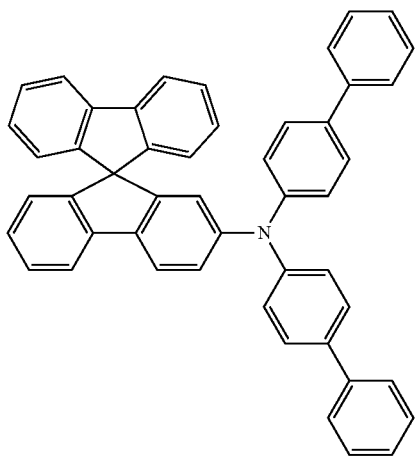

Chemical Formula 2-5

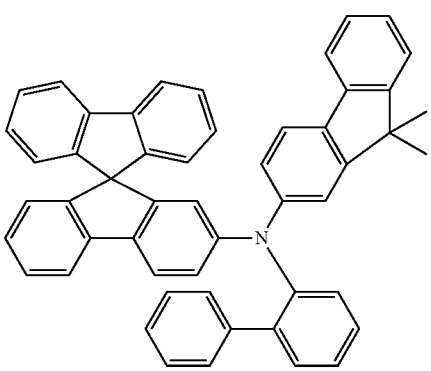

Chemical Formula 2-6

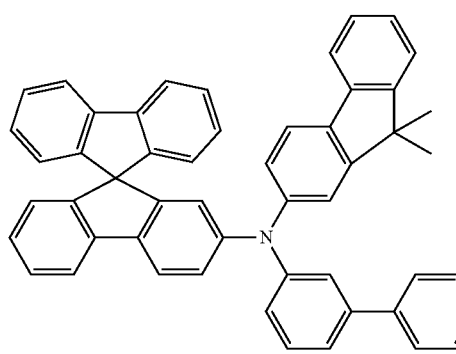

Chemical Formula 2-7

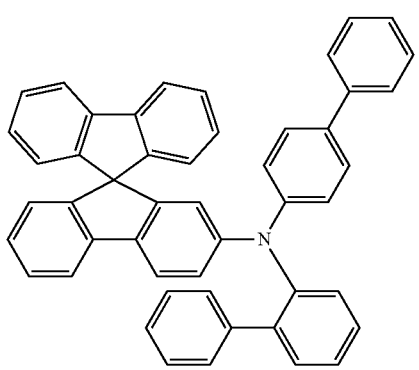

Chemical Formula 2-8
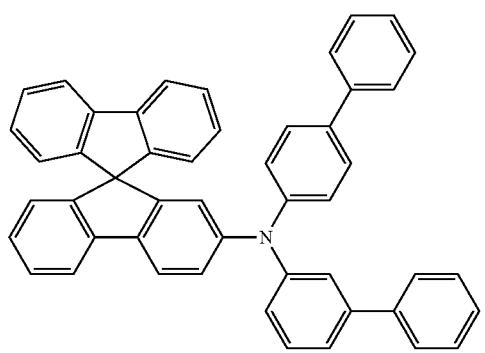
Chemical Formula 2-9
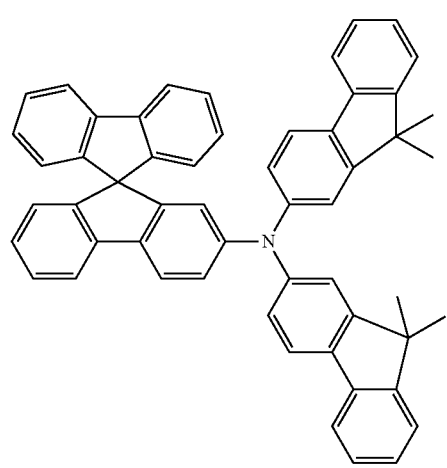
Chemical Formula 2-10
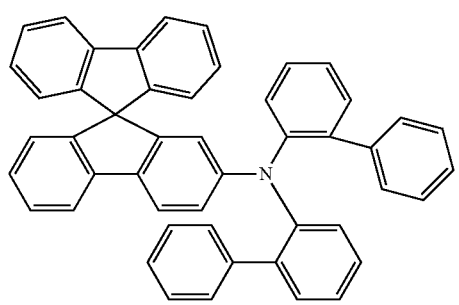
Chemical Formula 2-11
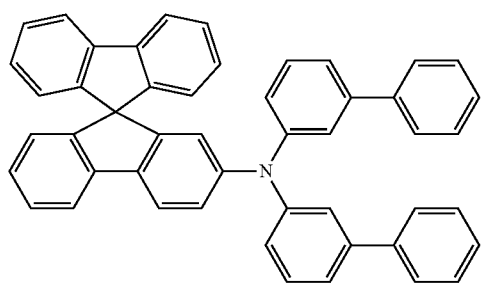
Chemical Formula 2-12
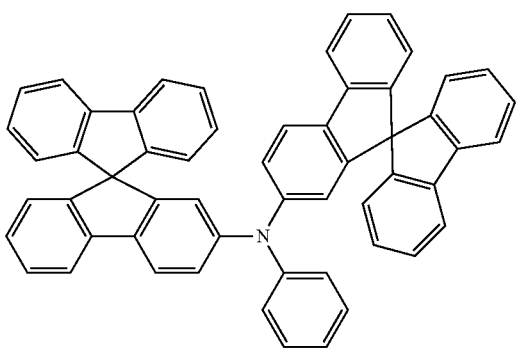
Chemical Formula 2-13
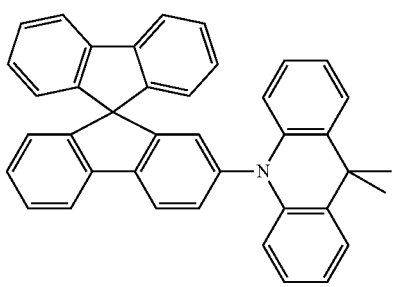
Chemical Formula 2-14
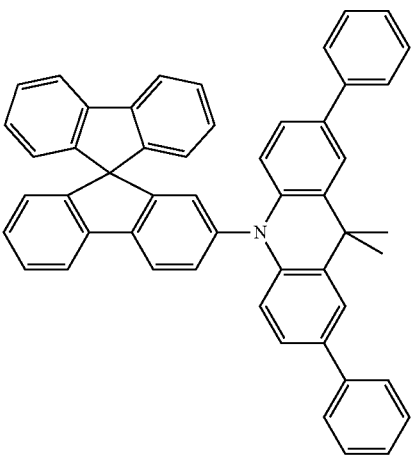
Chemical Formula 2-15
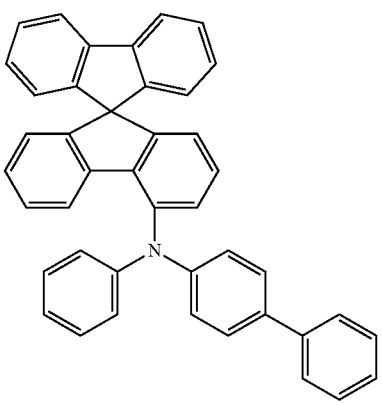

Chemical Formula 2-16
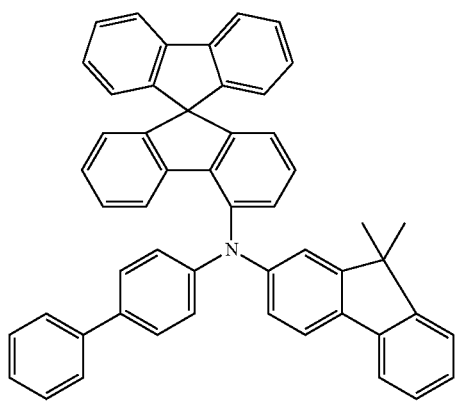
Chemical Formula 2-19
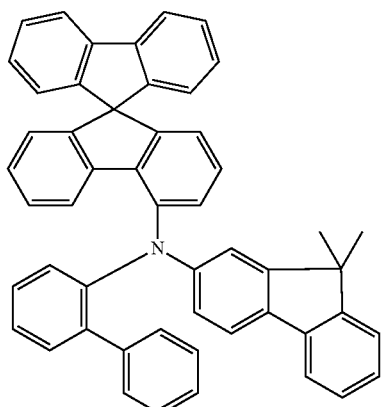
Chemical Formula 2-17
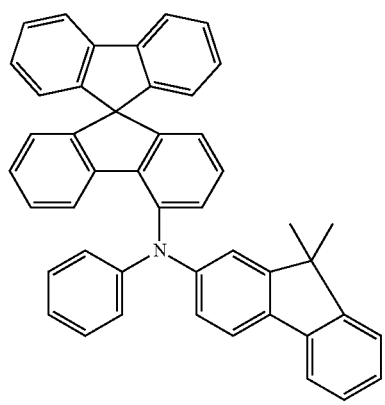
Chemical Formula 2-20
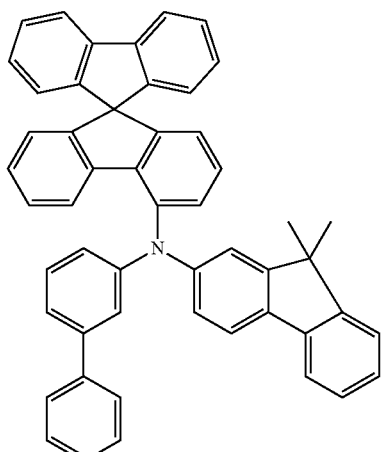
Chemical Formula 2-18
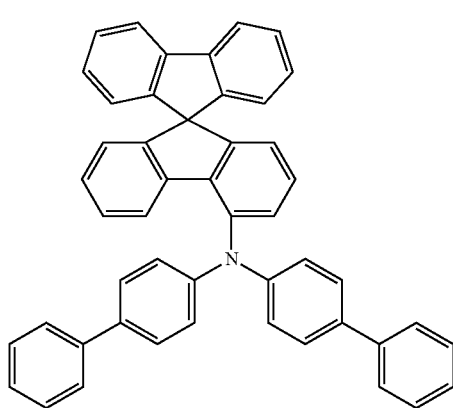
Chemical Formula 2-21
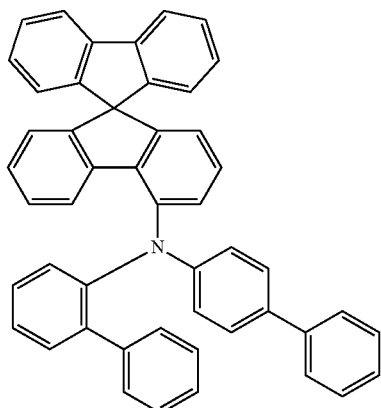

Chemical Formula 2-22
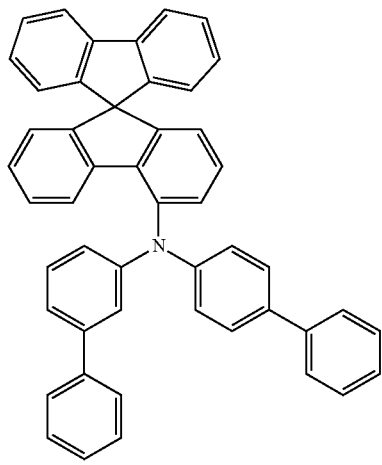
Chemical Formula 2-25
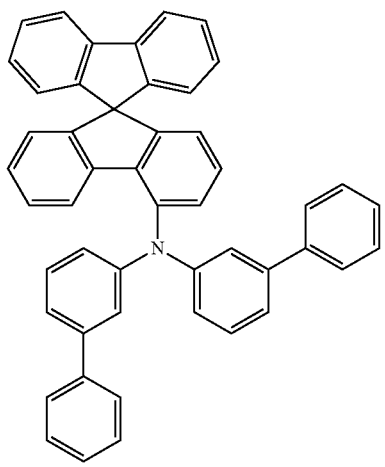
Chemical Formula 2-23
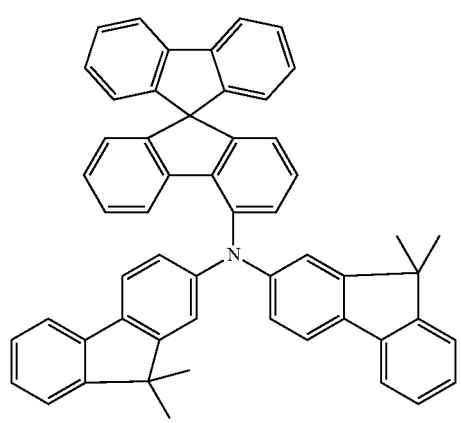
Chemical Formula 2-26
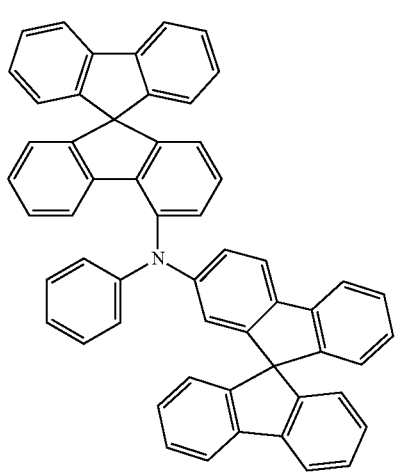
Chemical Formula 2-24
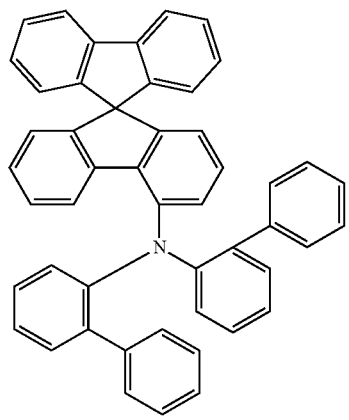
Chemical Formula 2-27
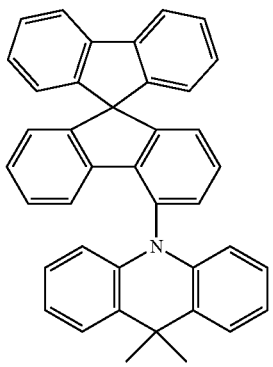

Chemical Formula 2-28
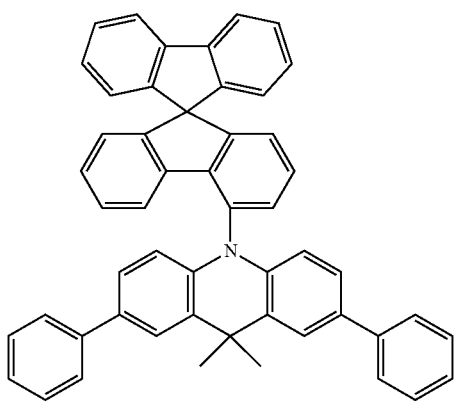
Chemical Formula 2-29
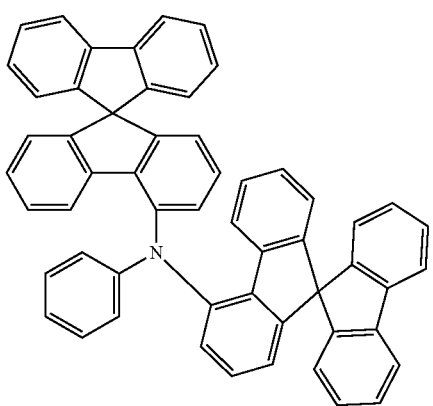
Chemical Formula 2-30
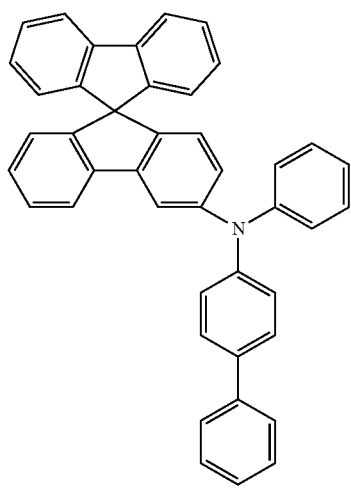
Chemical Formula 2-31
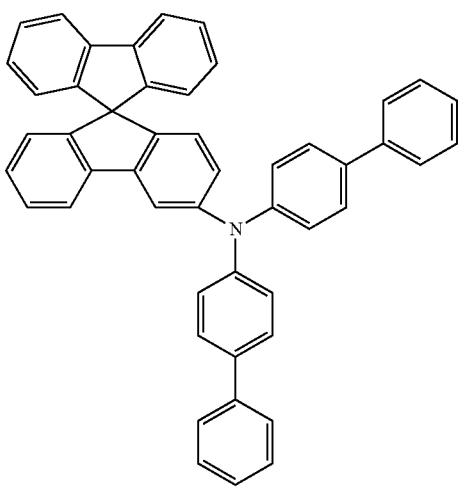
Chemical Formula 2-32
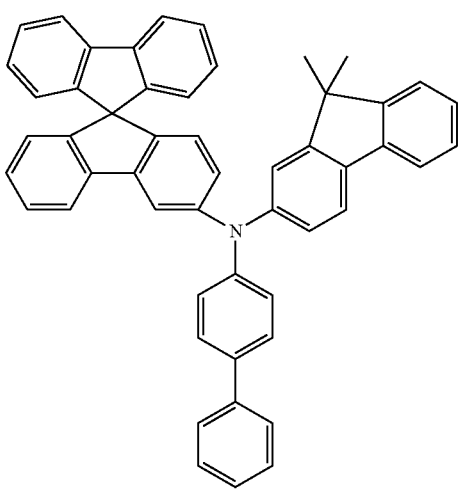
Chemical Formula 2-33
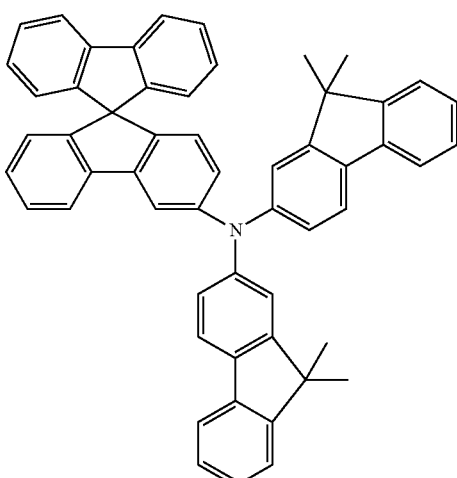

-continued
Chemical Formula 2-34
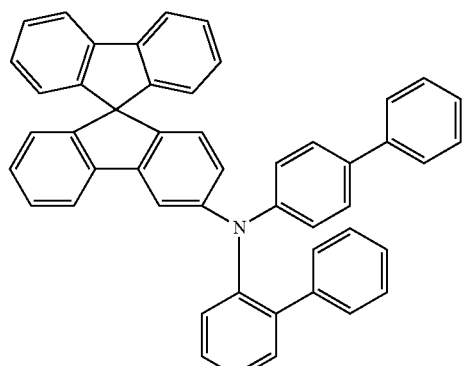
Chemical Formula 2-35
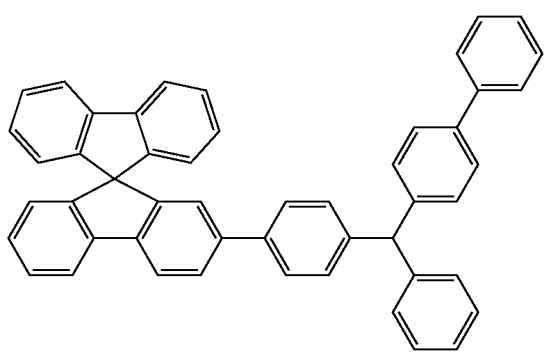
Chemical Formula 2-36
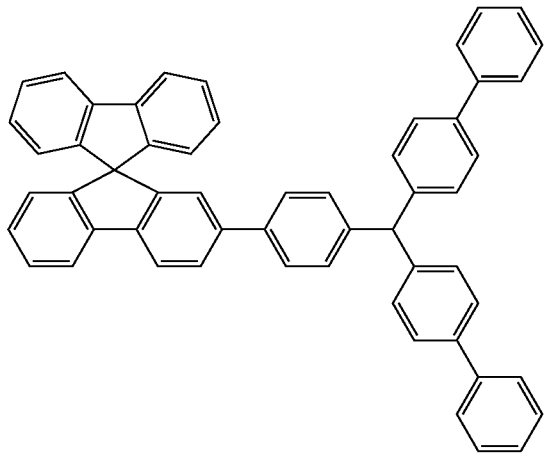
Chemical Formula 2-37
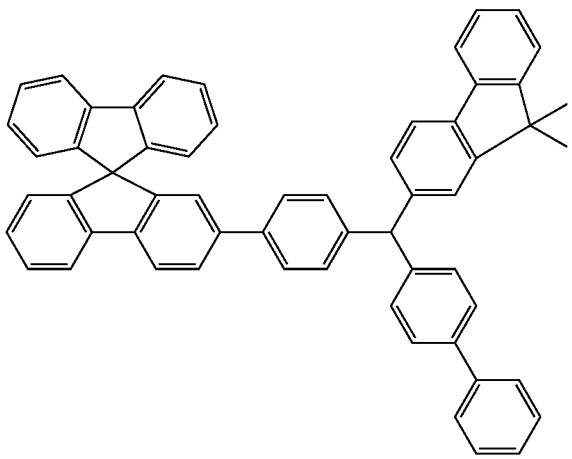
Chemical Formula 2-38
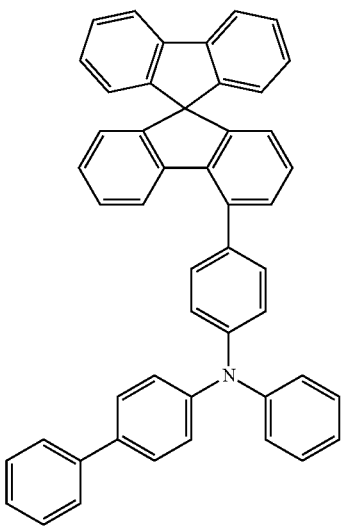
Chemical Formula 2-39
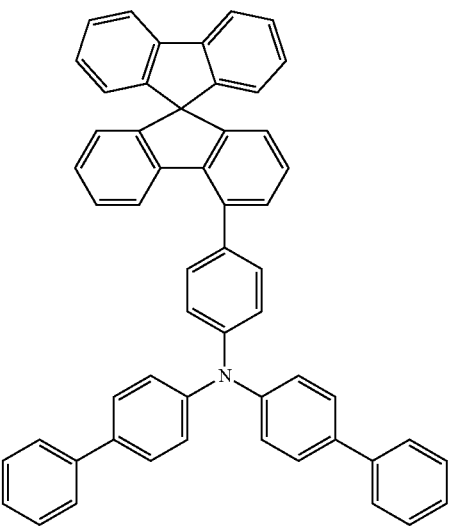

-continued
Chemical Formula 2-40
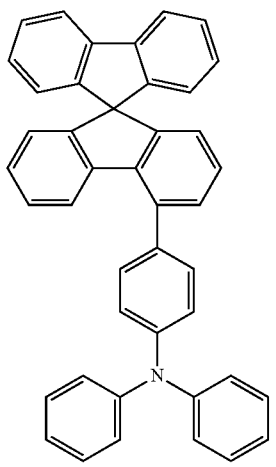
Chemical Formula 2-41
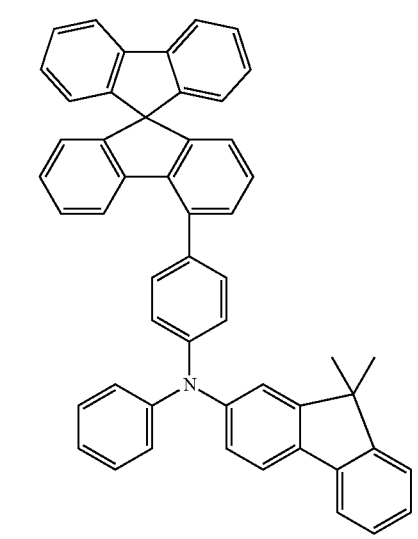
Chemical Formula 2-42
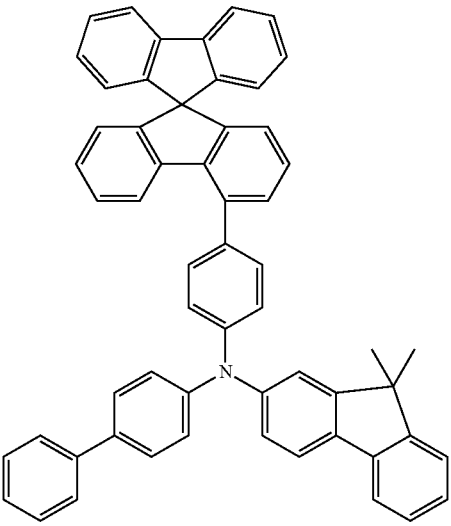
-continued
Chemical Formula 2-43
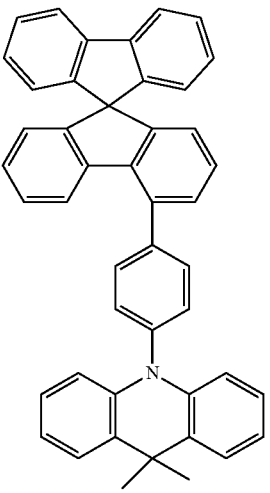
Chemical Formula 2-44
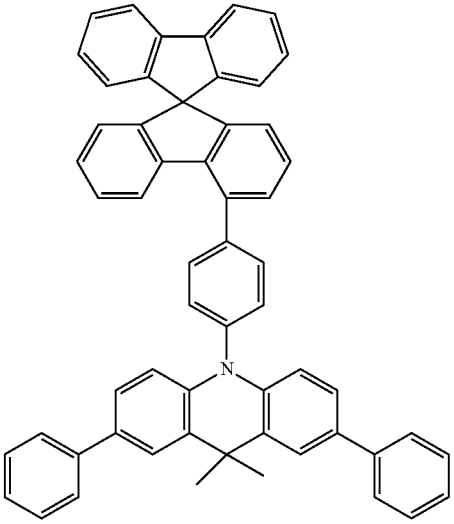
Chemical Formula 2-45
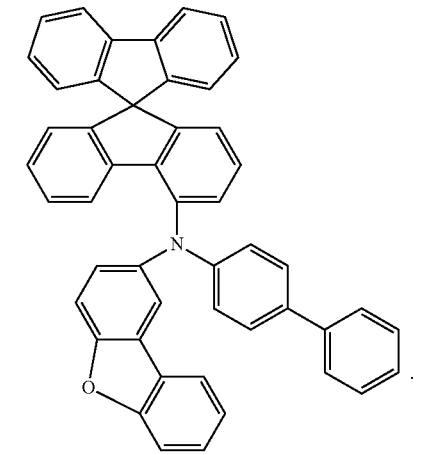
12. An organic light emitting diode comprising:
an anode;
a cathode;
a light emitting layer provided between the anode and the cathode;

an organic material layer provided between the cathode and the light emitting layer and including a compound of the following Chemical Formula 1-1:

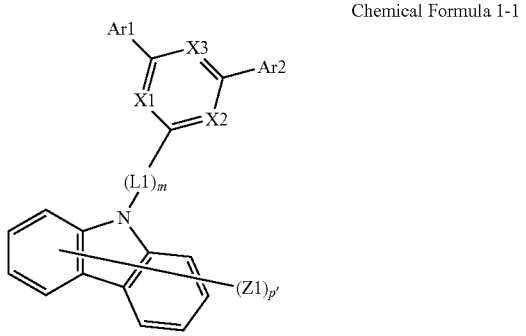

Chemical Formula 1-1 wherein in Chemical Formula 1-1:
X1 to X3 are the same as or different from each other, and are each independently N or CH;
at least one of X1 to X3 is N;
L1 is a substituted or unsubstituted phenylene group, a substituted or unsubstituted biphenylene group, a substituted or unsubstituted terphenylene group, or a substituted or unsubstituted quaterphenylene group;
m is an integer of 1 to 2;
in the case where m is an integer of 2, the two L1s are the same as or different from each other; and
Ar1 and Ar2 are the same as or different from each other, and are each independently a phenyl group that is unsubstituted or substituted by one or two or more substituent groups selected from the group consisting of a substituted or unsubstituted alkyl group and a substituted or unsubstituted aryl group; a biphenyl group that is unsubstituted or substituted by one or two or more substituent groups selected from the group consisting of a substituted or unsubstituted alkyl group and a substituted or unsubstituted aryl group; a terphenyl group that is unsubstituted or substituted by one or two or more substituent groups selected from the group consisting of a substituted or unsubstituted alkyl group and a substituted or unsubstituted aryl group; a naphthyl group that is unsubstituted or substituted by one or two or more substituent groups selected from the group consisting of a substituted or unsubstituted alkyl group and a substituted or unsubstituted aryl group; a triphenylenyl group that is unsubstituted or substituted by one or two or more substituent groups selected from the group consisting of a substituted or unsubstituted alkyl group and a substituted or unsubstituted aryl group; a fluorenyl group that is unsubstituted or substituted by a substituted or unsubstituted alkyl group; or a phenanthrenyl group that is substituted by one or two or more substituent groups selected from the group consisting of a substituted or unsubstituted alkyl group and a substituted or unsubstituted aryl group;
provided that at least one of Ar1 and Ar2 is a phenyl group that is unsubstituted or substituted by a substituted or unsubstituted aryl group; a biphenyl group that is unsubstituted or substituted by one or two or more substituent groups selected from the group consisting of a substituted or unsubstituted alkyl group and a substituted or unsubstituted aryl group; a terphenyl group that is unsubstituted or substituted by one or two or more substituent groups selected from the group consisting of a substituted or unsubstituted alkyl group and a substituted or unsubstituted aryl group; a naphthyl group that is unsubstituted or substituted by one or two or more substituent groups selected from the group consisting of a substituted or unsubstituted alkyl group and a substituted or unsubstituted aryl group; a triphenylenyl group that is unsubstituted or substituted by one or two or more substituent groups selected from the group consisting of a substituted or unsubstituted alkyl group and a substituted or unsubstituted aryl group; a fluorenyl group that is unsubstituted or substituted by a substituted or unsubstituted alkyl group; or a phenanthrenyl group that is substituted by one or two or more substituent groups selected from the group consisting of a substituted or unsubstituted alkyl group and a substituted or unsubstituted aryl group;
Z1 is deuterium;
P' is an integer of 0 to 8; and
an organic material layer provided between the anode and the light emitting layer and including a compound of the following Chemical Formula 2:

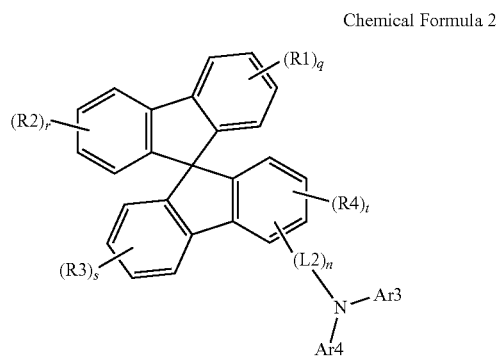

Chemical Formula 2 wherein in Chemical Formula 2:
Ar3 is an unsubstituted phenyl group, a substituted or unsubstituted biphenyl group, a substituted or unsubstituted fluorenyl group, a substituted or unsubstituted spirobifluorenyl group, or a substituted or unsubstituted dibenzofuran group, and Ar4 is an unsubstituted phenyl group, a substituted or unsubstituted biphenyl group, a substituted or unsubstituted fluorenyl group, a substituted or unsubstituted spirobifluorenyl group, or a substituted or unsubstituted dibenzofuran group, or Ar3 and Ar4 are bonded to each other to form a substituted or unsubstituted dihydroacridine structure;
L2 is a substituted or unsubstituted monocyclic or polycyclic arylene group having 6 to 20 carbon atoms;
n is an integer of 0 to 5;
in the case where n is 2 or more, the two or more L2s are the same as or different from each other;
R1 to R4 are the same as or different from each other, and are each independently hydrogen or deuterium;
q, r, and s are each an integer of 1 to 4;
t is an integer of 1 to 3;
in the case where q is 2 or more, the two or more R1s are the same as or different from each other;
in the case where r is 2 or more, the two or more R2s are the same as or different from each other;
in the case where s is 2 or more, the two or more R3s are the same as or different from each other; and in the case where t is 2 or more, the two or more R4s are the same as or different from each other.

13. The organic light emitting diode of claim 12, wherein Ar1 and Ar2 are the same as or different from each other, and are each independently an unsubstituted phenyl group or an unsubstituted biphenyl group.

14. The organic light emitting diode of claim 12, wherein Ar1 and Ar2 are the same as or different from each other, and are each independently a phenyl group that is unsubstituted or substituted by an aryl group; a biphenyl group; a terphenyl group; a naphthyl group; or a triphenylenylene group;

provided that at least one of Ar1 and Ar2 is a phenyl group substituted by an aryl group; a terphenyl group; a naphthyl group; or a triphenylenylene group.

15. The organic light emitting diode of claim 12, wherein the compound of Chemical Formula 1-1 is any one of the following compounds:

Chemical Formula 1-1-3

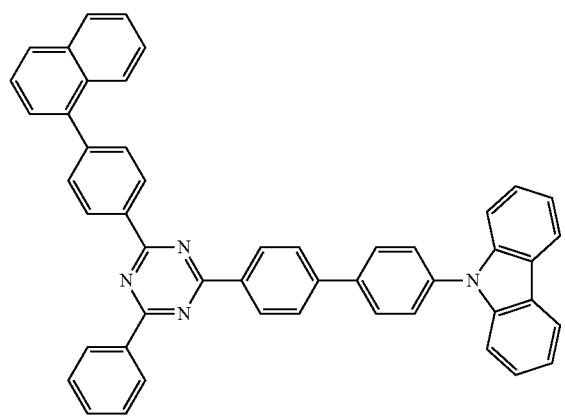

Chemical Formula 1-1-4

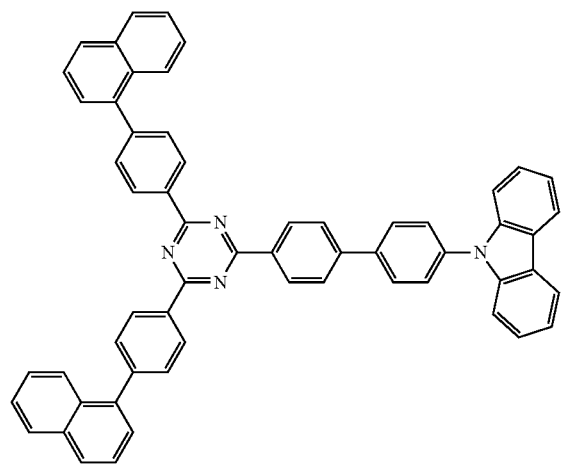

Chemical Formula 1-1-5

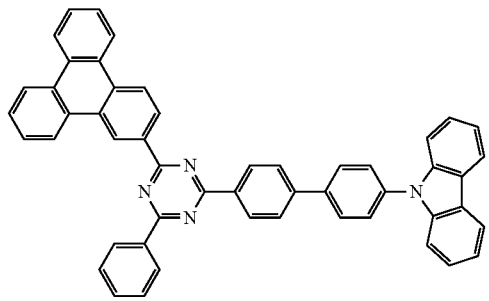

Chemical Formula 1-1-7

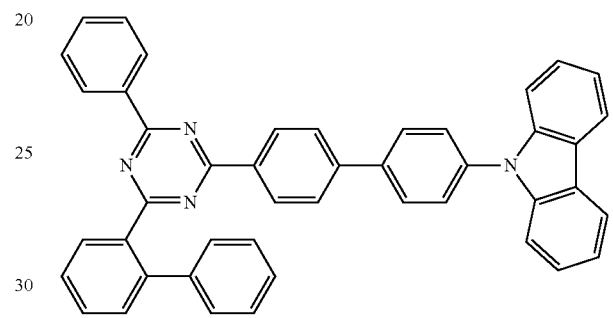

Chemical Formula 1-1-12

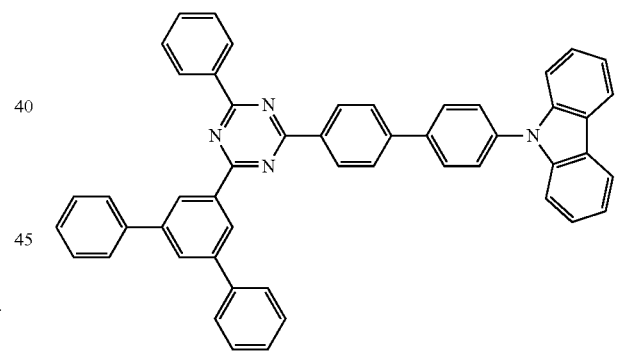

Chemical Formula 1-1-17

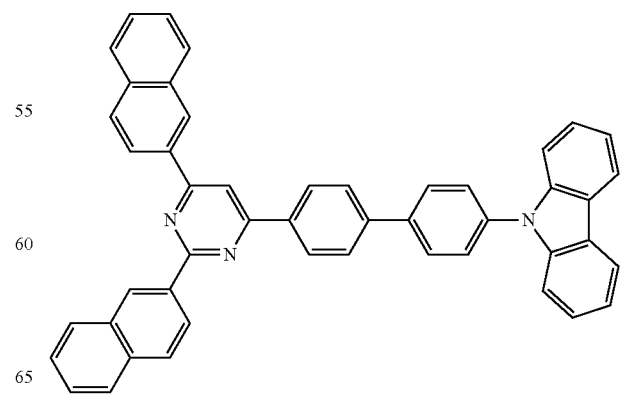

Chemical Formula 1-1-18
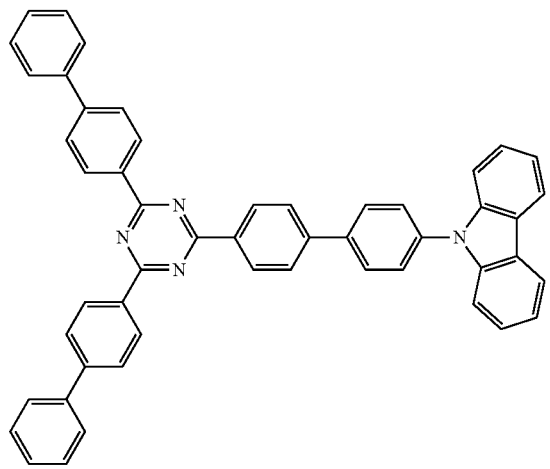
Chemical Formula 1-1-24
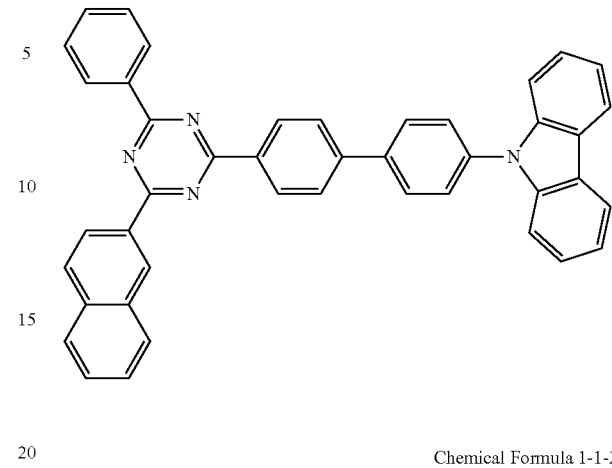
Chemical Formula 1-1-19
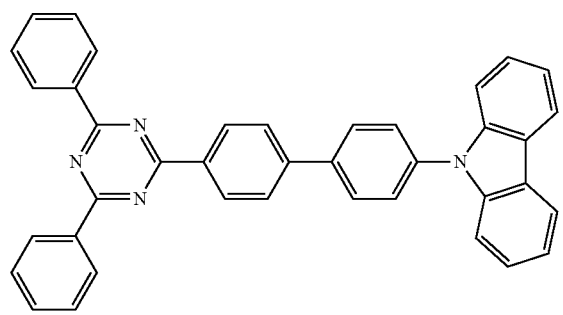
Chemical Formula 1-1-25
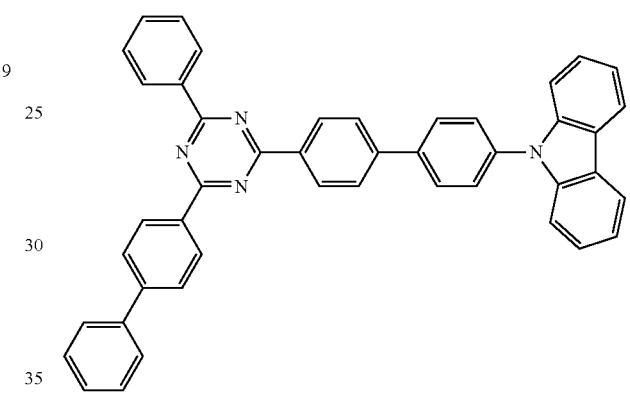
Chemical Formula 1-1-21
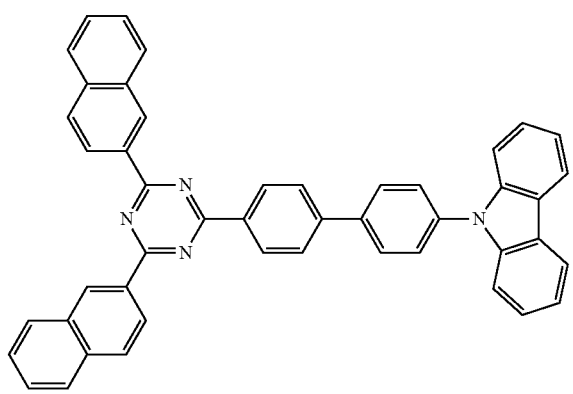
Chemical Formula 1-1-28
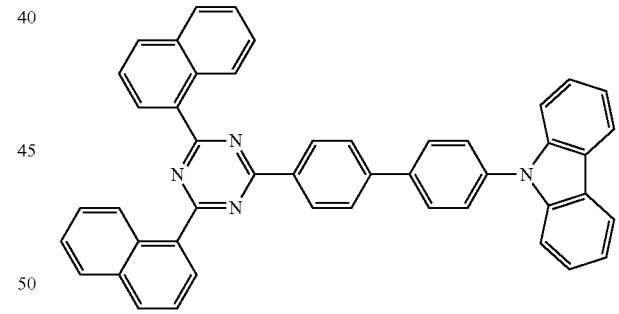
Chemical Formula 1-1-23
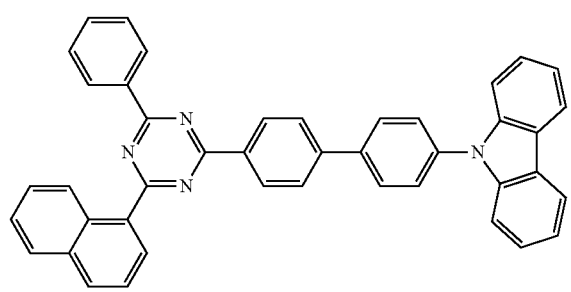
Chemical Formula 1-1-33
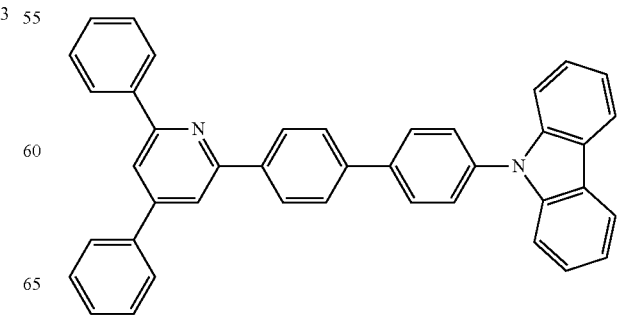

-continued

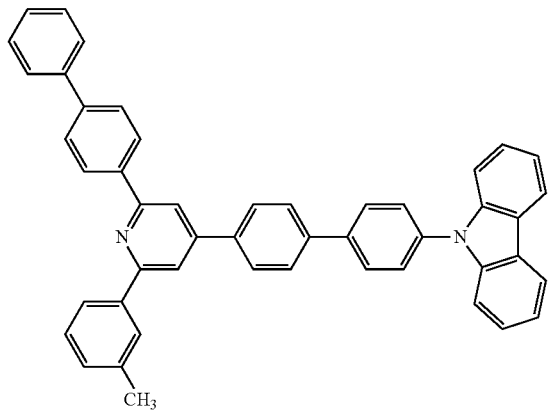

Chemical Formula 1-1-35

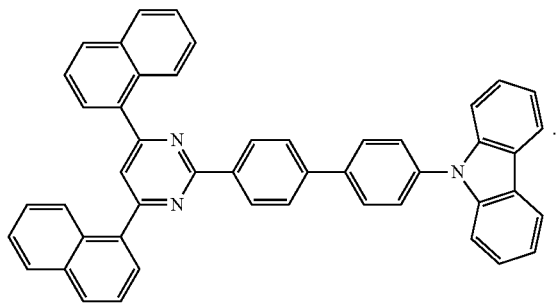

Chemical Formula 1-1-37

16. The organic light emitting diode of claim 12, wherein:
L1 is a substituted or unsubstituted terphenylene group; and
m is 1.

17. The organic light emitting diode of claim 16, wherein the compound of Chemical Formula 1-1 is Chemical Formula 1-1-32:

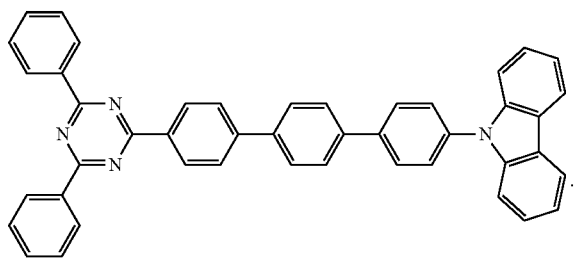

Chemical Formula 1-1-32

18. The organic light emitting diode of claim 12, wherein:
L1 is a substituted or unsubstituted quaterphenylene group; and
m is 1.

19. The organic light emitting diode of claim 13, wherein the compound of Chemical Formula 1-1 is Chemical Formula 1-1-8 or 1-1-9:

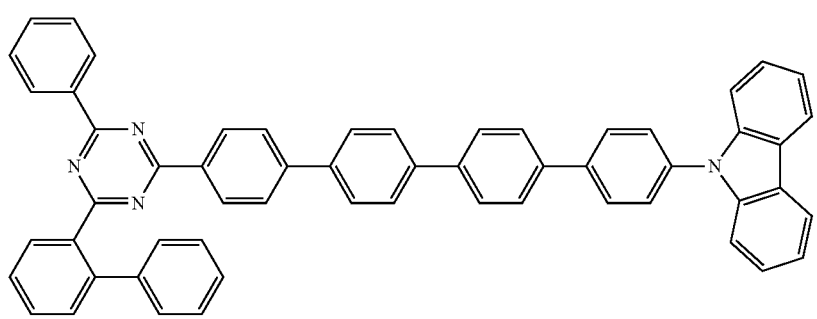

Chemical Formula 1-1-8

Chemical Formula 1-1-9
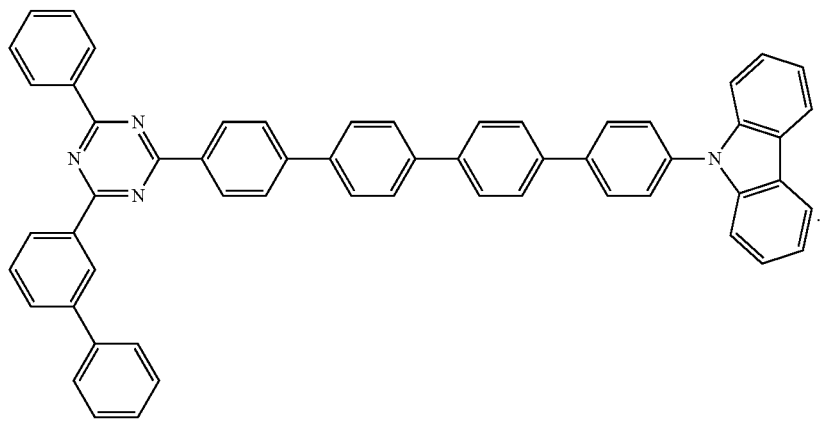
* * * * *

UNITED STATES PATENT AND TRADEMARK OFFICE
CERTIFICATE OF CORRECTION

PATENT NO. : 11,737,354 B2
APPLICATION NO. : 16/888395
DATED : August 22, 2023
INVENTOR(S) : Jungoh Huh et al.

Page 1 of 2

It is certified that error appears in the above-identified patent and that said Letters Patent is hereby corrected as shown below:

In the Claims

In Claim 11, at Column 119, Lines 25-40, the compound should appear as follows:

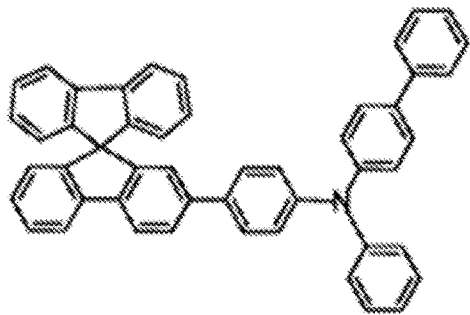

In Claim 11, at Column 119, Lines 48-66, the compound should appear as follows:

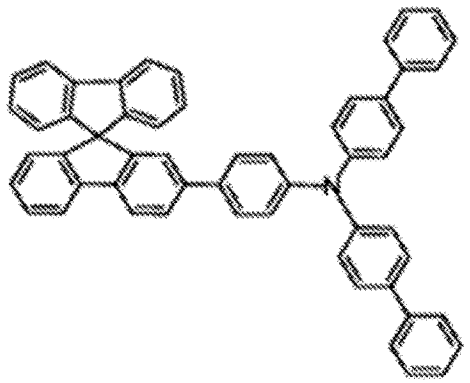

Signed and Sealed this
Twenty-seventh Day of February, 2024

Katherine Kelly Vidal
*Director of the United States Patent and Trademark Office*

CERTIFICATE OF CORRECTION (continued)
U.S. Pat. No. 11,737,354 B2

In Claim 11, at Column 120, Lines 2-20, the compound should appear as follows: